(12) United States Patent
Lanahan et al.

(10) Patent No.: US 7,169,595 B2
(45) Date of Patent: Jan. 30, 2007

(54) THERMOTOLERANT PHYTASE FOR ANIMAL FEED

(75) Inventors: Michael B. Lanahan, Research Triangle Park, NC (US); Scott Betts, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 11/412,185

(22) Filed: Apr. 26, 2006

(65) Prior Publication Data

US 2006/0228400 A1  Oct. 12, 2006

Related U.S. Application Data

(62) Division of application No. 10/334,671, filed on Dec. 30, 2002.

(60) Provisional application No. 60/344,476, filed on Dec. 28, 2001.

(51) Int. Cl.
*C12N 9/16* (2006.01)

(52) U.S. Cl. ............... 435/196; 435/252.3; 435/320.1; 536/23.2; 800/278

(58) Field of Classification Search ................ 435/196, 435/252.3, 320.1; 536/23.2; 800/278
See application file for complete search history.

(56) References Cited

U.S. PATENT DOCUMENTS 6,110,719 A    8/2000   Kretz ......................... 435/196
6,358,722 B1   3/2002   van Loon .................... 435/196

FOREIGN PATENT DOCUMENTS

EP    0 897 985 A    2/1999
WO    WO 00/58481    10/2000

OTHER PUBLICATIONS

Altschul et al, *Basic Local Alignment Search Tool Journal of Molecular Biology*, vol. 215 (1990) pp. 403-410.
Aoyama, T. and Chua N., *A glucocorticoid-mediated transcriptional induction system in transgenic plants The Plant Journal*, vol. 11(3) (1997) pp. 605-612.
Campbell, W. and Gowri, G., *Codon Usage in Higher Plants, Green Algae, and Cyanobacteria Plant Physiology*, vol. 92 (1990) pp. 1-11.
Christou et al, *Production of Transgenic Rice (Oryza sativa I.) Plants from Agronomically Important Indice and Japonica Varieties Via Electric Discharge Particle Acceleration of Exogeneous DNA into Immature Zygotic Embryos Bio/Technology*, vol. 9, (Oct. 1991) pp. 957-962.
Christou et al, *Stable Transformation of Soybean Callus By DNA-Coated Gold Particles Plant Physiology*, vol. 87 (1988) pp. 671-674.
Crossway et al, *Integration of foreign DNA following microinjection of tobacco mesophyll protoplasts Molecular & General Genetics*, vol. 202 (1986) pp. 179-185.
Czakó et al, *Differential manifestation of seed mortality induced by seed-specific expression of the gene for diphtheria toxin A chain in Arabidopsis and tobacco Molecular & General Genetics*, vol. 235 (1992) pp. 33-40.
Dassa E., Boquet, P.L., *Identification of the gene appA for the acid phosphatase (pH optimum 2.5) of Escherichia coli. Molecular & General Genetics*, vol. 200 (1985) pp. 68-73.
Dassa et al, EBI [online] *Escherichia coli periplasmic phosphoanhydride phosphohydrolase (AppA) gene, complete cds*; retrieved Jan. 14, 2005 from EMBL; accession No. M58708.
Dassa et al, EBI [online] *Periplasmic appA protein precursor*; retrieved Jan. 14, 2005 from GenBank; accession No. P07102.
Dassa J., et al, *The complete nucleotide sequence of the Escherichia coli gene appA reveals significant homology between pH 2.5 acid phosphatase and glucose-1-phosphatase. Journal of Bacteriology*, vol. 172 (1990) pp. 5497-5500.
Datta et al, *Genetically Engineered Fertile Indica-Rice Recovered from Protoplasts Bio/Technology*, vol. 8 (Aug. 1990) pp. 736-740.
de Framond, A.J., *A metallothionein-like gene from maize (Zea mays); Cloning and characterization Federation of European Biochemical Societies*, vol. 290, No. 1,2 (Sep. 1991) p. 103-106.
Fromm et al, *Inheritance and Expression of Chimeric Genes in the Progeny of Transgenic Maize Plants Bio/Technology*, vol. 8 (Sep. 1990) pp. 833-839.
Gan, S. and Amasino, R.M., *Inhibition of Leaf Senescence by Autoregulated Production of Cytokinin Science*, vol. 270 (Dec. 22, 1995) pp. 1986-1988.
Gatz, *Chemical Control of Gene Expression Annual Review of Plant Physiology and Plant Molecular Biology*, vol. 48 (1997) pp. 89-108.
Gatz, *Chemically inducible promoters in transgenic plants Plant Biotechnology*, vol. 7, (1996) pp. 168-172.
Golovan et al, *Characterization and overproduction of the Escherichia coli appA encoded bifunctional enzyme that exhibits both phytase and acid phosphatase activities Canadian Journal of Microbiology*, ol. 46 (2000) pp. 59-71.
Gordon-Kamm et al, *Transformation of Maize Cells and Regeneration of Fertile Transgenic Plants The Plant Cell*, vol. 2 (Jul. 1990) pp. 603-618.
Graham et al, *Wound-induced Proteinase Inhibitors from Tomato Leaves The Journal of Biological Chemistry*, vol. 260, No. 11 (Jun. 10, 1985) pp. 6561-6564.
Graham, J. and Ryan, C.A., *Accumulation of a Metallo-Carboxypeptidase Inhibitor in Leaves of Wounded Potato Plants Biochemical and Biophysical Research Communications*, vol. 101, No. 4 (Aug. 31, 1981) pp. 1164-1170.

(Continued)

Primary Examiner—Tekchand Saidha
(74) Attorney, Agent, or Firm—Syngenta Biotechnology, Inc.

(57) ABSTRACT

The invention provides a synthetic phytase polynucleotide which is optimized for expression in plants and which encodes at thermotolerant phytase, as well as isolated thermotolerant phytase enzyme. Also provided are feed or food products comprising a thermotolerant phytase, and transgenic plants which express the thermotolerant phytase. Further provided are methods for making and using thermotolerant phytases, e.g., a method of using a thermotolerant phytase in feed and food processing.

49 Claims, 10 Drawing Sheets

OTHER PUBLICATIONS

Gruber et al., "Vectors for Plant Transformation" in Methods in Plant Molecular Biology and Biotechnology, Glick, B. R. and Thompson, J. E. Eds. (CRC Press, Inc., Boca Raton, 1993) pp. 89-119.

Han, Y.W., *Use of Microbial Phytase in Improving the Feed Quality of Soya Bean Meal Animal Feed Science and Technology*, vol. 24 (1989) pp. 345-350.

Hinchee et al, *Production of Transgenic Soybean Plants Using Agrobacterium-Mediated DNA Transfer Bio/Technology*, vol. 6 (Aug. 1988), pp. 915-922.

Igbasan et al, *Comparative Studies on the In Vitro Properties of Phytase from Various Microbial Origins Archives of Animal Nutrition*, vol. 53 (2000) p. 353-373.

Ingelbrecht et al, *Different 3' End Regions Strongly Influence the Level of Gene Expression in Plant Cells The Plant Cell*, vol. 1 (Jul. 1989) p. 671-680.

Klein et al, *Factors Influencing Gene Delivery Into Zea Mays Cells by High-Velocity Microprojectiles Bio/Technology*, vol. 6 (May 1988) pp. 559-563.

Klein et al, *Genetic Transformation of Maize Cells by Particle Bombardment Plant Physiology*, vol. 91 (1989) pp. 440-444.

Klein et al, *Transfer of foreign genes into intact maize cells with high-velocity microprojectiles Proceedings of the National Academy of Sciences, USA*, vol. 85 (Jun. 1988) pp. 4305-4309.

Koziel et al, *Field Performance of Elite Transgenic Maize Plants Expressing an Insecticidal Protein Derived from Bacillus thuringiensis Bio/Technology*, vol. 11 (Feb. 1993) pp. 194-200.

Kridl et al, *Isolation and Characterization of an Expressed Napin Gene from Brassica Rapa Seed Science Research*, vol. 1 (1991) pp. 209-219.

Lebel et al, *Functional analysis of regulatory sequences controlling PR-1 gene expression in Arabidopsis The Plant Journal*, vol. 16(2) (1998) p. 223-233.

Lim et al, *Crystal Structures of Escherichia coli Phytase and its Complex with Phytate Nature Structural Biology*, vol. 11 No. 7 (Jul. 1, 1993) pp. 811-814.

Mansson et al, *Characterization of fruit specific cDNAs from tomato Molecular & General Genetics*, vol. 200 (1985) pp. 356-361.

McCabe et al, *Stable Transformation of Soybean (Glycine Max) by Particle Acceleration Bio/Technology*, vol. 6 (Aug. 1988) pp. 923-926.

McElroy et al, *Construction of expression vectors based on the rice actin 1 (Act1) 5' region for use in monocot transformation Molecular & General Genetics*, vol. 231 (1991) pp. 150-160.

McElroy et al, *Isolation of an Efficient Actin Promoter for Use in Rice Transformation The Plant Cell*, vol. 2 (Feb. 1990) pp. 163-171.

Miksch et al, *Overexpression of the phytase from Escherichia coli and its extracellular production in bioreactors Applied Microbiology and Biotechnology*, vol. 59 (2002) pp. 685-694.

Mullaney et al, *Advances in Phytase Research Advances in Applied Microbiology*, vol. 47 (2000) p. 157-199.

Murray et al, *Codon usage in plant genes Nucleic Acids Research*, vol. 17, No. 2 (1989) pp. 477-498.

Odell et al, *Site-directed recombination in the genome of transgenic tobacco Molecular & General Genetics*, vol. 223 (1990) pp. 369-378.

Oh et al, *Catalytic Mechanism and Active Site Residues for a Phytate-Specific Thermostable Phytase from Bacillus Amyloliqufaciens DS11* Abstracts of the General Meeting of the American society for Microbiology, vol. 100, May 22, 2000.

Okamuro, J.K. and Goldberg, R.B., vol. 15 (1989) Chapter 1, "Regulation of Plant Gene Expression: General Principles" in Stumpf, P.K. and Conn, E.E. Eds, *The Biochemistry of Plants: A comprehensive treatise.* Academic Press. pp. 1-82.

Ostanin et al, *Overexpression, Site-directed Mutagenesis, and Mechanism of Escherichia coli Acid Phosphatase The Journal of Biological Chemistry*, vol. 257, No. 32 (Nov. 15, 1992) pp. 22830-22836.

Paszkowski et al, *Direct gene transfer to plants European Molecular Biology Organization Journal*, vol. 3, No. 12 (1984) pp. 2717-2722.

Pen et al, *Phytase-Containing Transgenic Seeds as a Novel Feed Additive for Improved Phosphorus Utilization Bio/Technology*, vol. 11, No. 7 (Jul. 1993) pp. 811-814.

Perlak et al, *Modification of the coding sequence enhances plant expression of insect control protein genes Proceedings of the National Academics of Science, USA*, vol. 88 (Apr. 1991) p. 3324-3328.

Riggs, C. D. and Bates, G.W., *Stable transformation of tobacco by electroporation: Evidence for plasmid concatenation Proceedings of the National Academies of Science, USA*, vol. 83 (1986) pp. 5602-5606.

Rodriguez et al, *Cloning, Sequencing, and Expression of an Escherichia coli Acid Phosphatase/Phytase Gene (appA2) Isolated from Pig Colon Biochemical and Biophysical Research Communications*, vol. 257 (1999) pp. 117-123.

Rodriguez et al, *Different Sensitivity of Recombinant Aspergillus niger Phytase (r-PhyA) and Escherichia coli pH 2.5 Acid Phosphatase (r-AppA) to Trypsin and Pepsin in Vitro Archives of Biochemistry and Biophysics*, vol. 365, No. 2 (May 15, 1999) pp. 262-267.

Rodriguez et al, *Site-Directed Mutagenesis Improves Catalytic Efficiency and Thermostability of Escherichia coli pH 2.5 Acid Phosphatase/Phytase Expressed in Pichia pastoris Archives of Biochemistry and Biophysics*, vol. 382, No. 1 (Oct. 1, 2000) pp. 105-112.

Sanford et al, *Delivery of Substances into Cells and Tissues Using a Particle Bombardment Process Particulate Science and Technology*, vol. 5 (1987) pp. 27-37.

Shimamoto et al, *Fertile transgenic rice plants generated from transformed protoplasts Nature*, vol. 338 (Mar. 16, 1989) pp. 274-276.

Slater et al, *Isolation and characterization of cDNA clones for tomato polygalacturonase and other ripening-related proteins Plant Molecular Biology*, vol. 5 (1985) pp. 137-147.

Smith et al, *Rapid appearance of an MRNA correlated with ethylene synthesis encoding a protein of molecular weight 35000 Planta*, vol. 168 (1986) pp. 94-100.

Svab et al, *Stable transformation of plastids in higher plants Proceedings of the National Academy of Sciences, USA*, vol. 87 (Nov. 1990) pp. 8526-8530.

Ugaki et al, *Replication of a geminivirus derived shuttle vector in maize endosperm Nucleic Acids Research*, vol. 19, No. 2 (1991) pp. 371-377.

Uknes et al, *Acquired Resistance in Arabidopsis The Plant Cell*, vol. 4 (Jun. 1992) pp. 645-656.

Vasil et al, *Rapid Production of Transgenic Wheat Plants by Direct Bombardment of Cultured Immature Embryos Bio/Technology*, vol. 11 (Dec. 1993) pp. 1553-1558.

Weeks et al, *Rapid Production of Multiple Independent Lines of Fertile Transgenic Wheat (Triticum aestivum) Plant Physiology*, vol. 102 (1993) pp. 1077-1084.

Wodzinski, R.J., and A.H.J. Ullah, *Phytase Advances in Applied Microbiology*, vol. 42 (1996) pp. 263-302.

Wyss et al, *Biophysical Characterization of Fungal Phytases (myo-Inositol Hexakisphosphate Phosphohydrolases): Molecular Size, Glycosylation Pattern, and Engineering of Proteolytic Resistance Applied and Environmental Microbiology*, vol. 65, No. 2 (Feb. 1999) pp. 359-366.

SEQUENCE LISTING

<160> NUMBER OF SEQ ID NOS: 4

<210> SEQ ID NO 1
<211> LENGTH: 412
<212> TYPE: PRT
<213> ORGANISM: Artificial Sequence
<220> FEATURE:
<223> OTHER INFORMATION: Nov9X Phytase

<400> SEQUENCE: 1

```
Met Ala Gln Ser Glu Pro Glu Leu Lys Leu Glu Ser Val Val Ile Val
1               5                   10                  15

Ser Arg His Gly Val Arg Ala Pro Thr Lys Ala Thr Gln Leu Met Gln
            20                  25                  30

Asp Val Thr Pro Asp Ala Trp Pro Thr Trp Pro Val Lys Leu Gly Glu
        35                  40                  45

Leu Thr Pro Arg Gly Gly Glu Leu Ile Ala Tyr Leu Gly His Tyr Trp
    50                  55                  60

Arg Gln Arg Leu Val Ala Asp Gly Leu Leu Pro Lys Cys Gly Cys Pro
65                  70                  75                  80

Gln Ser Gly Gln Val Ala Ile Ile Ala Asp Val Asp Glu Arg Thr Arg
                85                  90                  95

Lys Thr Gly Glu Ala Phe Ala Ala Gly Leu Ala Pro Asp Cys Ala Ile
            100                 105                 110

Thr Val His Thr Gln Ala Asp Thr Ser Ser Pro Asp Pro Leu Phe Asn
        115                 120                 125

Pro Leu Lys Thr Gly Val Cys Gln Leu Asp Asn Ala Asn Val Thr Asp
    130                 135                 140

Ala Ile Leu Glu Arg Ala Gly Gly Ser Ile Ala Asp Phe Thr Gly His
145                 150                 155                 160

Tyr Gln Thr Ala Phe Arg Glu Leu Glu Arg Val Leu Asn Phe Pro Gln
                165                 170                 175

Ser Asn Leu Cys Leu Lys Arg Glu Lys Gln Asp Glu Ser Cys Ser Leu
            180                 185                 190

Thr Gln Ala Leu Pro Ser Glu Leu Lys Val Ser Ala Asp Cys Val Ser
        195                 200                 205

Leu Thr Gly Ala Val Ser Leu Ala Ser Met Leu Thr Glu Ile Phe Leu
    210                 215                 220

Leu Gln Gln Ala Gln Gly Met Pro Glu Pro Gly Trp Gly Arg Ile Thr
225                 230                 235                 240

Asp Ser His Gln Trp Asn Thr Leu Leu Ser Leu His Asn Ala Gln Phe
                245                 250                 255

Asp Leu Leu Gln Arg Thr Pro Glu Val Ala Arg Ser Arg Ala Thr Pro
            260                 265                 270

Leu Leu Asp Leu Ile Lys Thr Ala Leu Thr Pro His Pro Pro Gln Lys
        275                 280                 285
```

| | | | | | | | | | | |
|---|---|---|---|---|---|---|---|---|---|---|
|Gln|Ala|Tyr|Gly|Val|Thr|Leu|Pro|Thr|Ser|Val|Leu|Phe|Ile|Ala|Gly|
| |290| | | |295| | | |300| | | | | | |

Gln Ala Tyr Gly Val Thr Leu Pro Thr Ser Val Leu Phe Ile Ala Gly
    290                 295                 300

His Asp Thr Asn Leu Ala Asn Leu Gly Gly Ala Leu Glu Leu Asn Trp
305                 310                 315                 320

Thr Leu Pro Gly Gln Pro Asp Asn Thr Pro Pro Gly Gly Glu Leu Val
                325                 330                 335

Phe Glu Arg Trp Arg Arg Leu Ser Asp Asn Ser Gln Trp Ile Gln Val
            340                 345                 350

Ser Leu Val Phe Gln Thr Leu Gln Gln Met Arg Asp Lys Thr Pro Leu
        355                 360                 365

Ser Leu Asn Thr Pro Pro Gly Glu Val Lys Leu Thr Leu Ala Gly Cys
    370                 375                 380

Glu Glu Arg Asn Ala Gln Gly Met Cys Ser Leu Ala Gly Phe Thr Gln
385                 390                 395                 400

Ile Val Asn Glu Ala Arg Ile Pro Ala Cys Ser Leu
                405                 410

<210> SEQ ID NO 2
<211> LENGTH: 60
<212> TYPE: DNA
<213> ORGANISM: Artificial Sequence
<220> FEATURE:
<223> OTHER INFORMATION: Forward Primer

<400> SEQUENCE: 2 gaagggtat ctctcgagaa aagagaggct caatctgaac cagaattgaa gttggaatct      60

<210> SEQ ID NO 3
<211> LENGTH: 42
<212> TYPE: DNA
<213> ORGANISM: Artificial Sequence
<220> FEATURE:
<223> OTHER INFORMATION: Reverse Primer

<400> SEQUENCE: 3
attattcgcg gccgcctatt acaaggaaca ggctgggatt ct                        42

<210> SEQ ID NO 4
<211> LENGTH: 1281
<212> TYPE: DNA
<213> ORGANISM: Artificial Sequence
<220> FEATURE:
<223> OTHER INFORMATION: Nov9X gene

<400> SEQUENCE: 4 gaagggtat ctctcgagaa aagagaggct caatctgaac cagaattgaa gttggaatct      60
gttgtcattg tctccagaca cggtgttaga gctccaacta aggctactca gttgatgcaa    120
gatgttactc cagatgcttg gcctacctgg cctgttaagt gggtgaatt gactccaaga    180 ggtggtgaat tgattgctta cttgggtcac tactggagac aaagattggt tgctgatggt    240
ttgttgccaa agtgtggttg tccacaatct ggtcaagttg ctatcattgc tgatgttgat    300
gaaagaacta gaaagactgg tgaagccttc gctgccggtt tggccccaga ctgtgctatc    360
actgttcaca ctcaagctga tcttcctct ccagatccat tgttcaaccc attgaagact    420
ggtgtctgtc aattggataa cgctaacgtt actgatgcca tcttggaaag agctggtggt    480
tctatcgctg acttcactgg tcactaccaa actgccttca gagaattgga aagagtcttg    540
aacttcccac aatctaactt gtgtttgaag agagagaagc aagacgaatc ttgttccttg    600

```
                                                           -continued actcaagcct tgccatctga attgaaggtc tctgctgatt gtgtctcctt gactggtgct      660
gtctccttgg cttctatgtt gactgaaatc ttcttgttgc aacaagctca aggtatgcca      720
gaaccaggtt ggggtagaat cactgattct caccaatgga acaccttgtt gtccttgcac      780
aacgctcaat tcgatttgct gcagagaact ccagaagtcg ctagatccag agctactcca      840
ttgttggact tgatcaagac cgctttgact ccacacccac cacagaagca agcttacggt      900
gttaccttgc caacttctgt cttgttcatt gccggtcacg atactaactt ggctaacttg      960
ggtggtgcct tggaattgaa ctggaccttg ccaggtcaac cagataacac tccaccaggt     1020
ggtgaattgg tcttcgaaag atggcgtcga ctgtctgata actctcaatg gattcaagtc     1080
tccttggtct tccaaacctt gcaacaaatg agagacaaga ctccattgtc cttgaacact     1140
ccaccaggtg aagtcaagtt gaccttggct ggttgtgaag aaagaaacgc tcaaggtatg     1200
tgttctttgg ctggtttcac tcaaatcgtc aacgaagcca gaatcccagc ctgttccttg     1260
taataggcgg ccgcgaataa t                                               1281
```

THERMOTOLERANT PHYTASE FOR ANIMAL FEED

RELATED APPLICATION

This application is a division of U.S. Ser. No. 10/334,671, filed Dec. 30, 2002, which claims priority to application Ser. No. 60/344,476, filed Dec. 28, 2001, which is incorporated by reference herein.

FIELD OF THE INVENTION

The present invention generally relates to the field of molecular biology, and more specifically, to methods of making and using a thermotolerant phytase.

BACKGROUND OF THE INVENTION

Phytases (myo-inositol hexakisphosphate phosphohydrolase: EC 3.1.3.8) are enzymes that hydrolyze phytate (myo-inositol hexakisphosphate) to myo-inositol and inorganic phosphate. The enzymes are known to be valuable feed additives. At the close of the twentieth century, annual sales of phytase as an animal feed additive were estimated to be $100 million and growing.

Poultry and pig diets are currently based primarily on cereals, legumes, and oilseed products. About two-thirds of phosphorus (P) present in these feedstuffs occur as phytates, the salts of phytic acid (myo-inositol hexakisphosphate, InsP6) (Jongbloed et al., 1993). Phytate phosphorus in plants is a mixed calcium-magnesium-potassium salt of phytic acid that is present as chelate and its solubility is very low (Pallauf and Rimbach, 1997). Phosphorus in this form is poorly digestible/available for monogastric animals such as human, swine, and poultry.

For the utilization of phytate phosphorus and minerals and trace elements bound in phytic acid complexes, hydrolysis of the ester-type bonded phosphate groups of phytic acid by phytase is necessary (Rimbach et al., 1994). Phytases belong to a special group of phosphatases which are capable of hydrolyzing phytate to a series of lower phosphate esters of myo-inositol and phosphate. Two types of phytases are known: 3-phytase and 6-phytase, indicating the initial attack of the susceptible phosphate ester bond. Although monogastric animals lack sufficient phytase to effectively utilize phytate phosphorous, many fungi, bacteria and yeasts produce phytase that can be used to supplement animal rations.

The beneficial effects of supplementary phytases on phosphorus digestibility and animal performance have been well documented (Mroz et al., 1994; Kornegay et al., 1996; Rao et al., 1999; Ravindran et al., 1999). However, most of these studies have been performed on an ad hoc basis with often only superficial information of the enzymes provided as marketing strategies by the manufacturers. The efficacy of any enzyme preparation depends not only on the type, inclusion rate and level of activity present, but also on the ability of the enzyme to maintain its activity in the different conditions encountered through the gastrointestinal tract and the conditions used for the pre-treatment of a food or feed formulation.

Although numerous phytases are available for use as supplements, many of the enzymes have certain disadvantages. For example, many of the currently used phytases lose activity during feed pelleting process due to heat treatment. Additionally, many of the currently used phytases are not adequate in diets containing low levels of supplemental calcium phosphate. In addition, in many instances, there is a high cost of production associated with the microbially expressed enzymes.

Thus, what is needed is a phytase with improved properties for animal feed and food processing as well as an economical procedure for producing the phytase. One method of producing a more economical phytase would be to use recombinant DNA techniques to produce transgenic plants or plant organs capable of expressing phytase which could then be added as such to animal feed or human food for direct consumption. Alternatively, the phytase could be extracted and, if desired, purified for the desired application.

SUMMARY OF THE INVENTION

Accordingly, the invention provides methods of preparing and using a nucleic acid molecule (polynucleotide) which encodes a thermotolerant phytase, i.e., a thermotolerant phytase which retains at least 40% activity after 30 minutes at about 60° C., and which has a high specific activity, i.e., at least about 200 U/mg at 37° C. and at acid pH, e.g., pH 4.5.

In one embodiment, the invention provides a method to prepare a thermotolerant phytase. The method comprises expressing in a plant host cell an expression cassette comprising a promoter operably linked to a nucleic acid molecule encoding a thermotolerant phytase which retains at least 40% activity after 30 minutes at 60° C. and has a specific activity of greater than 200 U/mg at pH 4.5 and 37° C. In a preferred embodiment, the method further comprises isolating the thermotolerant phytase. The plant host cell may be monocotyledonous, such as a maize or wheat cell or dicotyledenous, such as a soybean cell.

In a preferred embodiment, the plant cell which is employed to prepare the recombinant thermotolerant phytase yields a glycosylated form of the recombinant thermotolerant phytase.

The invention also provides a polynucleotide sequence encoding the thermotolerant phytase wherein the polynucleotide sequence is optimized for expression in a plant cell, namely a maize cell.

It is preferred that the polynucleotide that encodes the thermotolerant phytase (the first polynucleotide) is operably linked to at least one regulatory sequence, such as a promoter, an enhancer, an intron, a termination sequence, or any combination thereof, and, optionally, to a second polynucleotide encoding a signal sequence, which directs the enzyme encoded by the first polynucleotide to a particular cellular location e.g., an extracellular location. Promoters can be constitutive promoters, such as a ubiquitin promoter or inducible (conditional) promoters. Promoters may be tissue-specific. In a preferred embodiment, the promoter is an endosperm-specific promoter such as a maize γ-zein glutelin-2 promoter, and preferably the maize 27-KD γ-zein glutelin-2 promoter, or a maize ADP-glucose pyrophosphorylase promoter. The promoter may be an embryo-specific promoter such as a maize globulin 1 or maize oleosin 18 KD promoter. Exemplary promoters include, but are not limited to, SEQ ID NO:8 and SEQ ID NO:9.

Preferably, the thermotolerant phytase of the invention has at least 40% activity at about 60° C. for 30 minutes, more preferably at least 40% activity at about 65° C. for 30 minutes, even more preferably at least 35% activity at 70° C. for 30 minutes, and which has a specific activity of at least 400 U/mg, more preferably at least 600 U/mg, and even more preferably at least 800 U/mg, at 37° C. and at acid pH, e.g., less than pH 5.0 and more preferably less than pH 4.0 and greater than pH 1.5. An exemplary thermotolerant phytase of the invention is provided in SEQ ID NO: 1.

Also provided by the invention are vectors which comprise the expression cassette or polynucleotide of the invention and plant cells and transformed plant cells comprising the polynucleotide, expression cassette or vector of the invention. A vector of the invention can encode more than one polypeptide including more than one thermotolerant phytase or may encode a fusion polypeptide comprising the thermotolerant phytase of the invention, and a plant cell may comprise one or more vectors of the invention. The transformed plant cells of the invention are useful for preparing the recombinant thermotolerant phytase of the invention. Accordingly, the invention provides thermotolerant phytase isolated from the transformed plant cells of the invention, as well as synthetically prepared enzyme.

A fusion polypeptide prepared by the methods of the invention preferably comprises a signal sequence. The signal sequence, operably linked to the phytase gene, targets the phytase to an amyloplast, endoplasmic reticulum, apoplast, or starch granule of the cell. Exemplary signal sequences include, but are not limited to, the N-terminal sequence from waxy, the N-terminal sequence from γ-zein, a starch binding domain such as a waxy starch encapsulating domain. In a preferred embodiment, the fusion polypeptide prepared and employed in the methods of the invention comprises SEKDEL signal sequence operably linked to the C-terminus of the thermotolerant phytase.

The thermotolerant phytase provided by the invention has a half-life of greater than 25 minutes at a pH greater than 2.0 and less than 4.0.

Further provided by the invention are methods for formulation of thermotolerant phytases, phytase formulations or formulated enzyme mixtures. The recombinant thermotolerant phytase or formulations thereof may be added as a supplement to food or animal feed or to components of food and feed prior to, during, or after food or feed processing. Preferably, the recombinant thermotolerant phytase of the invention is added to a mixture of feed components prior to and/or during heat (e.g., steam) conditioning in a pellet mill. Thus, the invention includes methods of making and using a thermotolerant phytase.

Further, as a phytase of the invention is capable of surviving the heat conditioning step encountered in a commercial pellet mill during feed formulation, the invention provides a method of preparing animal feed, e.g., hard granular feed pellets comprising the thermotolerant phytase. To make feed, the formulated phytase may be mixed with feed components, the mixture steam conditioned in a pellet mill such that at least 50% of the pre-heat treated enzymatic activity is retained, and the feed extruded through a pellet dye. The phytase may thus be used as a supplement in animal feed by itself, in addition with vitamins, minerals, other feed enzymes, agricultural co-products (e.g., wheat middlings or corn gluten meal), or in a combination therewith. The enzyme may also be added to mash diets, i.e., diets that have not been through a pelletizer.

Because the currently available commercial phytase enzymes are not thermotolerant, they are often applied post pelleting, generally via spraying an enzyme solution onto pelleted feed. Some of the problems associated with spraying methods are that only a low percentage of the pellets are contacted with enzyme, the enzyme is only present on the surface of the coated pellets, and feed mills need to invest in and operate complex spraying machinery. In contrast, the thermotolerant phytase of the invention, which has about an 8-fold higher specific activity than other commercially available enzymes, may be added prior to pelleting, thereby facilitating production of a feed with an improved distribution of the enzyme. Moreover, feed comprising the thermotolerant phytase of the invention may have a longer shelf-life than feed sprayed with phytase, as the spraying process introduces moisture which can support fungal and bacterial growth during storage. Further, the higher specific activity of the thermotolerant phytase of the invention allows feed manufacturers to use significantly lower phosphate levels in feed. For example, it is currently recommended that diets supplemented with the available commercial phytases use a basal level of 0.45% inorganic phosphate. The thermotolerant phytase of the invention may be used with a lower phosphate supplementation, e.g., about 0.225% in poultry diets.

The invention thus provides a method of preparing animal feed comprising providing a mixture comprising one or more feed components and a preparation comprising the thermotolerant phytase of the invention, and treating the mixture under appropriate conditions of temperature and moisture so as to hydrolyze phytic acid which is present in the mixture. Also provided is animal feed prepared by such a method.

Further provided is a method of preparing a thermotolerant phytase containing composition for feed formulation comprising combining a liquid solution comprising the thermotolerant phytase of the invention and meal flour, e.g., soy meal flour, to yield a mixture; and lyophilizing the mixture to yield a lyophilized composition. In an additional embodiment, the method further comprises combining the lyophilized composition with other feed components to yield a further mixture. Lyophilized compositions prepared according to these methods are also provided by the invention.

The invention further provides a method in which a mixture comprising an animal feed component and a preparation comprising the thermotolerant phytase of the invention is treated with heat, preferably at a temperature greater than 50° C., so as to yield a heat-treated animal feed mixture. Heat-treated animal feed prepared by the method is also provided. The phytase preparation may be a liquid or a solid preparation, and preferably comprises less than about 1% inorganic phosphate. Preferably, the phytase preparation is transgenic plant material. The transgenic plant material is preferably corn grain, cracked corn, corn flour, or an enzyme extract prepared from corn.

In one embodiment, a liquid solution comprising the thermotolerant phytase of the invention is combined with soy meal flour to yield a mixture and the mixture is then lyophilized. The mixture, which preferably comprises less than 0.45% inorganic phosphate, may also comprise at least one vitamin, mineral, an enzyme other than a thermotolerant phytase, an organic acid, a probiotic product, an essential oil or a grain processing co-product. The heat-treated feed may be further processed, for example, by extruding the heat-treated feed through a pellet mill to yield pelletized animal feed, which is also encompassed by the invention.

Also provided is an animal feed composition comprising the thermotolerant phytase prepared by the methods of the invention. In particular, the invention provides an animal feed composition comprising the thermotolerant phytase, prepared according to the methods of the invention, which phytase has a specific activity of greater than 400 U/mg at pH 4.5 and 37° C., and preferably greater than 600 U/mg at pH 4.5 and 37° C., and more preferably greater than 800 U/mg at pH 4.5 and 37° C. In a preferred embodiment, the animal feed composition comprises a thermotolerant phytase which has a half-life of greater than 25 minutes at a pH greater than 2.0 and less than 4.0.

Also provided is an enzyme feed additive or a food additive comprising a thermotolerant phytase prepared according to the methods of the invention. In preferred embodiments, the feed and food additives comprise a thermotolerant phytase which has a specific activity of greater than 400 U/mg at pH 4.5 and 37° C., and preferably greater than 600 U/mg at pH 4.5 and 37° C., and more preferably greater than 800 U/mg at pH 4.5 and 37° C. In additional preferred embodiments, the animal feed and food additives comprise a thermotolerant phytase which has a half life of greater than 25 minutes at a pH greater than 2.0 and less than 4.0.

Also provided is a method of reducing/decreasing the feed conversion ratio and increasing the weight gain of an animal comprising feeding to an animal a feed comprising the thermotolerant phytase. In a preferred embodiment, the method comprises feeding to an animal a feed comprising inorganic phosphate at below 0.45% and the thermostable phytase of the invention in an amount effective to improve the feed conversion ratio or the weight gain in the animal. In additional embodiments, it is preferred that the thermostable phytase has a half-life of about 30 minutes in the digestive tract of the animal.

Further provided is a method of minimizing dietary requirements of phosphorus, e.g., inorganic phosphorous, in an animal. The method comprises feeding to an animal a feed comprising the thermotolerant phytase of the invention in an amount effective to increase the bioavailability of phosphorus, preferably the bioavailability of inorganic phosphorous, in the feed to the animal. Also provided is a method of enhancing the utilization of phosphorus present in feed for an animal, which method comprises feeding to the animal a feed comprising the thermotolerant phytase of the invention in an amount effective to increase the bioavailability of phosphorus in the feed to the animal. In additional embodiments of these methods, the phytase has a half-life of about 30 minutes in the digestive tract of the animal.

In addition, the invention provides a method of decreasing the phosphate levels in excreta from an animal comprising feeding to the animal a feed comprising the thermotolerant phytase of the invention in an amount effective to lower levels of phosphate in the excreta of the animal. In a preferred embodiment, the invention provides a method of decreasing the phosphate levels in excreta from an animal comprising feeding to the animal a feed comprising less than 0.45% inorganic phosphorus and the thermotolerant phytase of the invention in an amount effective to lower levels of phosphate in the excreta of the animal. In additional embodiments of these methods, the phytase has a half-life of about 30 minutes in the digestive tract of the animal.

The invention also provides a method of improving the nutritive value of animal feed or human food. The method comprises adding the thermotolerant phytase of the invention during the preparation of animal feed or human food. Also provided is a method of preparing human food comprising providing a mixture of a food component and a preparation comprising the thermotolerant phytase of the invention; and treating the mixture under appropriate conditions of temperature and moisture to facilitate the hydrolysis of phytic acid present in the mixture. Treated human food prepared according to this method is also encompassed by the invention. The treated human food has a reduced phytic acid content relative to the phytic acid content in corresponding human food that is not treated.

The invention also provides a method of improving the processing of grain comprising adding the thermotolerant phytase of the invention during processing of the grain. The method may be used to improve the processing of all grain, and is preferably used to improve the processing of corn, wheat, soybean, canola, or sugarcane.

The invention further provides a method of improving the nutritive value of a processed grain product or a method of processing grain comprising adding the thermotolerant phytase of the invention to the grain product during grain processing in an amount effective to improve the nutritive valued of the feed. In a preferred embodiment, the grain is corn and the grain processing method is wet milling and the products of the processing are corn gluten feed, corn gluten, and corn starch. In additional preferred embodiments, the grain is corn, wheat, soybean, canola, or sugarcane. In other preferred embodiments, the grain is an oilseed, such as soybean or canola or oilseed rape, and the processed grain product is the oilseed meal.

The invention further provides a method of preparing a thermotolerant phytase containing composition for food formulation comprising combining a liquid solution comprising the thermotolerant phytase of the invention and meal flour to yield a mixture; and lyophilizing the mixture to yield a lyophilized composition. The invention also provides a lyophilized composition prepared by such method. In a preferred embodiment, the method further comprises combining the lyophilized composition with other food components to yield a further mixture. In one preferred embodiment, the thermotolerant phytase containing composition comprises a thermotolerant phytase which has a specific activity of greater than 800 U/mg at pH 4.5 and 37° C. In another preferred embodiment, the thermotolerant phytase has a half life of greater than 25 minutes at a pH greater than 2.0 and less than 4.0 In additional aspects, the invention provides methods to prepare a transformed plant cell, plant part and plant, which express the thermotolerant phytase of the invention. The invention also encompasses the transgenic plant cell, plant part and plant produced by these methods. In preferred embodiments, the method comprises introducing into a plant cell an expression cassette comprising a promoter operably linked to a nucleic acid molecule encoding the thermotolerant phytase and obtaining a transgenic plant from the transformed plant cell. The thermotolerant phytase preferably retains at least 40% activity after 30 minutes at 60° C. and has a specific activity of greater than 200 U/mg at pH 4.5 and 37° C. More preferably, the thermotolerant phytase has a specific activity of greater than 400 U/mg at pH 4.5 and 37° C. Still more preferably, the thermotolerant phytase has a specific activity of greater than 600 U/mg at pH 4.5 and 37° C. Even more preferably, thermotolerant phytase has a specific activity of greater than 800 U/mg at pH 4.5 and 37° C.

The transformed plant cell, plant part or plant may be a dicot cell or a monocot cell, preferably a cereal cell, and more preferably a maize or wheat cell, or a soybean cell.

In preferred embodiments, the method is employed to prepare transgenic plant cell, plant part, or plant comprising the thermotolerant phytase set forth in SEQ ID NO:1. The transgenic plant cell, plant part, and plant produced therein is included within the scope of the invention.

In another preferred embodiment of the method of the invention, the thermotolerant phytase is expressed in the seed of the plant. The seed of such a plant is encompassed within the scope of the invention.

Also within the scope of this invention is a transformed plant cell, plant part, and plant comprising the expression cassette of the invention. As described previously, the expression cassette comprises a promoter operably linked to a nucleic acid molecule encoding the thermotolerant phytase of the invention. The promoter may be an embryo specific promoter, such as a maize globulin-1 promoter or a maize oleosin 18 KD promoter, and is preferably an endosperm-specific promoter, such as a maize ADP-glucose phosphorylase promoter or a maize γ-zein promoter.

The invention also encompasses a transformed plant cell, plant part and a plant comprising a nucleic acid molecule which encodes a fusion polypeptide comprising the thermotolerant phytase of the invention. In a preferred embodiment, the plant comprises a fusion polypeptide comprises a γ-zein N-terminal signal sequence operably linked to the thermotolerant phytase. In another preferred embodiment, the plant comprises a fusion polypeptide comprising SEKDEL operably linked to the C-terminus of the thermotolerant phytase. In another preferred embodiment, the plant comprises a fusion polypeptide comprising an N-terminal waxy amyloplast targeting peptide operably linked to the thermotolerant phytase. In another preferred embodiment, the plant comprises a fusion polypeptide comprising a waxy starch encapsulating domain operably linked to the C-terminus of the thermotolerant phytase.

The invention also encompasses a product of the plant of the invention, which product comprises the thermotolerant phytase. The product is preferably a seed, grain or fruit. The product may be a plant, and in particular a hybrid plant or an inbred plant. The product may also be a grain processing product comprising the thermotolerant phytase of the invention, such as the corn grain processing product and the oilseed grain processing product previously described herein or an oilseed processing product.

Animals within the scope of the invention include polygastric animals, e.g., calves, as well as monogastric animals such as swine, poultry (e.g., chickens, turkeys, geese, ducks, pheasant, grouse, quail and ostrich), equine, ovine, caprine, canine and feline, as well as fish and crustaceans. Preferred feed or animal feed prepared and/or employed in the invention include poultry and swine feed.

The levels of phytase in feed or food are preferably about 50 to 5000 U/kg, more preferably 100 to 1200 U/kg, or 300 to 1200 U/kg.

The invention also provides a transformed plant produced by the methods of the invention. Preferably, the transformed plant is a corn, wheat or soybean plant.

BRIEF DESCRIPTION OF THE FIGURES

FIG. 8A: Phytase was formulated by grinding whole transgenic corn kernels to flour. The flour was then added directly to mash feed (low phosphate) and mixed thoroughly. Animals were then fed mash diets and weight gains were determined at 21 days. Triangles: flour from corn seed containing vector pNOV4057. Diamonds: flour from corn seed containing vector pNOV4061.

FIG. 8B: Phytase formulated as milled corn was added to low phosphate chicken feed before steam conditioning and pelleting. Squares: maize flour from corn seed containing pNOV4061. Diamonds: maize flour from corn seed containing pNOV4057.

FIG. 8C: Phytase formulated as milled corn was added to low phosphate chicken feed before steam conditioning and pelleting. Corn seed containing phytase (encoded by vector pNOV4057) was milled to different average particle sizes ranging from a fine flour to a coarse grist. Diamonds, fine grind (flour); squares, medium grind, triangles, coarse grind. Coarse grind material consisted predominantly of particles >2000 microns. Medium grind material was predominantly in the size range of 500–2000 microns. Fine grind was <500 microns.

DETAILED DESCRIPTION OF THE INVENTION

I. Definitions

Figure 1:
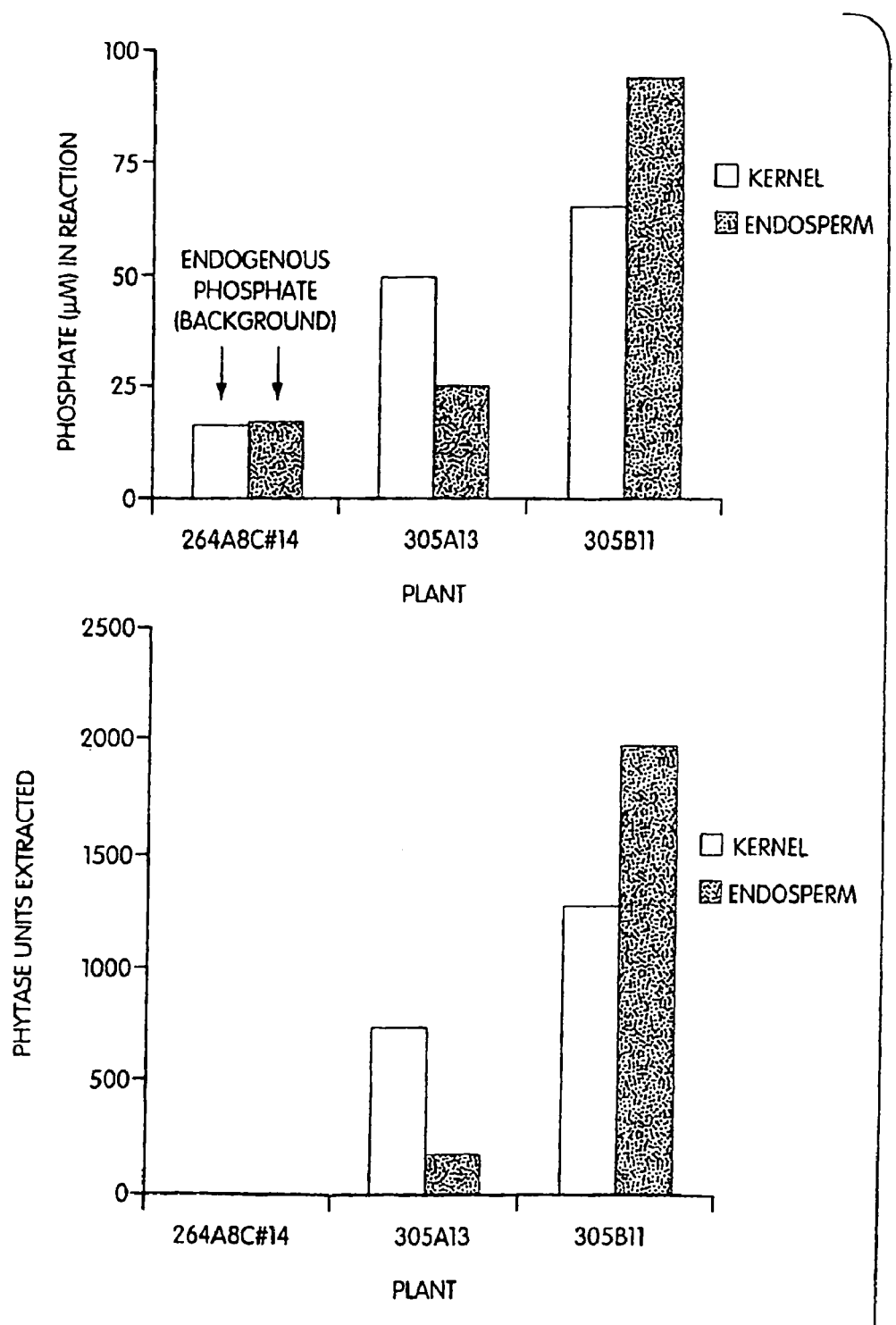
FIG. 1 demonstrates that expression of the codon optimized maize phytase gene (Nov9X) encodes a functional phytase that accumulates in maize seed. Top: each bar represents the total phosphate extracted from six kernels from plants segregating for the Nov9X transgene. Bottom: total phytase activity(background phosphate was substracted before calculating activity). 1 unit=μmol phosphate liberated/min by total extract of 6 kernels. 264A8C#14 is the negative control (lacking Nov9X transgene); 305A13 contains plasmid pNOV4057; 305B11 contains plasmid pNOV4061.

"Altered levels" refers to the level of expression in transformed or transgenic cells or organisms that differs from that of normal or untransformed cells or organisms.

The term "altered plant trait" means any phenotypic or genotypic change in a transgenic plant relative to the wild-type, non-transformed or non-transgenic plant host.

"Antisense inhibition" refers to the production of antisense RNA transcripts capable of suppressing the expression of protein from an endogenous gene or a transgene.

"Chimeric" is used to indicate that a DNA sequence, such as a vector or a gene, is comprised of more than one DNA sequences of distinct origin which are fused together by recombinant DNA techniques resulting in a DNA sequence, which does not occur naturally. The term "chimeric gene" refers to any gene that contains 1) DNA sequences, including regulatory and coding sequences, that are not found together in nature, or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature.

"Chromosomally-integrated" refers to the integration of a foreign gene or DNA construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide resistance to antibiotics such as tetracycline, hygromycin or ampicillin, or other means for selection of transformed cells.

"Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation of the RNA within the cell to create the mature mRNA that can be translated into a protein.

"Constitutive expression" refers to expression using a constitutive or regulated promoter. "Conditional" and "regulated expression" refer to expression controlled by a regulated promoter.

"Constitutive promoter" refers to a promoter that is able to express the gene that it controls in all or nearly all of the plant tissues during all or nearly all developmental stages of the plant. Each of the transcription-activating elements do not exhibit an absolute tissue-specificity, but mediate transcriptional activation in most plant parts at a level of $\geq 1\%$ of the level reached in the part of the plant in which transcription is most active.

The term "contacting" may include any method known or described for introducing a nucleic acid segment into a cell.

"Expression" refers to the transcription and/or translation of an endogenous gene or a transgene in plants. For example, in the case of antisense constructs, expression may refer to the transcription of the antisense DNA only. In addition, expression refers to the transcription and stable accumulation of sense (mRNA) or functional RNA. Expression may also refer to the production of protein.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The expression cassette comprising the nucleotide sequence of interest may be chimeric, meaning that at least one of its components is heterologous with respect to at least one of its other components. The expression cassette may also be one which is naturally occurring but has been obtained in a recombinant form useful for heterologous expression. The expression of the nucleotide sequence in the expression cassette may be under the control of a constitutive promoter or of an inducible promoter which initiates transcription only when the host cell is exposed to some particular external stimulus. In the case of a multicellular organism, the promoter can also be specific to a particular tissue or organ or stage of development.

The "expression pattern" of a promoter (with or without enhancer) is the pattern of expression levels which shows where in the plant and in what developmental stage transcription is initiated by the promoter. Expression patterns of a set of promoters are said to be complementary when the expression pattern of one promoter shows little overlap with the expression pattern of the other promoter. The level of expression of a promoter can be determined by measuring the 'steady state' concentration of a standard transcribed reporter mRNA. This measurement is indirect since the concentration of the reporter mRNA is dependent not only on its synthesis rate, but also on the rate with which the mRNA is degraded. Therefore the steady state level is the product of synthesis rates and degradation rates.

The rate of degradation can however be considered to proceed at a fixed rate when the transcribed sequences are identical, and thus this value can serve as a measure of synthesis rates. When promoters are compared in this way techniques available to those skilled in the art are hybridization SI-RNAse analysis. Northern blots and competitive RT-PCR. This list of techniques in no way represents all available techniques, but rather describes commonly used procedures used to analyze transcription activity and expression levels of mRNA.

The analysis of transcription start points in practically all promoters has revealed that there is usually no single base at which transcription starts, but rather a more or less clustered set of initiation sites, each of which accounts for some start points of the mRNA. Since this distribution varies from promoter to promoter the sequences of the reporter mRNA in each of the populations would differ from each other. Since each mRNA species is more or less prone to degradation, no single degradation rate can be expected for different reporter mRNAs. It has been shown for various eukaryotic promoter sequences that the sequence surrounding the initiation site ('initiator') plays an important role in determining the level of RNA expression directed by that specific promoter. This includes also part of the transcribed sequences. The direct fusion of promoter to reporter sequences would therefore lead to suboptimal levels of transcription.

"5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency (Turner et al., 1995).

The term "gene" is used broadly to refer to any segment of nucleic acid associated with a biological function. Thus, genes include coding sequences and/or the regulatory sequences required for their expression. For example, gene refers to a nucleic acid fragment that expresses mRNA, or specific protein, including regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

"Genetically stable" and "heritable" refer to chromosomally-integrated genetic elements that are stably maintained in the plant and stably inherited by progeny through successive generations.

"Genome" refers to the complete genetic material of an organism.

"Germline cells" refer to cells that are destined to be gametes and whose genetic material is heritable.

The terms "heterologous DNA sequence," "exogenous DNA segment" or "heterologous polynucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

"Inducible promoter" refers to those regulated promoters that can be turned on in one or more cell types by an external stimulus, such as a chemical, light, hormone, stress, or a pathogen.

The "initiation site" is the position surrounding the first nucleotide that is part of the transcribed sequence, which is also defined as position +1. With respect to this site all other sequences of the gene and its controlling regions are numbered. Downstream sequences (i.e. further protein encoding sequences in the 3' direction) are denominated positive, while upstream sequences (mostly of the controlling regions in the 5' direction) are denominated negative.

The term "intracellular localization sequence" refers to a nucleotide sequence that encodes an intracellular targeting signal. An "intracellular targeting signal" is an amino acid sequence that is translated in conjunction with a protein and directs it to a particular sub-cellular compartment. "Endoplasmic reticulum (ER) stop transit signal" refers to a carboxy-terminal extension of a polypeptide, which is translated in conjunction with the polypeptide and causes a protein that enters the secretory pathway to be retained in the ER. "ER stop transit sequence" refers to a nucleotide sequence that encodes the ER targeting signal. Other intracellular targeting sequences encode targeting signals active in seeds and/or leaves and vacuolar targeting signals.

The invention encompasses isolated or substantially purified nucleic acid or protein compositions. In the context of the present invention, an "isolated" or "purified" polynucleic acid (polynucleotide) segment or an "isolated" or "purified" polypeptide is a polynucleic acid segment or polypeptide that, by the hand of man, exists apart from its native environment and is therefore not a product of nature. An isolated polynucleic acid segment or polypeptide may exist in a purified form or may exist in a non-native environment such as, for example, a transgenic host cell. For example, an "isolated" or "purified" polynucleic acid segment or protein, or biologically active portion thereof, is substantially free of other cellular material, or culture medium when produced by recombinant techniques, or substantially free of chemical precursors or other chemicals when chemically synthesized. Preferably, an "isolated" polynucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active fragment (e.g., catalytically) thereof, is recombinantly produced, preferably culture medium represents less than about 30%, 20%, 10%, or 5% (by dry weight) of chemical precursors or non-protein-of-interest chemicals. Fragments and variants of the disclosed nucleotide sequences and proteins or partial-length proteins encoded thereby are also encompassed by the present invention. By "fragment" is intended a portion of the nucleotide sequence or a portion of the amino acid sequence, and hence a portion of the polypeptide or protein, encoded thereby.

A "marker gene" encodes a selectable or screenable trait.

The term "mature" protein refers to a post-translationally processed polypeptide without its signal peptide. "Precursor" protein refers to the primary product of translation of an mRNA. "Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide.

The term "native gene" refers to gene that is present in the genome of an untransformed cell.

"Naturally occurring" is used to describe an object that can be found in nature as distinct from being artificially produced by man. For example, a protein or nucleotide sequence present in an organism (including a virus), which can be isolated from a source in nature and which has not been intentionally modified by man in the laboratory, is naturally occurring.

Nov9X and Nov9x, are used interchangeably.

The term "polynucleotide", "nucleic acid", "polynucleic acid" or "polynucleic acid segment" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., 1991; Ohtsuka et al., 1985; Rossolini et al., 1994).

A "nucleic acid fragment" is a fraction of a given nucleic acid molecule. In higher plants, deoxyribonucleic acid (DNA) is the genetic material while ribonucleic acid (RNA) is involved in the transfer of information contained within DNA into proteins. A "genome" is the entire body of genetic material contained in each cell of an organism. The term "nucleotide sequence" refers to a polymer of DNA or RNA which can be single- or double-stranded, optionally containing synthetic, non-natural or altered nucleotide bases capable of incorporation into DNA or RNA polymers. The terms "nucleic acid" or "nucleic acid sequence" may also be used interchangeably with gene, cDNA, DNA and RNA encoded by a gene (Batzer et al., 1991; Ohtsuka et al., 1985; Rossolini et al., 1999).

Expression cassettes employed to introduce a phytase encoding open reading frame of the invention to a host cell preferably comprise a transcriptional initiation region linked to the open reading frame. Such an expression cassette may be provided with a plurality of restriction sites for insertion of the open reading frame and/or other DNAs, e.g., a transcriptional regulatory regions and/or selectable marker gene(s).

The transcriptional cassette will include in the 5'–3' direction of transcription, a transcriptional and translational initiation region, the DNA sequence of interest, and a transcriptional and translational termination region functional in plants. The termination region may be native with the transcriptional initiation region, may be native with the DNA sequence of interest, or may be derived from another source. Convenient termination regions for plant cells are available from the Ti-plasmid of *A. tumefaciens*, such as the octopine synthase and nopaline synthase termination regions. See also, Guerineau et al., 1991; Proudfoot, 1991; Sanfacon et al., 1991; Mogen et al., 1990; Munroe et al., 1990; Ballas et al., 1989; Joshi et al., 1987.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

"Operably linked" when used with respect to nucleic acid, means joined as part of the same nucleic acid molecule, suitably positioned and oriented for transcription to be initiated from the promoter. DNA operably linked to a promoter is "under transcriptional initiation regulation" of the promoter. Coding sequences can be operably-linked to regulatory sequences in sense or antisense orientation. When used with respect to polypeptides, "operably linked" means joined as part of the same polypeptide, i.e., via peptidyl bonds.

"Overexpression" refers to the level of expression in transgenic cells or organisms that exceeds levels of expression in normal or untransformed cells or organisms.

Known methods of polymerase chain reaction "PCR" include, but are not limited to, methods using paired primers, nested primers, single specific primers, degenerate primers, gene-specific primers, vector-specific primers, partially mismatched primers, and the like. See also Innis et al., 1995; and Gelfand, 1995; and Innis and Gelfand, 1999.

"Plant tissue" includes differentiated and undifferentiated tissues or plants, including but not limited to roots, stems, shoots, leaves, pollen, seeds, tumor tissue and various forms of cells and culture such as single cells, protoplast, embryos, and callus tissue. The plant tissue may be in plants or in organ, tissue or cell culture.

"Primary transformant" and "T0 generation" refer to transgenic plants that are of the same genetic generation as the tissue which was initially transformed (i.e., not having gone through meiosis and fertilization since transformation).

"Production tissue" refers to mature, harvestable tissue consisting of non-dividing, terminally-differentiated cells. It excludes young, growing tissue consisting of germline, meristematic, and not-fully-differentiated cells.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors which control the effectiveness of transcription initiation in response to physiological or developmental conditions.

Promoter elements, particularly a TATA element, that are inactive or that have greatly reduced promoter activity in the absence of upstream activation are referred to as "minimal or core promoters." In the presence of a suitable transcription factor or factors, the minimal promoter functions to permit transcription. A "minimal or core promoter" thus consists only of all basal elements needed for transcription initiation, e.g., a TATA box and/or an initiator.

The terms "protein," "peptide" and "polypeptide" are used interchangeably herein.

"Regulated promoter" refers to promoters that direct gene expression not constitutively, but in a temporally- and/or spatially-regulated manner, and include both tissue-specific and inducible promoters. It includes natural and synthetic sequences as well as sequences which may be a combination of synthetic and natural sequences. Different promoters may direct the expression of a gene in different tissues or cell types, or at different stages of development, or in response to different environmental conditions. New promoters of various types useful in plant cells are constantly being discovered, numerous examples may be found in the compilation by Okamuro et al. (1989). Typical regulated promoters useful in plants include but are not limited to safener-inducible promoters, promoters derived from the tetracycline-inducible system, promoters derived from salicylate-inducible systems, promoters derived from alcohol-inducible systems, promoters derived from glucocorticoid-inducible system, promoters derived from pathogen-inducible systems, and promoters derived from ecdysome-inducible systems.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences which may be a combination of synthetic and natural sequences. As is noted above, the term "suitable regulatory sequences" is not limited to promoters. Some suitable regulatory sequences useful with plants in the present invention will include, but are not limited to constitutive plant promoters, plant tissue-specific promoters, plant development-specific promoters, inducible plant promoters and viral promoters.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Secondary transformants" and the "T1, T2, T3, etc. generations" refer to transgenic plants derived from primary transformants through one or more meiotic and fertilization cycles. They may be derived by self-fertilization of primary or secondary transformants or crosses of primary or secondary transformants with other transformed or untransformed plants.

"Specific expression" is the expression of gene products which is limited to one or a few plant tissues (spatial limitation) and/or to one or a few plant developmental stages (temporal limitation). It is acknowledged that hardly a true specificity exists: promoters seem to be preferably switch on in some tissues, while in other tissues there can be no or only little activity. This phenomenon is known as leaky expression. However, with specific expression in this invention is meant preferable expression in one or a few plant tissues.

"Stably transformed" refers to cells that have been selected and regenerated on a selection media following transformation.

"3' non-coding sequence" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989).

"Tissue-specific promoter" refers to regulated promoters that are not expressed in all cells of an organism, e.g., not in all plant cells, but only in one or more cell types in specific organs (such as leaves or seeds), specific tissues (such as embryo or cotyledon), or specific cell types (such as leaf parenchyma or seed storage cells). These also include promoters that are temporally regulated, such as in early or late embryogenesis, during fruit ripening in developing seeds or fruit, in fully differentiated leaf, or at the onset of senescence.

"Transcription Stop Fragment" refers to nucleotide sequences that contain one or more regulatory signals, such as polyadenylation signal sequences, capable of terminating transcription. Examples include the 3' non-regulatory regions of genes encoding nopaline synthase and the small subunit of ribulose bisphosphate carboxylase.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms". Examples of methods of transformation of plants and plant cells include *Agrobacterium*-mediated transformation (De Blaere et al., 1987) and particle bombardment technology (Klein et al., 1987; U.S. Pat. No. 4,945,050), however, many other methods of transformation of cells are known to the art. Whole plants may be regenerated from transgenic cells by methods well known to the skilled artisan (see, for example, Fromm et al., 1990).

"Transformed," "transgenic," and "recombinant" refer to a host organism such as a plant into which a heterologous nucleic acid molecule has been introduced. The nucleic acid molecule can be stably integrated into the genome by methods generally known in the art which are disclosed in Sambrook et al., 1989). For example, "transformed," "transformant," and "transgenic" plants or calli have been through the transformation process and contain a foreign gene integrated into their chromosome. The term "untransformed" refers to normal plants that have not been through the transformation process.

A "transgene" refers to a gene that has been introduced into the genome by transformation and is stably maintained. Transgenes may include, for example, genes that are either heterologous or homologous to the genes of a particular plant to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but that is introduced by gene transfer.

A "transgenic plant" is a plant having one or more plant cells that contain a heterologous DNA sequence.

"Transient expression" refers to expression in cells in which a transgene is introduced, e.g., by viral infection or by such methods as *Agrobacterium*-mediated transformation, electroporation, or biolistic bombardment, but is not selected for its stable maintenance.

"Transiently transformed" refers to cells in which an expression cassette, polynucleotide or transgene has been introduced (for example, by such methods as *Agrobacterium*-mediated transformation or biolistic bombardment), but not selected for stable maintenance.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

"Translation Stop Fragment" refers to nucleotide sequences that contain one or more regulatory signals, such as one or more termination codons in all three frames, capable of terminating translation. Insertion of a translation stop fragment adjacent to or near the initiation codon at the 5' end of the coding sequence will result in no translation or improper translation. Excision of the translation stop fragment by site-specific recombination will leave a site-specific sequence in the coding sequence that does not interfere with proper translation using the initiation codon.

A polypeptide or enzyme exhibiting "phytase" activity or a "phytase" is intended to cover any enzyme capable of effecting the liberation of inorganic phosphate or phosphorous from various myo-inositol phosphates. Examples of such myo-inositol phosphates (phytase substrates) are phytic acid and any salt thereof, e.g., sodium phytate or potassium phytate or mixed salts. Also any stereoisomer of the mono-, di-, tri-, tetra- or penta-phosphates of myo-inositol may serve as a phytase substrate. In accordance with the above definition, the phytase activity can be determined using any assay in which one of these substrates is used.

A thermotolerant phytase of the invention includes variant polypeptides derived from a particular thermotolerant phytase by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the thermotolerant phytase. Such variants may result from, for example, from human manipulation. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel, 1985; Kunkel et al., 1987; U.S. Pat. No. 4,873,192; Walker and Gaastra, 1983, and the references cited therein. Guidance as to appropriate amino acid substitutions that do not affect biological activity of the protein of interest may be found in the model of Dayhoff et al., 1978, herein incorporated by reference. Conservative substitutions, such as exchanging one amino acid with another having similar properties, are preferred.

Thus, the thermotolerant phytase genes and nucleotide sequences of the invention include both the naturally occurring sequences as well as mutant forms. Likewise, the thermotolerant phytase polypeptides of the invention encompass both naturally occurring proteins as well as variations and modified forms thereof. Such variants will continue to possess the desired activity. The deletions, insertions, and substitutions of the polypeptide sequence encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays.

The nucleic acid molecules of the invention are optimized for enhanced expression in an organism of interest. For plants, see, for example, EPA035472; WO 91/16432; Perlak et al., 1991; and Murray et al., 1989. In this manner, the genes or gene fragments can be synthesized utilizing plant-preferred codons. See, for example, Campbell and Gowri, 1990 for a discussion of host-preferred codon usage. It is recognized that all or any part of the gene sequence may be optimized or synthetic. That is, synthetic or partially optimized sequences may also be used. Variant nucleotide sequences and proteins also encompass sequences and protein derived from a mutagenic and recombinogenic procedure such as DNA shuffling. With such a procedure, one or more different coding sequences can be manipulated to create a new polypeptide possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer, 1994; Stemmer, 1994; Crameri et al., 1997; Moore et al., 1997; Zhang et al., 1997; Crameri et al., 1998; and U.S. Pat. Nos. 5,605,793 and 5,837,458.

By "variants" is intended substantially similar sequences. For nucleotide sequences, variants include those sequences that, because of the degeneracy of the genetic code, encode the identical amino acid sequence of the reference protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis which encode the reference protein, as well as those that encode a polypeptide having amino acid substitutions. Generally, nucleotide sequence variants of the invention will have at least 40%, 50%, 60%, preferably 70%, more preferably 80%, even more preferably 90%, most preferably 99%, and single unit percentage identity to the native nucleotide sequence based on these classes. For example, 71%, 72%, 73% and the like, up to at least the 90% class. Variants may also include a full length gene corresponding to an identified gene fragment.

"Vector" is defined to include, inter alia, any plasmid, cosmid, phage or *Agrobacterium* binary vector in double or single stranded linear or circular form which may or may not be self transmissible or mobilizable, and which can transform prokaryotic or eukaryotic host either by integration into the cellular genome or exist extrachromosomally (e.g. autonomous replicating plasmid with an origin of replication).

Preferred Constructs of the Invention and Host Cells

The invention preferably provides an expression cassette which comprises a nucleic acid sequence (promoter) capable of directing expression of a polynucleotide encoding a thermotolerant phytase either in vitro or in vivo. As described hereinbelow, preferred polynucleotides of the invention are optimized for expression in a particular organism, e.g., a plant. Methods to prepare and/or identify a thermotolerant phytase include mutagenesis, e.g., recursive mutagenesis, and/or selection or screening, e.g., for phytases having activity at temperatures greater than 60° C. Methods for mutagenesis and nucleotide sequence alterations are well known in the art. See, for example, Kunkel, 1985; Kunkel et al., 1987; U.S. Pat. No. 4,873,192; Walker and Gaastra, 1983 and the references cited therein and Arnold et al., 1996). Once a polynucleotide encoding a thermotolerant phytase is identified, the sequence of the polynucleotide may be optimized. Methods to optimize the expression of a nucleic acid segment in a particular organism are well known in the art. Briefly, a codon usage table indicating the optimal codons used by the target organism is obtained and optimal codons are selected to replace those in the target polynucleotide and the optimized sequence is then chemically synthesized. Preferred codons for maize are described in U.S. Pat. No. 5,625,136.

DNA and Host Cells for Transformation

Vectors, plasmids, cosmids, YACs (yeast artificial chromosomes) BACs (bacterial artificial chromosomes) and DNA segments for use in transforming cells will generally comprise the phytase encoding DNA, as well as other DNA such as cDNA, gene or genes which one desires to introduce into the cells. These DNA constructs can further include structures such as promoters, enhancers, polylinkers, or even regulatory genes as desired. One of the DNA segments or genes chosen for cellular introduction will often encode a protein which will be expressed in the resultant transformed (recombinant) cells, such as will result in a screenable or selectable trait and/or which will impart an improved phenotype to the transformed cell or plant regenerated from a transformed plant cell. However, this may not always be the case, and the present invention also encompasses transformed cells and plants incorporating non-expressed transgenes.

DNA useful for introduction into cells includes that which has been derived or isolated from any source, that may be subsequently characterized as to structure, size and/or function, chemically altered, and later introduced into plants. An example of DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering. Such DNA is commonly referred to as "recombinant DNA."

Therefore useful DNA includes completely synthetic DNA, semi-synthetic DNA, DNA isolated from biological sources, and DNA derived from introduced RNA. Generally, the introduced DNA is not originally resident in the genotype which is the recipient of the DNA, but it is within the scope of the invention to isolate a gene from a given genotype, and to subsequently introduce multiple copies of the gene into the same genotype, e.g., to enhance production of a given gene product.

The introduced DNA includes, but is not limited to, DNA from plant genes, and non-plant genes such as those from bacteria, yeasts, fungi, animals or viruses. The introduced DNA can include modified or synthetic genes, portions of genes, or chimeric genes, including genes from the same or different genotype. The term "chimeric gene" or "chimeric DNA" is defined as a gene or DNA sequence or segment comprising at least two DNA sequences or segments from species which do not combine DNA under natural conditions, or which DNA sequences or segments are positioned or linked in a manner which does not normally occur in the native genome of the untransformed cell.

The introduced DNA used for transformation herein may be circular or linear, double-stranded or single-stranded. Generally, the DNA is in the form of chimeric DNA, such as plasmid DNA, that can also contain coding regions flanked by regulatory sequences which promote the expression of the recombinant DNA present in the transformed cell. For example, the DNA may itself comprise or consist of a promoter that is active in a cell which is derived from a source other than that cell, or may utilize a promoter already present in the cell that is the transformation target.

Generally, the introduced DNA will be relatively small, i.e., less than about 30 kb to minimize any susceptibility to physical, chemical, or enzymatic degradation which is known to increase as the size of the DNA increases. The number of proteins, RNA transcripts or mixtures thereof which is introduced into the cell is preferably preselected and defined, e.g., from one to about 5–10 such products of the introduced DNA may be formed.

The selection of an appropriate expression vector will depend upon the host cells. Typically an expression vector contains (1) prokaryotic DNA elements coding for a bacterial origin of replication and an antibiotic resistance gene to provide for the amplification and selection of the expression vector in a bacterial host; (2) DNA elements that control initiation of transcription such as a promoter; (3) DNA elements that control the processing of transcripts such as introns, transcription termination/polyadenylation sequence; and (4) a gene of interest that is operatively linked to the DNA elements to control transcription initiation. The expression vector used may be one capable of autonomously replicating in the above host or capable of integrating into the chromosome, originally containing a promoter at a site enabling transcription of the linked phytase gene.

If prokaryotes such as bacteria are used as the host, the expression vector for the phytase is preferably one capable of autonomously replicating in the micro-organism and comprising a promoter, a ribosome-binding sequence, the novel phytase gene, and a transcription termination sequence. The vector may also contain a gene for regulating the promoter.

A general descriptions of plant expression vectors and reporter genes can be found in Gruber et al. (1993).

Mammalian expression vectors may comprise an origin of replication, a suitable promoter and enhancer, and also any necessary ribosome binding sites, polyadenylation site, splice donor and acceptor sites, transcriptional termination sequences, and 5' flanking nontranscribed sequences.

Suitable vectors include by way of example: for bacteria, pQE70, pQE60, pQE-9 (Qiagen), pBluescript II (Stratagene), pTRC99a, pKK223-3, pDR540, pRIT2T (Pharmacia); for eukaryotic cells: pXT1, pSG5 (Stratagene) pSVK3, pBPV, pMSG, pSVLSV40 (Pharmacia). Such commercial vectors include, for example, pKK223-3 (Pharnacia Fine Chemicals, Uppsala, Sweden) and GEMI (Promega Biotec, Madison, Wis., USA). However, any other plasmid or vector may be used as long as they are replicable and viable in the host.

In certain embodiments, it is contemplated that one may wish to employ replication-competent viral vectors in monocot transformation. Such vectors include, for example, wheat dwarf virus (WDV) "shuttle" vectors, such as pW1-11 and PW1-GUS (Ugaki et al., 1991). These vectors are capable of autonomous replication in maize cells as well as E. coli, and as such may provide increased sensitivity for detecting DNA delivered to transgenic cells. A replicating vector may also be useful for delivery of genes flanked by DNA sequences from transposable elements such as Ac, Ds, or Mu. It is also contemplated that transposable elements would be useful for introducing DNA fragments lacking elements necessary for selection and maintenance of the plasmid vector in bacteria, e.g., antibiotic resistance genes and origins of DNA replication. It is also proposed that use of a transposable element such as Ac, Ds, or Mu would actively promote integration of the desired DNA and hence increase the frequency of stably transformed cells.

As representative examples of appropriate hosts, there may be mentioned: bacterial cells, such as *E. coli, Streptomyces, Bacillus subtilis*; and various species within the genera *Escherichia, Pseudomonas, Serratia, Streptomyces, Corynebacterium, Brevibacterium, Bacillus, Microbacterium*, and *Staphylococcus*, although others may also be employed as a matter of choice; fungal cells belonging to the genera *Aspergillus, Rhizopus, Trichoderma, Neurospora, Mucor, Penicillium*, etc., such as yeast belonging to the genera *Kluyveromyces, Saccharomyces, Schizosaccharomyces, Trichosporon, Schwanniomyces*, etc.; insect cells such as *Drosophila* S2 and *Spodoptera* Sf9; animal cells such as CHO, COS or Bowes melanoma, C127, 3T3, CHO, HeLa and BHK cell lines; plant cells, and the like. Any host can be used insofar as it can express the gene of interest.

The construction of vectors which may be employed in conjunction with the present invention will be known to those of skill of the art in light of the present disclosure (see, e.g., Sambrook et al., 1989; Gelvin et al., 1990).

The expression cassette of the invention may contain one or a plurality of restriction sites allowing for placement of the polynucleotide encoding a thermotolerant phytase under the regulation of a regulatory sequence. The expression cassette may also contain a termination signal operably linked to the polynucleotide as well as regulatory sequences required for proper translation of the polynucleotide. The expression cassette containing the polynucleotide of the invention may be chimeric, meaning that at least one of its components is heterologous with respect to at least one of the other components. Expression of the polynucleotide in the expression cassette may be under the control of a constitutive promoter, inducible promoter, regulated promoter, tissue-specific promoter, viral promoter or synthetic promoter.

The expression cassette may include in the 5'–3' direction of transcription, a transcriptional and translational initiation region, the polynucleotide of the invention and a transcriptional and translational termination region functional in vivo and/or in vitro. The termination region may be native with the transcriptional initiation region, may be native with the polynucleotide, or may be derived from another source.

The regulatory sequences may be located upstream (5' non-coding sequences), within (intron), or downstream (3' non-coding sequences) of a coding sequence, and influence the transcription, RNA processing or stability, and/or translation of the associated coding sequence. Regulatory sequences may include, but are not limited to, enhancers, promoters, repressor binding sites, translation leader sequences, introns, and polyadenylation signal sequences. They may include natural and synthetic sequences as well as sequences which may be a combination of synthetic and natural sequences.

The vector, used in the present invention may also include appropriate sequences for amplifying expression.

Regulatory Sequences

A promoter is a nucleotide sequence which controls the expression of a coding sequence by providing the recognition for RNA polymerase and other factors required for proper transcription. A promoter includes a minimal promoter, consisting only of all basal elements needed for transcription initiation, such as a TATA-box and/or initiator that is a short DNA sequence comprised of a TATA-box and other sequences that serve to specify the site of transcription initiation, to which regulatory elements are added for control of expression. A promoter may be derived entirely from a native gene, or be composed of different elements derived from different promoters found in nature, or even be comprised of synthetic DNA segments. A promoter may contain DNA sequences that are involved in the binding of protein factors which control the effectiveness of transcription initiation in response to physiological or developmental conditions. A promoter may also include a minimal promoter plus a regulatory element or elements capable of controlling the expression of a coding sequence or functional RNA. This type of promoter sequence contains of proximal and more distal elements, the latter elements are often referred to as enhancers.

Representative examples of promoters include, but are not limited to, promoters known to control expression of genes in prokaryotic or eukaryotic cells or their viruses. Particular bacterial promoters include *E. coli* lac or trp, the phage lambda $P_L$ promoter, lacI, lacZ, T3, T7, gpt, and lambda $P_R$. Eukaryotic promoters include CMV immediate early, HSV thymidine kinase, early and late SV40, LTRs from retrovirus, and mouse metallothionein-I. Also, an enhancer for the IE gene from human CMV may be used together with the promoter.

Any promoter capable of expressing in yeast hosts can be used as the promoter. Examples thereof include promoters for genes of hexokinase and the like in the glycolytic pathway, and promoters such as gal 1 promoter, gal 10 promoter, heat shock protein promoter, MFα-1 promoter and CUP 1 promoter.

Any promoter capable of expressing in filamentous fungi may be used. Examples are a promoter induced strongly by starch or cellulose, e.g., a promoter for glucoamylase or α-amylase from the genus *Aspergillus* or cellulase (cellobiohydrase) from the genus *Trichoderma*, a promoter for enzymes in the glycolytic pathway, such as phosphoglycerate kinase (pgk) and glycerylaldehyde 3-phosphate dehydrogenase (gpd), etc.

Within a plant promoter region there are several domains that are necessary for full function of the promoter. The first of these domains lies immediately upstream of the structural gene and forms the "core promoter region" containing consensus sequences, normally 70 base pairs immediately upstream of the gene. The core promoter region contains the characteristic CAAT and TATA boxes plus surrounding sequences, and represents a transcription initiation sequence that defines the transcription start point for the structural gene.

The presence of the core promoter region defines a sequence as being a promoter: if the region is absent, the promoter is non-functional. Furthermore, the core promoter region is insufficient to provide full promoter activity. A series of regulatory sequences upstream of the core constitute the remainder of the promoter. The regulatory sequences determine expression level, the spatial and temporal pattern of expression and, for an important subset of promoters, expression under inductive conditions (regulation by external factors such as light, temperature, chemicals, hormones).

A range of naturally-occurring promoters are known to be operative in plants and have been used to drive the expression of heterologous (both foreign and endogenous) genes in plants: for example, the constitutive 35S cauliflower mosaic virus (CaMV) promoter, the ripening-enhanced tomato polygalacturonase promoter (Bird et al., 1988), the E8 promoter (Diekman & Fischer, 1988) and the fruit specific 2A1 promoter (Pear et al., 1989) and many others.

Two principal methods for the control of expression are known, viz.: overexpression and underexpression. Overexpression can be achieved by insertion of one or more than one extra copy of the selected gene. It is, however, not unknown for plants or their progeny, originally transformed with one or more than one extra copy of a nucleotide sequence, to exhibit the effects of underexpression as well as overexpression. For underexpression there are two principle methods which are commonly referred to in the art as "antisense downregulation" and "sense downregulation" (sense downregulation is also referred to as "cosuppression"). Generically these processes are referred to as "gene silencing". Both of these methods lead to an inhibition of expression of the target gene.

Obtaining sufficient levels of transgene expression in the appropriate plant tissues is an important aspect in the production of genetically engineered crops. Expression of heterologous DNA sequences in a plant host is dependent upon the presence of an operably linked promoter that is functional within the plant host. Choice of the promoter sequence will determine when and where within the organism the heterologous DNA sequence is expressed.

Therefore, the selection of promoters for directing expression of a given transgene is critical. Promoters which are useful for plant transgene expression include those that are inducible, viral, synthetic, constitutive (Odell et al., 1985), temporally regulated, spatially regulated, tissue-specific, and spatio-temporally regulated.

Where expression in specific tissues or organs is desired, tissue-specific promoters may be used. In contrast, where gene expression in response to a stimulus is desired, inducible promoters are the regulatory elements of choice. Where continuous expression is desired throughout the cells of a plant, constitutive promoters are utilized. Additional regulatory sequences upstream and/or downstream from the core promoter sequence may be included in expression constructs of transformation vectors to bring about varying levels of expression of heterologous nucleotide sequences in a transgenic plant.

A number of plant promoters have been described with various expression characteristics. Examples of some constitutive promoters which have been described include the rice actin 1 (Wang et al., 1992; U.S. Pat. No. 5,641,876), CaMV 35S (Odell et al., 1985), CaMV 19S (Lawton et al., 1987), sucrose synthase, and the ubiquitin promoters.

Examples of tissue specific promoters which have been described include the lectin (Vodkin, 1983; Lindstrom et al., 1990), corn alcohol dehydrogenase 1 (Vogel et al., 1989; Dennis et al., 1984), corn light harvesting complex (Simpson, 1986; Bansal et al., 1992), corn heat shock protein (Odell et al., 1985), pea small subunit RuBP carboxylase (Poulsen et al., 1986; Cashmore et al., 1983), Ti plasmid mannopine synthase (Langridge et al., 1989), Ti plasmid nopaline synthase (Langridge et al., 1989), petunia chalcone isomerase (vanTunen et al., 1988), bean glycine rich protein 1 (Keller et al., 1989), truncated CaMV 35s (Odell et al., 1985), potato patatin (Wenzler et al., 1989), root cell (Yamamoto et al., 1990), maize zein (Reina et al., 1990; Kriz et al., 1987; Wandelt et al., 1989; Langridge et al., 1983; Reina et al., 1990), globulin-1 (Belanger et al., 1991), α-tubulin, cab (Sullivan et al., 1989), PEPCase (Hudspeth & Grula, 1989), R gene complex-associated promoters (Chandler et al., 1989), and chalcone synthase promoters (Franken et al., 1991).

Inducible promoters that have been described include the ABA- and turgor-inducible promoters, the promoter of the auxin-binding protein gene (Schwob et al., 1993), the UDP glucose flavonoid glycosyl-transferase gene promoter (Ralston et al., 1988), the MPI proteinase inhibitor promoter (Cordero et al., 1994), and the glyceraldehyde-3-phosphate dehydrogenase gene promoter (Kohler et al., 1995; Quigley et al., 1989; Martinez et al., 1989).

Several tissue-specific regulated genes and/or promoters have been reported in plants. These include genes encoding the seed storage proteins (such as napin, cruciferin, beta-conglycinin, and phaseolin) zein or oil body proteins (such as oleosin), or genes involved in fatty acid biosynthesis (including acyl carrier protein, stearoyl-ACP desaturase. And fatty acid desaturases (fad 2-1)), and other genes expressed during embryo development (such as Bce4, see, for example. EP 255378 and Kridl et al., 1991). Particularly useful for seed-specific expression is the pea vicilin promoter (Czako et al., 1992). (See also U.S. Pat. No. 5,625, 136, herein incorporated by reference.) Other useful promoters for expression in mature leaves are those that are switched on at the onset of senescence, such as the SAG promoter from Arabidopsis (Gan et al., 1995).

A class of fruit-specific promoters expressed at or during antithesis through fruit development, at least until the beginning of ripening, is discussed in U.S. Pat. No. 4,943,674, the disclosure of which is hereby incorporated by reference. cDNA clones that are preferentially expressed in cotton fiber have been isolated (John et al., 1992). cDNA clones from tomato displaying differential expression during fruit development have been isolated and characterized (Mansson et al., 1985, Slater et al., 1985). The promoter for polygalacturonase gene is active in fruit ripening. The polygalacturonase gene is described in U.S. Pat. No. 4,535,060, U.S. Pat. No. 4,769,061, U.S. Pat. No. 4,801,590, and U.S. Pat. No. 5,107,065, which disclosures are incorporated herein by reference.

Other examples of tissue-specific promoters include those that direct expression in leaf cells following damage to the leaf (for example, from chewing insects), in tubers (for example, patatin gene promoter), and in fiber cells (an example of a developmentally-regulated fiber cell protein is E6 (John et al., 1992). The E6 gene is most active in fiber, although low levels of transcripts are found in leaf, ovule and flower.

The tissue-specificity of some "tissue-specific" promoters may not be absolute and may be tested by one skilled in the art using the diphtheria toxin sequence. One can also achieve tissue-specific expression with "leaky" expression by a combination of different tissue-specific promoters (Beals et al., 1997). Other tissue-specific promoters can be isolated by one skilled in the art (see U.S. Pat. No. 5,589,379).

Ultimately, the most desirable DNA segments for introduction into a monocot genome may be homologous genes or gene families which encode a desired trait (e.g., hydrolysis of proteins, lipids or polysaccharides) and which are introduced under the control of novel promoters or enhancers, etc., or perhaps even homologous or tissue specific (e.g., root-, collar/sheath-, whorl-, stalk-, earshank-, kernel- or leaf-specific) promoters or control elements. Indeed, it is envisioned that a particular use of the present invention will be the targeting of a gene in a constitutive manner or in an inducible manner.

Vectors useful for use in tissue-specific targeting of genes in transgenic plants typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue; a truncated (−90 to +8) 35S promoter which directs enhanced expression in roots, an cc-tubulin gene that directs expression in roots and promoters derived from zein storage protein genes which direct expression in endosperm.

Tissue specific expression may be functionally accomplished by introducing a constitutively expressed gene (all tissues) in combination with an antisense gene that is expressed only in those tissues where the gene product is not desired. For example, a gene coding for a lipase may be introduced such that it is expressed in all tissues using the 35S promoter from Cauliflower Mosaic Virus. Expression of an antisense transcript of the lipase gene in a maize kernel, using for example a zein promoter, would prevent accumulation of the lipase protein in seed. Hence the protein encoded by the introduced gene would be present in all tissues except the kernel.

Expression of a gene in a transgenic plant may be desired only in a certain time period during the development of the plant. Developmental timing is frequently correlated with tissue specific gene expression. For example, expression of zein storage proteins is initiated in the endosperm about 15 days after pollination.

Several inducible promoters are known in the art. Many are described in a review by Gatz (1996) (see also Gatz, 1997). Examples include tetracycline repressor system, Lac repressor system, copper-inducible systems, salicylate-inducible systems (such as the PR1a system), glucocorticoid-inducible (Aoyama T. et al., 1997) and ecdysome-inducible systems. Also included are the benzene sulphonamide-inducible (U.S. Pat. No. 5364,780) and alcohol-inducible (WO 97/06269 and WO 97/06268) inducible systems and glutathione S-transferase promoters. In the case of a multicellular organism, the promoter can also be specific to a particular tissue, organ or stage of development. Examples of such promoters include, but are not limited to, the *Zea mays* ADP-gpp and the *Zea mays* γ-zein promoter.

Other studies have focused on genes inducibly regulated in response to environmental stress or stimuli such as increased salinity. Drought, pathogen and wounding (Graham et al., 1985; Graham et al., 1985, Smith et al., 1986). Accumulation of metallocarboxypeptidase-inhibitor protein has been reported in leaves of wounded potato plants (Graham et al., 1981). Other plant genes have been reported to be induced methyl jasmonate, elicitors, heat-shock, anaerobic stress, or herbicide safeners.

Regulated expression of a chimeric transacting viral replication protein can be further regulated by other genetic strategies. For example, Cre-mediated gene activation as described by Odell et al. 1990. Thus, a DNA fragment containing 3' regulatory sequence bound by lox sites between the promoter and the replication protein coding sequence that blocks the expression of a chimeric replication gene from the promoter can be removed by Cre-mediated excision and result in the expression of the trans-acting replication gene. In this case, the chimeric Cre gene, the chimeric trans-acting replication gene, or both can be under the control of tissue- and developmental-specific or inducible promoters. An alternate genetic strategy is the use of tRNA suppressor gene. For example, the regulated expression of a tRNA suppressor gene can conditionally control expression of a trans-acting replication protein coding sequence containing an appropriate termination codon as described by Ulmasov et al., 1997. Again, either the chimeric tRNA suppressor gene, the chimeric transacting replication gene, or both can be under the control of tissue- and developmental-specific or inducible promoters.

In addition to the use of a particular promoter, other types of elements can influence expression of transgenes. In particular, introns have demonstrated the potential for enhancing transgene expression. For example, Callis et al. (1987) described an intron from the corn alcohol dehydrogenase gene, which is capable of enhancing the expression of transgenes in transgenic plant cells. Similarly, Vasil et al. (1989) described an intron from the corn sucrose synthase gene having similar enhancing activity. The rice actin 1 intron, has been widely used in the enhancement of transgene expression in a number of different transgenic crops. (McElroy et al., 1991).

Other elements include those that can be regulated by endogenous or exogenous agents, e.g., by zinc finger proteins, including naturally occurring zinc finger proteins or chimeric zinc finger proteins. See, e.g., U.S. Pat. No. 5,789, 538, WO 99/48909; WO 99/45132; WO 98/53060; WO 98/53057; WO 98/53058; WO 00/23464; WO 95/19431; and WO 98/54311.

An enhancer is a DNA sequence which can stimulate promoter activity and may be an innate element of the promoter or a heterologous element inserted to enhance the level or tissue specificity of a particular promoter. An enhancer is capable of operating in both orientations (5' to 3' and 3'–5' relative to the gene of interest coding sequences), and is capable of functioning even when moved either upstream or downstream from the promoter. Both enhancers and other upstream promoter elements bind sequence-specific DNA-binding proteins that mediate their effects.

Vectors for use in accordance with the present invention may be constructed to include the ocs enhancer element. This element was first identified as a 16 bp palindromic enhancer from the octopine synthase (ocs) gene of *Agrobacterium* (Ellis et al., 1987), and is present in at least 10 other promoters (Bouchez et al., 1989). The use of an enhancer element, such as the ocs element and particularly multiple copies of the element, will act to increase the level of transcription from adjacent promoters when applied in the context of monocot transformation.

Constructs of the invention will also include the gene of interest along with a 3' end DNA sequence that acts as a signal to terminate transcription and allow for the polyadenylation of the resultant mRNA. Preferred 3' elements for plants include those from the nopaline synthase gene of *Agrobacterium tumefaciens* (Bevan et al., 1983), the terminator for the T7 transcript from the octopine synthase gene of *Agrobacterium tumefaciens*, and the 3' end of the protease inhibitor I or II genes from potato or tomato. Regulatory elements such as Adh intron 1 (Callis et al., 1987), sucrose synthase intron (Vasil et al., 1989) or TMV omega element (Gallie, et al., 1989), may further be included where desired. Convenient plant termination regions are available from the Ti-plasmid of *A. tumefaciens*, such as the octopine synthase and nopaline synthase termination regions. See also, Guerineau et al. (1991); Proudfoot (1991); Sanfacon et al. (1991); Mogen et al. (1990); Munroe et al. (1990); Ballas et al. (1989); Joshi et al. (1987).

Additionally, vectors may be constructed and employed in the intracellular targeting of a specific gene product within the cells of a transgenic plant or in directing a protein to the extracellular environment. This will generally be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed. Transit or signal peptides act by facilitating the transport of proteins through intracellular membranes, e.g., vacuole, vesicle, plastid and mitochondrial membranes, or direct proteins through the extracellular membrane. In plants, the signal sequence can target the polypeptide encoded by the polynucleotide to a specific compartment within a plant. Examples of such targets include, but are not limited to, a vacuole, endoplasmic reticulum, chloroplast, or starch granule. An example of a signal sequence includes the maize γ-zein N-terminal signal sequence for targeting to the endoplasmic reticulum and secretion into the apoplast (Torrent et al., 1997). Another signal sequence is the amino acid sequence SEKDEL for retaining polypeptides in the endoplasmic reticulum (Munro and Pelham, 1987). A polypeptide may also be targeted to the amyloplast by fusion to the waxy amyloplast targeting peptide (Klosgen et al., 1986) or to a starch granule.

For example, it may be useful to target introduced DNA to the nucleus as this may increase the frequency of transformation. Within the nucleus itself it would be useful to target a gene in order to achieve site specific integration. For example, it would be useful to have a gene introduced through transformation replace an existing gene in the cell.

As the DNA sequence between the transcription initiation site and the start of the coding sequence, i.e., the untranslated leader sequence, can influence gene expression, one may also wish to employ a particular leader sequence. Preferred leader sequences are contemplated to include those which include sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will be most preferred.

Marker Genes

In order to improve the ability to identify transformants, one may desire to employ a selectable or screenable marker gene as, or in addition to, the expressible gene of interest. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

One example of a protein suitable for modification in this manner is extensin, or hydroxyproline rich glycoprotein (HPRG). For example, the maize HPRG (Steifel et al., 1990) molecule is well characterized in terms of molecular biology, expression and protein structure. However, any one of a variety of extensins and/or glycine-rich wall proteins (Keller et al., 1989) could be modified by the addition of an antigenic site to create a screenable marker.

Selectable Markers

Possible selectable markers for use in connection with the present invention include, but are not limited to, a neo gene (Potrykus et al., 1985) which codes for kanamycin resistance and can be selected for using kanamycin, G418, and the like; a bar gene which codes for bialaphos resistance; a gene which encodes an altered EPSP synthase protein (Hinchee et al., 1988) thus conferring glyphosate resistance; a nitrilase gene such as bxn from *Klebsiella ozaenae* which confers resistance to bromoxynil (Stalker et al., 1988); a mutant acetolactate synthase gene (ALS) which confers resistance to imidazolinone, sulfonylurea or other ALS-inhibiting chemicals (European Patent Application 154,204, 1985); a methotrexate-resistant DHFR gene (Thillet et al., 1988); a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide, CTP (European Patent Application 0,218,571, 1987).

An illustrative embodiment of a selectable marker gene capable of being used in systems to select transformants are the genes that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death. The success in using this selective system in conjunction with monocots was particularly surprising because of the major difficulties which have been reported in transformation of cereals (Potrykus, 1989).

Where one desires to employ a bialaphos resistance gene in the practice of the invention, a particularly useful gene for this purpose is the bar or pat genes obtainable from species of *Streptomyces* (e.g., ATCC No. 21,705). The cloning of the bar gene has been described (Murakami et al. 1986; Thompson et al. 1987) as has the use of the bar gene in the context of plants other than monocots (De Block et al. 1987; De Block et al. 1989).

Selectable markers for use in prokaryotes include a tetracycline resistance or an ampillicin resistance gene.

Screenable Markers

Screenable markers that may be employed include, but are not limited to, a β-glucuronidase or uidA gene (GUS) which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., 1986), which allows for bioluminescence detection; or even an aequorin gene (Prasher et al., 1985), which may be employed in calcium-sensitive bioluminescence detection, or a green fluorescent protein gene (Niedz et al., 1995).

Genes from the maize R gene complex are contemplated to be particularly useful as screenable markers. The R gene complex in maize encodes a protein that acts to regulate the production of anthocyanin pigments in most seed and plant tissue. A gene from the R gene complex was applied to maize transformation, because the expression of this gene in transformed cells does not harm the cells. Thus, an R gene introduced into such cells will cause the expression of a red pigment and, if stably incorporated, can be visually scored as a red sector. If a maize line carries dominant alleles for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 which contains the rg-Stadler allele and TR112, a K55 derivative which is r-g, b, P1. Alternatively any genotype of maize can be utilized if the C1 and R alleles are introduced together. A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for populational screening for bioluminescence, such as on tissue culture plates, or even for whole plant screening.

Transformation

The expression cassette, or a vector construct containing the expression cassette, may be inserted into a cell. The expression cassette or vector construct may be carried episomally or integrated into the genome of the cell, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any vector may be used as long as it is replicable and viable in the host. If the expression cassette is introduced into a plant cell, a transformed plant cell may be grown into a transgenic plant. Accordingly, the invention provides transgenic plants and the products of the transgenic plant. Such products may include, but are not limited to, the seeds, fruit, progeny, and products of the progeny of the transgenic plant.

A variety of techniques are available and known to those skilled in the art for introduction of constructs into a cellular host. Transformation of bacteria and many eukaryotic cells may be accomplished through use of polyethylene glycol, calcium chloride, viral infection, DEAE dextran, phage infection, electroporation and other methods known in the art. Transformation of fungus may be accomplished according to Gonni et al. (1987). Introduction of the recombinant vector into yeasts can be accomplished by methods including electroporation, use of spheroplasts, lithium acetate, and the like. Any method capable of introducing DNA into animal cells can be used: for example, electroporation, calcium phosphate, lipofection and the like.

The expression cassette may be inserted into an insect cell using a baculovirus (See e.g. Baculovirus Expression Vectors, A Laboratory Manual (1992)). For example, the vector into which the recombinant gene has been introduced maybe introduced together with baculovirus into an insect cell such that a recombinant virus is obtained in the supernatant of the cultured insect cell. Insect cells are then infected with the recombinant virus whereby the protein can be expressed. The gene-introducing vector used in this method may include e.g. pLV1392, pVL1393, and pBlueBacIII (which all are products of Invitrogen). The baculovirus, may be, e.g., *Autographa californica* nuclear polyhedrosis virus, which is a virus infecting certain moth insects. The insect cells, may be ovary cells Sf9 and Sf21 from *Spodoptera frugiperda* and High 5 (Invitrogen), which is an ovary cell from *Trichoplusia ni*, etc. For co-introduction of both the vector having the recombinant gene and the baculovirus into an insect cell to prepare a recombinant virus, the calcium phosphate or lipofection methods may be used.

Methods of introducing expression vectors into plant tissue include the direct infection or co-cultivation of a plant cell with *Agrobacterium tumefaciens* (Horsch et al., 1985). Descriptions of *Agrobacterium* vector systems and methods for *Agrobacterium*-mediated gene transfer are provided by Gruber et al. (1997). Techniques for transforming plant cells include transformation with DNA employing *A. tumefaciens* or *A. rhizogenes* as the transforming agent, electroporation, DNA injection, microprojectile bombardment, particle acceleration, and the like (See, for example, EP 295959 and EP 138341).

It is particularly preferred to use the binary type vectors of Ti and Ri plasmids of *Agrobacterium* spp. Ti-derived vectors transform a wide variety of higher plants, including monocotyledonous and dicotyledonous plants, such as soybean, cotton, rape, tobacco, and rice (Pacciotti et al. 1985; Byrne et al. 1987; Sukhapinda et al. 1987; Lorz et al. 1985; Potrykus 1985; Park et al. 1985; and Hiei et al. 1994). The use of T-DNA to transform plant cells has received extensive study and is amply described (see, e.g., EP 120516; Hoekema 1985; Krauf et al. 1983 and An. et al. 1985).

Other transformation methods are available to those skilled in the art, such as direct uptake of foreign DNA constructs (see EP 295959), techniques of electroporation (Fromm et al. 1986) or high velocity ballistic bombardment with metal particles coated with the nucleic acid constructs (Kline et al. 1987, and U.S. Pat. No. 4,945,050). Once transformed, the cells can be regenerated by those skilled in the art. Of particular relevance are the recently described methods to transform foreign genes into commercially important crops, such as rapeseed (De Block et al., 1989), sunflower (Everett et al. 1987), soybean (McCabe et al. 1988; Hinchee et al. 1988; Chee et al. 1989; Christou et al. 1989; and EP 301749), rice (Hiei et al., 1994), and corn (Gordon Kamm et al. 1990; and Fromm et al., 1990).

Expression vectors containing genomic or synthetic fragments can be introduced into protoplasts or into intact tissues or isolated cells. Preferably expression vectors are introduced into intact tissue. General methods of culturing plant tissues are provided for example by Maki et al. (1993); and by Phillips et al. (1988).

Preferably, expression vectors are introduced into maize or other plant tissues using a direct gene transfer method such as microprojectile-mediated delivery, DNA injection, electroporation and the like. More preferably expression vectors are introduced into plant tissues using the microprojectile media delivery with the biolistic device. See, for example, Tomes et al. (1995).

Those skilled in the art will appreciate that the choice of method might depend on the type of plant, i.e., monocotyledonous or dicotyledonous, targeted for transformation. Suitable methods of transforming plant cells include, but are not limited to, microinjection (Crossway et al. 1986), electroporation (Riggs et al. 1986), Agrobacterium-mediated transformation (De Blaere et al. 1987; and Hinchee et al. 1988), direct gene transfer (Paszkowski et al. 1984 cite our patent), and ballistic particle acceleration using devices available from Agracetus, Inc., Madison, Wis. and BioRad, Hercules, Calif. (see, for example, Sanford et al., U.S. Pat. No. 4,945,050; and McCabe et al. 1988). Also see, Weissinger et al. 1988; Sanford et al. 1987 (onion); Christou et al., 1988 (soybean); McCabe et al. 1988 (soybean); Datta et al. 1990 (rice); Klein et al. 1988 (maize); Klein et al. 1988 (maize); Klein et al. 1988 (maize); Fromm et al. 1990 (maize); and Gordon-Kamm et al. 1990 (maize); Svab et al. 1990 (tobacco chloroplast); Koziel et al. 1993 (maize); Shimamoto et al. 1989 (rice); Christou et al. 1991 (rice); European Patent Application EP 0 332 581 (orchardgrass and other Pooideae); Vasil et al., 1993 (wheat); Weeks et al. 1993 (wheat); and Methods in Molecular Biology (1998).

Transformation of plants can be undertaken with a single DNA molecule or multiple DNA molecules (i.e., co-transformation), and both these techniques are suitable for use with the expression cassettes and constructs of the present invention. Numerous transformation vectors are available for plant transformation, and the expression cassettes of this invention can be used in conjunction with any such vectors. The selection of vector will depend upon the preferred transformation technique and the target species for transformation.

Many vectors are available for transformation using Agrobacterium tumefaciens. These typically carry at least one T-DNA border sequence and include vectors such as pBIN19. Bevan (1984). An additional vector useful for Agrobacterium-mediated transformation is the binary vector pCIB 10, which contains a gene encoding kanamycin resistance for selection in plants, T-DNA right and left border sequences and incorporates sequences from the wide host-range plasmid pRK252 allowing it to replicate in both E. coli and Agrobacterium. Its construction is described by Rothstein et al. (1987). Various derivatives of pCIB10 have been constructed which incorporate the gene for hygromycin B phosphotransferase described by Gritz et al. (1983). These derivatives enable selection of transgenic plant cells on hygromycin only (pCIB743), or hygromycin and kanamycin (pCIB715, pCIB717).

Methods using either a form of direct gene transfer or Agrobacterium-mediated transfer usually, but not necessarily, are undertaken with a selectable marker which may provide resistance to an antibiotic (e.g., kanamycin, hygromycin or methotrexate) or a herbicide (e.g., phosphinothricin). The choice of selectable marker for plant transformation is not, however, critical to the invention.

For certain plant species, different antibiotic or herbicide selection markers may be preferred. Selection markers used routinely in transformation include the nptII gene which confers resistance to kanamycin and related antibiotics (Messing & Vierra 1982; Bevan et al. 1983), the bar gene which confers resistance to the herbicide phosphinothricin (White et al. 1990, Spencer et al. 1990), the hph gene which confers resistance to the antibiotic hygromycin (Blochinger & Diggelmann), and the dhfr gene, which confers resistance to methotrexate (Bourouis et al. 1983).

One such vector useful for direct gene transfer techniques in combination with selection by the herbicide Basta (or phosphinothricin) is pCIB3064. This vector is based on the plasmid pCIB246, which comprises the CaMV 35S promoter in operational fusion to the E. coli GUS gene and the CaMV 35S transcriptional terminator and is described in WO 93/07278, herein incorporated by reference. One gene useful for conferring resistance to phosphinothricin is the bar gene from Streptomyces viridochromogenes (Thompson et al. 1987). This vector is suitable for the cloning of plant expression cassettes containing their own regulatory signals. An additional transformation vector is pSOG35 which utilizes the E. coli gene dihydrofolate reductase (DHFR) as a selectable marker conferring resistance to methotrexate.

Any plant tissue capable of subsequent clonal propagation, whether by organogenesis or embryogenesis, may be transformed with a construct of the present invention. The term organogenesis means a process by which shoots and roots are developed sequentially from meristematic centers while the term embryogenesis means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and hypocotyl meristem).

Plants of the present invention may take a variety of forms. The plants may be chimeras of transformed cells and non-transformed cells; the plants may be clonal transformants (e.g., all cells transformed to contain the expression cassette); the plants may comprise grafts of transformed and untransformed tissues (e.g., a transformed root stock grafted to an untransformed scion in citrus species). The transformed plants may be propagated by a variety of means, such as by clonal propagation or classical breeding techniques. For example, first generation (or T1) transformed plants may be selfed to give homozygous second generation (or T2) transformed plants, and the T2 plants further propagated through classical breeding techniques. A dominant selectable marker (such as npt II) can be associated with the expression cassette to assist in breeding.

The present invention may be used for transformation of any plant species, including, but not limited to, corn (Zea mays), Brassica sp. (e.g., B. napus, B. rapa, B. juncea), particularly those Brassica species useful as sources of seed oil, such as canola, alfalfa (Medicago sativa), rice (Oryza sativa), rye (Secale cereale), sorghum (Sorghum bicolor, Sorghum vulgare), millet (e.g., pearl millet (Pennisetum glaucum), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*), Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Leguminous plants include beans and peas. Beans include guar, locust bean, fenugreek, soybean, garden beans, cowpea, mungbean, lima bean, fava bean, lentils, chickpea, etc. Legumes include, but are not limited to, *Arachis*, e.g., peanuts, *Vicia*, e.g., crown vetch, hairy vetch, adzuki bean, mung bean, and chickpea, *Lupinus*, e.g., lupine, trifolium, *Phaseolus*, e.g., common bean and lima bean, *Pisum*, e.g., field bean, *Melilotus*, e.g., clover, *Medicago*, e.g., alfalfa, *Lotus*, e.g., trefoil, lens, e.g., lentil, and false indigo. Preferred forage and turf grass for use in the methods of the invention include alfalfa, orchard grass, tall fescue, perennial ryegrass, creeping bent grass, and redtop.

Preferably, plants of the present invention are crop plants, for example, corn, alfalfa, sunflower, *Brassica*, soybean, cotton, safflower, peanut, sorghum, wheat, oat, rye, millet, tobacco, barley, rice, tomato, potato, squash, melons, legume crops, e.g., pea, bean and soybean, and the like.

Recombinant Enzyme

For preparation of recombinant phytase, following transformation of a suitable host and growth of the host, a selected promoter may be induced by appropriate means (e.g., temperature shift or chemical induction) and cells cultured for an additional period to yield recombinant enzyme. Cells are then typically harvested by centrifugation, disrupted by physical or chemical means, and the resulting crude extract retained for further purification.

Cells employed in expression of proteins can be disrupted by any convenient method, including freeze-thaw cycling, sonication, mechanical disruption, or use of cell lysing agents, such methods are well known to those skilled in the art.

The enzyme can be recovered and purified from recombinant cell cultures by methods including ammonium sulfate or ethanol precipitation, acid extraction, anion or cation exchange chromatography, phospocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The enzymes of the present invention may be a product of chemical synthetic procedures, or produced by recombinant techniques from a eukaryotic host such as a higher plant.

Depending upon the host employed in a recombinant production procedure, the enzyme of the present invention may or may not be covalently modified via glycosylation. In eukaryotic cells glycosylation of secreted proteins serves to modulate protein folding, conformational and thermostability stability, and resistance to proteolysis. Given a specific application of phytase use, a glycosylated version of the enzyme may be preferable over a non-glycosylated form. For example, the use of a glycosylated phytase in animal feed helps protect the enzyme from thermal denaturation during feed pelleting and from proteolytic inactivation as it passes through the stomach of the animal, helping deliver active enzyme to the intestinal tract and site of action. For food processing applications where enzyme activity is desired only during processing and not in the final product a non-glycosylated, thermolabile, and proteolytic susceptible phytase is preferred.

Enzymes of the invention may or may not also include an initial methionine amino acid residue.

The enzyme of this invention may be employed for any purpose in which such enzyme activity is necessary or desired. In a preferred embodiment, the enzyme is employed for catalyzing the hydrolysis of phytate in animal feed. In another preferred embodiment, the enzyme is employed for catalyzing the hydrolysis of phytate in food.

Production and Characterization of Stably Transformed Plants

Transformed plant cells are placed in an appropriate selective medium for selection of transgenic cells that are then grown to callus. Shoots are grown from callus and plantlets generated from the shoot by growing in rooting medium. The various constructs normally will be joined to a marker for selection in plant cells. Conveniently, the marker may be resistance to a biocide (particularly an antibiotic, such as kanamycin, G418, bleomycin, hygromycin, chloramphenicol, herbicide, or the like). The particular marker used will allow for selection of transformed cells as compared to cells lacking the DNA which has been introduced. Components of DNA constructs, including transcription/expression cassettes of this invention, may be prepared from sequences which are native (endogenous) or foreign (exogenous) to the host. By "foreign" it is meant that the sequence is not found in the wild-type host into which the construct is introduced. Heterologous constructs will contain at least one region which is not native to the gene from which the transcription-initiation-region is derived.

To confirm the presence of the transgenes in transgenic cells and plants, a variety of assays may be performed. Such assays include, for example, "molecular biological" assays well known to those of skill in the art, such as Southern and Northern blotting, in situ hybridization and nucleic acid-based amplification methods such as PCR or RT-PCR; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated.

DNA may be isolated from cells or an organism or tissue thereof including any plant parts to determine the presence of a particular nucleic acid segment through the use of techniques well known to those skilled in the art. Note that intact sequences will not always be present, presumably due to rearrangement or deletion of sequences in the cell.

The presence of nucleic acid elements introduced through the methods of this invention may be determined by polymerase chain reaction (PCR). Using this technique discreet fragments of nucleic acid are amplified and detected by gel electrophoresis. This type of analysis permits one to determine whether a preselected nucleic acid segment is present in a stable transformant, but does not prove integration of the introduced preselected nucleic acid segment into the host cell genome. In addition, it is not possible using PCR techniques to determine whether transformants have exogenous genes introduced into different sites in the genome, i.e., whether transformants are of independent origin. It is contemplated that using PCR techniques it would be possible to clone fragments of the host genomic DNA adjacent to an introduced particular DNA segment.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced particular DNA segments in high molecular weight DNA, i.e., confirm that the introduced particular DNA segment has been integrated into the host cell genome. The technique of Southern hybridization provides information that is obtained using PCR, e.g., the presence of a particular DNA segment, but also demonstrates integration into the genome and characterizes each individual transformant.

It is contemplated that using the techniques of dot or slot blot hybridization which are modifications of Southern hybridization techniques one could obtain the same information that is derived from PCR, e.g., the presence of a particular DNA segment.

Both PCR and Southern hybridization techniques can be used to demonstrate transmission of a particular DNA segment to progeny. In most instances the characteristic Southern hybridization pattern for a given transformant will segregate in progeny as one or more Mendelian genes (Spencer et al., 1992; Laursen et al., 1994) indicating stable inheritance of the gene. The nonchimeric nature of the callus and the parental transformants ($R_0$) was suggested by germline transmission and the identical Southern blot hybridization patterns and intensities of the transforming DNA in callus, $R_0$ plants and $R_1$ progeny that segregated for the transformed gene.

Whereas DNA analysis techniques may be conducted using DNA isolated from any part of a plant, RNA may only be expressed in particular cells or tissue types and hence it will be necessary to prepare RNA for analysis from these tissues. PCR techniques may also be used for detection and quantitation of RNA produced from introduced particular DNA segments. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

Thus, while Southern blotting and PCR may be used to detect the particular DNA segment in question, they do not provide information as to whether the particular DNA segment is being expressed. Expression may be evaluated by specifically identifying the protein products of the introduced particular DNA segments or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures may also be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed.

Very frequently the expression of a gene product is determined by evaluating the phenotypic results of its expression. These assays also may take many forms including but not limited to analyzing changes in the chemical composition, morphology, or physiological properties of the plant Phytase Compositions Generally, phytase compositions are liquid or dry.

Liquid compositions need not contain anything more than the phytase enzyme, preferably in a highly purified form. However, a stabilizer such as glycerol, sorbitol or mono propylen glycol may be added. The liquid composition may also comprise other additives, such as salts, sugars, preservatives, pH-adjusting agents, proteins, and phytate (a phytase substrate). Typical liquid compositions are aqueous or oil-based slurries. The liquid compositions may be added to a food or feed before or after an optional pelleting thereof.

Dry compositions may be freeze-dried or spray dried compositions, in which case the composition need not contain anything more than the enzyme in a dry form Dry compositions may be granulates which may readily be mixed with, e.g., food or feed components, or more preferably, form a component of a pre-mix. The particle size of the enzyme granulates preferably is compatible with that of the other components of the mixture. This provides a safe and convenient means of incorporating enzymes into, e.g., processed food or animal feed.

For example, a stable phytase enzyme formulation can be prepared by freezing a mixture of liquid enzyme solution with a bulking agent such as ground soybean meal, and then lyophilizing the mixture. The reduction in moisture and the binding interactions of the phytase with the bulking agent protect the enzyme from external environmental factors such as the temperature extremes experienced during compound feed manufacture. Dry formulations can further enhance stability by minimizing the activity of potential proteolytic enzymes that may be present as by-products in the liquid fermentation mixture used to manufacture the target enzyme. The resulting dry enzyme-soy flour mixture can withstand high extremes of temperature. For example, after 120 minutes of heating at 96° C., the dry enzyme formulation retained 97.8% of its original enzymatic activity. The formulated enzyme mixture can be used as a feed supplement for use in poultry and swine production. For instance, addition of 500 enzyme units of a thermotolerant phytase of the invention to 1 kg of a standard corn-soy poultry diet will allow a reduction in the levels of inorganic phosphate supplementation currently used in animal nutrition, i.e., from 0.45% to 0.225%. Chickens raised on a 0.225% phosphate diet supplemented with the formulated phytase will perform as well as chickens fed a standard diet containing 0.45% phosphate. Moreover, a reduction in phosphate supplementation results in decreased levels of phosphate pollution, which in turn significantly lessens the environmental impact of intensive commercial animal production.

Potential drawbacks with using small particle size dry formulations are their dust forming tendencies and the high local concentration of the target enzyme on the surface of the particles. Dust particles impregnated with enzyme protein may pose an immunological concern, while localization of enzyme predominately on the surface of the small particles may affect stability, particularly during prolonged period of storage and during feed manufacture.

Thus, further provided by the invention is a non-manufactured method of formulation, which comprises producing and delivering the target enzyme of the invention in grain such as maize, wheat, or soy. The intact grain protects the target enzyme from external environmental factors and minimizes the production of dust. This method of enzyme delivery adds significant savings to a formulation cost, particularly when compared to the cost of low-dust granulate formulations currently used commercially. The grain-containing enzyme may be added to animal feed in the form of cracked seed, ground seed, or in a more refined form. Alternatively, a protein extract may be made from seed, and that extract can be further processed into either a stabilized liquid or into a dry state by lyophilization or spray drying. For example, enzymatically active phytase can be produced in maize at a level of 1,000,000 units per kg of seed, and active enzyme is recoverable from the seed by aqueous extraction.

Agglomeration granulates are prepared using agglomeration techniques in a high shear mixer during which a filler material and the enzyme are co-agglomerated to form granules. Absorption granulates are prepared by having cores of a carrier material to absorb/be coated by the enzyme.

Typical filler materials are salts such as disodium sulphate. Other fillers include kaolin, talc, magnesium aluminium silicate and cellulose fibres. Optionally, binders such as dextrins are also included in agglomeration granulates.

Typical carrier materials include starch, e.g., in the form of cassava, corn, potato, rice and wheat. Salts may also be used.

Optionally, the granulates are coated with a coating mixture. Such a mixture comprises coating agents, preferably hydrophobic coating agents, such as hydrogenated palm oil and beef tallow, and if desired, other additives such as calcium carbonate or kaolin.

Additionally, phytase compositions may contain other substituents such as coloring agents, aroma compounds, stabilizers, vitamins, minerals, other feed or food enhancing enzymes etc. This is so in particular for the so-called pre-mixes.

A "food or feed additive" is an essentially pure compound or a multi component composition intended for or suitable for being added to food or feed. In particular it is a substance that by its intended use is becoming a component of a food or feed product or affects any characteristics of a food or feed product. Thus, a phytase additive is understood to mean a phytase which is not a natural constituent of the main feed or food substances or is not present at its natural concentration therein, e.g., the phytase is added to the feed separately from the feed substances, alone or in combination with other feed additives, or the phytase is an integral part of one of the feed substances but has been produced therein by recombinant DNA technology. A typical additive usually comprises one or more compounds such as vitamins, minerals or feed enhancing enzymes and suitable carriers and/or excipients.

A ready for use phytase additive is herein defined as an additive that is not produced in situ in animal feed or in processed food. A ready for use phytase additive may be fed to humans or animals directly or, preferably, directly after mixing with other feed or food constituents. For example, a feed additive according to this aspect of the present invention is combined with other feed components to produce feed. Such other feed components include one or more other (preferably thermostable) enzyme supplements, vitamin feed additives, mineral feed additives and amino acid feed additives. The resulting (combined) feed additive including possibly several different types of compounds can then be mixed in an appropriate amount with the other feed components such as cereal and protein supplements to form an animal feed. Processing of these components into an animal feed can be performed using any of the currently used processing apparatuses such as a double-pelleting machine, a steam pelleter, an expander or an extruder.

Similarly, a food additive according to this aspect of the present invention is combined with other food components to produce processed food products. Such other food components include one or more other (preferably thermostable) enzyme supplements, vitamin food additives and mineral food additives. The resulting (combined) food additive, including possibly several different types of compounds can then be mixed in an appropriate amount with the other food components such as cereal and plant proteins to form a processed food product. Processing of these components into a processed food product can be performed using any of the currently used processing apparatuses.

In a preferred embodiment, the phytase compositions of the invention additionally comprises an effective amount of one or more feed or food enhancing enzymes, in particular feed or food enhancing enzymes selected from the group consisting of α-galactosidases, β-galactosidases, in particular lactases, other phytases, β-glucanases, in particular endo-β-1,4-glucanases and endo-β-1,3(4)-glucanases, cellulases, xylosidases, galactanases, in particular arabinogalactan endo-1,4-β-galactosidases and arabinogalactan endo-1,3-β-galactosidases, endoglucanases, in particular endo-1,2-β-glucanase, endo-1,3-α-glucanase, and endo-1,3-β-glucanase, pectin degrading enzymes, in particular pectinases, pectinesterases, pectin lyases, polygalacturonases, arabinanases, rhamnogalacturonases, rhamnogalacturonan acetyl esterases, rhamnogalacturonan-α-rhamnosidase, pectate lyases, and α-galacturonisidases, mannanases, β-mannosidases, mannan acetyl esterases, xylan acetyl esterases, proteases, xylanases, arabinoxylanases and lipolytic enzymes such as lipases, phospholipases and cutinases.

The animal feed additive of the invention is supplemented to the animal before or simultaneously with the diet. Preferably, the animal feed additive of the invention is supplemented to the animal simultaneously with the diet.

An effective amount of phytase in food or feed is from about 10 to 20,000 FTU/kg; preferably from about 10 to 15,000 FTU/kg, more preferably from about 10 to 10,000 FTU/kg, in particular from about 100 to 5,000 FTU/kg, especially from about 100 to about 2,000 FTU/kg feed or food.

Also within the scope of this invention is the use of phytase for processing and manufacturing human foods and animal feeds. Grains and flours destined for human foods can be enzymatically treated with phytase to reduce the phytin content of the material. The reduced levels of phytin enhance the quality of the food by increasing the nutrient availability of essential minerals such as iron, calcium, and zinc. In addition to increasing the nutritional quality of food, phytase used during food processing can improve the overall efficiency of the food production method. For example, addition of phytase to white soybean flakes during soy protein isolate manufacturing can significantly increase the yield and quality of extractable protein. During food manufacture the phytase is active during manufacture and processing only, and is not active in the final food product. This aspect is relevant for instance in dough making and baking. Similarly, animal feed grain, such as toasted soybean meal or canola meal, may be pre-processed with phytase prior to compound feed manufacture. Removal of the anti-nutritive factors in animal feed components prior to compound feed manufacture produces a nutritionally higher quality and more valuable animal feed ingredient. In this processing method the phytase is active during feed manufacturing, and may or may not be active in the digestive tract of the animal upon ingestion of the treated feed.

In addition to using phytase as a food processing aid, the scope of this invention encompasses the use of phytase as a human supplemental digestive aid. Phytase in tablet form can be ingested at the time of food consumption to deliver active enzyme to the gastrointestinal tract of the recipient. Nutritional gains for the consumer would be experienced in vivo and may be taken with foods that cannot be treated with a phytase during food processing.

Also within the scope of the invention is the use of a phytase of the invention during the preparation of food or feed preparations or additives, i.e., the phytase is active during the manufacture only and is not active in the final food or feed product. This aspect is particularly relevant, for instance, in dough making and baking and the production of other ready-to-eat cereal based products.

Another possibility for the exogenous addition of phytase to animal feed and processed food is to add phytase-containing transgenic plant material to the feed, preferably processed transgenic seed, in which the phytase has been synthesized through heterologous gene expression. The parts of the plants which express the heterologous phytase, e.g., the seed of the transgenic plants or other plant materials such as roots, stems, leaves, wood, flowers, bark, and/or fruit may be included in animal feed, either as such or after further processing. In a cereal-based feed or food, the cereal is preferably wheat, barley, maize, sorghum, rye, oats, triticale or rice. The phytase may also be used advantageously in monogastrics as well as in polygastrics, especially young calves. Diets for fish and crustaceans may also be supplemented with phytase to further improve feed conversion ratio and reduce the level of excreted phosphorus for intensive production systems. The feed according to the present invention may also be provided to animals such as poultry, e.g., turkeys, geese, ducks, as well as swine, equine, bovine, ovine, caprine, canine and feline, as well as fish and crustaceans. It is however particularly preferred that the feed is provided to pigs or to poultry, including, but not limited to, broiler chickens, hens, in particular laying hens, turkeys and ducks.

Feed Compositions and Methods of Use

The phytases (formulated as described above) of the current invention may be combined with other ingredients to result in novel feed compositions with particular advantages.

For instance, it is preferable that intensive animal production operations limit the phosphate pollution that is contained in the feces of the animals that are produced. The amount of phosphate present in the diet and the availability of the phosphate in the diet to the animal are the primary factors influencing the excreted phosphate present in the feces of the animal. Currently, the availability of the plant, or grain-derived phosphate, present in soybean meal, corn grain (and other feedstuffs) is low as the phosphate is primarily in the form of phytic acid. In order to maximize the growth efficiencies of the animals inorganic phosphate is added to feed resulting in a feed composition that contains adequate levels of available phosphate. However, these feed formulations contain too much total phosphate and result in phosphate pollution.

Although commercially available phytases at present result in higher phosphate availability they are recommended to be used with high levels of added inorganic phosphate. The phytases of the present invention are so active that they can be used to create novel animal feed formulations that have a) significantly reduced levels of inorganic phosphate, and b) allow superior feed conversion efficiency and improved weight gain relative to normal diets. At present, commercially available phytases will not allow animals to be efficiently produced on a feed that contains no added inorganic phosphorus Specifically, the animal feed of the invention comprises the combination of a phytase of the present invention in combination with animal feed ingredients to form a feed that has substantially lowered inorganic phosphorus levels. In a preferred embodiment, the feed compositions of the invention comprises typical feed ingredients, micronutrients, vitamins, etc. and an effective amount of thermostable phytase and inorganic phosphate where the amounts of the phytase and phosphorus are from about between the levels of 50–20,000 units of phytase per kg of feed and less than 0.45% inorganic phosphorus; preferably between the levels of 100–10,000 units of phytase per kg of feed and less than 0.225% inorganic phosphorus; in particular between the levels of 150–10,000 units of phytase per kg of feed and less than 0.15% inorganic phosphorus, or especially between the levels of 250–20,000 units of phytase per kg of feed and no exogenously added inorganic phosphorus.

Also, within the scope of the invention are methods of improving weight gains, and feed conversions ratios (FCR) associated with production of farm animals. A phytase of the present invention allows improved weight gains and FCR especially when used in combination with diets that are low in inorganic phosphate. Specifically the method of the present invention to improve the FCR, or weight gain of a low inorganic phosphate diet by feeding a diet to an animal comprising a phytase of the present invention and a level of inorganic phosphate at or below the level of 0.45%. Preferably, the method comprises feeding a diet containing the phytase and less than 0.225% inorganic phosphate, or most preferably the method comprises feeding a diet containing the phytase and no added inorganic phosphorus.

The animal feed of the present invention can be used on monogastric or polygastric animals. The animal feed of the present invention can be feed for poultry, or swine, or calves, or companion animals such as dogs or cats or horsed. Examples of such feed and the use of the feed are provided in Example 3.

The present invention also provides for a method of animal husbandry that results in a significantly reduced environmental phosphate load. The method comprises feeding entire flocks or herds of farm animals a feed composition containing a phytase of the present invention and a reduced amount of inorganic phosphorus (less than 0.45%). More preferably the method comprises feeding entire flocks or herds of farm animals a feed composition containing a phytase of the present invention and a significantly reduced amount of inorganic phosphorus (less than 0.225%), or most preferably the method comprising feeding entire flocks or herds of farm animals a feed composition containing a phytase of the present invention and no inorganic phosphorus. This method will allow high densities of animals to be maintained while minimizing the environmental release of phosphate from the farming operation.

Methods Useful for the Invention

I. Expression Cassettes Useful for the Invention

Coding sequences intended for expression in transgenic plants are first assembled in expression cassettes 3' to a suitable promoter expressible in plants. The expression cassettes may also comprise any further sequences required or selected for the expression of the transgene. Such sequences include, but are not restricted to, transcription terminators, extraneous sequences to enhance expression such as introns, vital sequences, and sequences intended for the targeting of the gene product to specific organelles and cell compartments. These expression cassettes can then be transferred to the plant transformation vectors described herein.

The following is a description of various components of typical expression cassettes.

A. Promoters

Selection of the promoter to be used in expression cassettes will determine the spatial and temporal expression pattern of the transgene in the transgenic plant. Selected promoters will express transgenes in specific cell types (such as leaf epidermal cells, mesophyll cells, root cortex cells) or in specific tissues or organs (roots, leaves or flowers, for example) and selection should reflect the desired location of accumulation of the gene product. Alternatively, the selected promoter may drive expression of the gene under various inducing conditions. Promoters vary in their strength, i.e., ability to promote transcription. Depending upon the host cell system utilized, any one of a number of suitable promoters can be used, including the gene's native promoter. The following are non-limiting examples of promoters that may be used in the expression cassettes employed in the present invention.

Constitutive Promoters a. Ubiquitin Promoters

Ubiquitin is a gene product known to accumulate in many cell types and its promoter has been cloned from several species for use in transgenic plants (e.g. sunflower—Binet et al. Plant Science 79: 87–94 (1991); maize—Christensen et al. Plant Molec. Biol. 12: 619–632 (1989); and *Arabidopsis*—Norris et al., *Plant Mol. Biol.* 21:895–906 (1993)). The maize ubiquitin promoter has been developed in transgenic monocot systems and its sequence and vectors constructed for monocot transformation are disclosed in the patent publication EP 0 342 926 (to Lubrizol), which is herein incorporated by reference. Taylor et al. (Plant Cell Rep. 12: 491–495 (1993)) describe a vector (pAHC25) that comprises the maize ubiquitin promoter and first intron and its high activity in cell suspensions of numerous monocotyledons when introduced via microprojectile bombardment. The *Arabidopsis* ubiquitin promoter is ideal for use with the nucleotide sequences of the present invention. The ubiquitin promoter is suitable for gene expression in transgenic plants, both monocotyledons and dicotyledons. Suitable vectors include derivatives of pAHC25 or any of the transformation vectors described in this application. The vectors may be modified by introducing of the appropriate ubiquitin promoter and/or intron sequences.

b. The CaMV 35S Promoter

Construction of the plasmid pCGN1761 is described in published patent application EP 0 392 225 (published Sep. 25, 1991; Ciba Geigy; Example 23), which is hereby incorporated by reference. The plasmid contains the "double" CaMV 35S promoter and the tml transcriptional terminator with a unique EcoRI site between the promoter and the terminator and has a pUC-type backbone. A derivative of pCGN1761 is constructed which has a modified polylinker which includes NotI and XhoI sites in addition to the existing EcoRI site. This derivative, designated pCGN1761ENX and is useful for the cloning of cDNA sequences or coding sequences (including microbial ORF sequences) within its polylinker for the purpose of their expression under the control of the 35S promoter in transgenic plants. The entire 35S promoter-coding sequence-tml terminator cassette of such a construction can be excised by HindIII, SphI, SalI, and XbaI sites 5' to the promoter and XbaI, BamHI and BglI sites 3' to the terminator for transfer to transformation vectors such as those described below. Furthermore, the double 35S promoter fragment can be removed by 5' excision with HindIII, SphI, SalI, XbaI, or PstI, and 3' excision with any of the polylinker restriction sites (EcoRI, NotI or XhoI) for replacement with another promoter. If desired, modifications around the cloning sites can be made by the introduction of sequences that may enhance translation. This is particularly useful when overexpression is desired. For example, pCGN1761ENX may be modified by optimization of the translational initiation site as described in Example 37 of U.S. Pat. No. 5,639,949 (issued Jun. 17, 1997 to Ciba Geigy), incorporated herein by reference.

c. The Actin Promoter:

Several isoforms of actin are known to be expressed in most cell types and consequently the actin promoter is a good choice for a constitutive promoter. In particular, the promoter from the rice ActI gene has been cloned and characterized (McElroy et al. Plant Cell 2: 163–171 (1990)). A 1.3 kb fragment of the promoter was found to contain all the regulatory elements required for expression in rice protoplasts. Furthermore, numerous expression vectors based on the ActI promoter have been constructed specifically for use in monocotyledons (McElroy et al. Mol. Gen. Genet. 231: 150–160 (1991)). These incorporate the ActI-intron 1, AdhI 5' flanking sequence and AdhI-intron 1 (from the maize alcohol dehydrogenase gene) and sequence from the CaMV 35S promoter. Vectors showing highest expression were fusions of 35S and ActI intron or the ActI 5' flanking sequence and the ActI intron. Optimization of sequences around the initiating ATG (of the GUS reporter gene) also enhanced expression. The promoter expression cassettes described by McElroy et al. (Mol. Gen. Genet. 231: 150–160 (1991)) can be easily modified for gene expression and are particularly suitable for use in monocotyledonous hosts. For example, promoter-containing fragments may be removed from the McElroy constructions and used to replace the double 35S promoter in pCGN1761ENX, which is then available for the insertion of specific gene sequences. The fusion genes thus constructed may then be transferred to appropriate transformation vectors. In a separate report, the rice ActI promoter with its first intron has also been found to direct high expression in cultured barley cells (Chibbar et al. Plant Cell Rep. 12: 506–509 (1993)).

Inducible Expression a. PR-1 Promoters:

The double 35S promoter in pCGN1761ENX may be replaced with any other promoter of choice that will result in suitably high expression levels. By way of example, one of the chemically regulatable promoters described in U.S. Pat. No. 5,614,395 (issued Mar. 25, 1997 to Ciba Geigy), such as the tobacco PR-1a promoter, may replace the double 35S promoter. Alternately, the Arabidopsis PR-1 promoter described in Lebel et al., *Plant J.* 16:223–233 (1998) may be used. The promoter of choice is preferably excised from its source by restriction enzymes, but can alternatively be PCR-amplified using primers that carry appropriate terminal restriction sites. Should PCR-amplification be undertaken, then the promoter should be re-sequenced to check for amplification errors after the cloning of the amplified promoter in the target vector. The chemically/pathogen regulatable tobacco PR-1a promoter is cleaved from plasmid pCIB1004 (for construction, see example 21 of EP 0 332 104 (published Mar. 20, 1991; Ciba Geigy), which is hereby incorporated by reference) and transferred to plasmid pCGN1761ENX (Uknes et al., *Plant Cell* 4: 645–656 (1992)). The plasmid pCIB1004 is cleaved with NcoI and the resultant 3' overhang of the linearized fragment is rendered blunt by treatment with T4 DNA polymerase. The fragment is then cleaved with HindIII and the resultant PR-1a promoter-containing fragment is gel purified and cloned into pCGN1761ENX from which the double 35S promoter has been removed. This is done by cleavage with XhoI and blunting with T4 polymerase, followed by cleavage with HindIII and isolation of the larger vector-terminator containing fragment into which the pCIB1004 promoter fragment is cloned. This generates a pCGN1761ENX derivative with the PR-1a promoter and the tml terminator and an intervening polylinker with unique EcoRI and NotI sites. The selected coding sequence can be inserted into this vector, and the fusion products (i.e. promoter-gene-terminator) can subsequently be transferred to any selected transformation vector, including those described infra. Various chemical regulators may be employed to induce expression of the selected coding sequence in the plants transformed according to the present invention, including the benzothiadiazole, isonicotinic acid, and salicylic acid compounds disclosed in U.S. Pat. Nos. 5,523,311 and 5,614,395.

b. Ethanol-Inducible Promoters

A promoter inducible by certain alcohols or ketones, such as ethanol, may also be used to confer inducible expression of a coding sequence of the present invention. Such a promoter is, for example, the alcA gene promoter from *Aspergillus nidulans* (Caddick et al. (1998) *Nat. Biotechnol* 16:177–180). In *A. nidulans*, the alcA gene encodes alcohol dehydrogenase I, the expression of which is regulated by the AlcR transcription factors in presence of the chemical inducer. For the purposes of the present invention, the CAT coding sequences in plasmid palcA:CAT comprising a alcA gene promoter sequence fused to a minimal 35S promoter (Caddick et al. (1998) *Nat. Biotechnol* 16:177–180) are replaced by a coding sequence of the present invention to form an expression cassette having the coding sequence under the control of the alcA gene promoter. This is carried out using methods well known in the art.

c. Glucocorticoid-Inducible Promoter:

Induction of expression of a nucleic acid sequence of the present invention using systems based on steroid hormones is also contemplated. For example, a glucocorticoid-mediated induction system is used (Aoyama and Chua (1997) *The Plant Journal* 11: 605–612) and gene expression is induced by application of a glucocorticoid, such as a synthetic glucocorticoid, preferably dexamethasone, preferably at a concentration ranging from 0.1 mM to 1 mM, more preferably from 10 mM to 100 mM. For the purposes of the present invention, the luciferase gene sequences are replaced by a nucleic acid sequence of the invention to form an expression cassette having a nucleic acid sequence of the invention under the control of six copies of the GAL4 upstream activating sequences fused to the 35S minimal promoter. This is carried out using methods well known in the art. The trans-acting factor comprises the GALA DNA-binding domain (Keegan et al. (1986) *Science* 231: 699–704) fused to the transactivating domain of the herpes viral protein VP16 (Triezenberg et al. (1988) *Genes Devel.* 2: 718–729) fused to the hormone-binding domain of the rat glucocorticoid receptor (Picard et al. (1988) *Cell* 54: 1073–1080). The expression of the fusion protein is controlled by any promoter suitable for expression in plants known in the art or described here. This expression cassette is also comprised in the plant comprising a nucleic acid sequence of the invention fused to the 6×GAL4/minimal promoter. Thus, tissue- or organ-specificity of the fusion protein is achieved leading to inducible tissue- or organ-specificity of the expression cassettes of the present invention.

d. Wound-Inducible Promoters:

Wound-inducible promoters may also be suitable for gene expression. Numerous such promoters have been described (e.g. Xu et al. Plant Molec. Biol. 22: 573–588 (1993), Logemann et al. Plant Cell 1: 151–158 (1989), Rohrmeier & Lehle, Plant Molec. Biol. 22: 783–792 (1993), Firek et al. Plant Molec. Biol. 22: 129–142 (1993), Warner et al. Plant J. 3: 191–201 (1993)) and all are suitable for use with the instant invention. Logemann et al. describe the 5' upstream sequences of the dicotyledonous potato wunI gene. Xu et al. show that a wound-inducible promoter from the dicotyledon potato (pin2) is active in the monocotyledon rice. Further, Rohrmeier & Lehle describe the cloning of the maize WipI cDNA which is wound induced and which can be used to isolate the cognate promoter using standard techniques. Similar, Firek et al. and Warner et al. have described a wound-induced gene from the monocotyledon *Asparagus officinalis*, which is expressed at local wound and pathogen invasion sites. Using cloning techniques well known in the art, these promoters can be transferred to suitable vectors, fused to the genes pertaining to this invention, and used to express these genes at the sites of plant wounding.

3. Tissue-Specific Expression a. Root Specific Expression:

Another pattern of gene expression is root expression. A suitable root promoter for the constructs and methods of the present invention is the promoter of the maize metallothionein-like (MTL) gene described by de Framond (FEBS 290: 103–106 (1991)) and also in U.S. Pat. No. 5,466,785 (issued Nov. 14, 1995 to Ciba Geigy), incorporated herein by reference. This "MTL" promoter is transferred to a suitable vector such as pCGN1761ENX for the insertion of a selected gene and subsequent transfer of the entire promoter-gene-terminator cassette to a transformation vector of interest.

b. Pith-Preferred Expression:

Patent Application WO 93/07278 (published Apr. 15, 1993; Ciba Geigy), which is herein incorporated by reference, describes the isolation of the maize trpA gene, which is preferentially expressed in pith cells. The gene sequence and promoter extending up to −1726 bp from the start of transcription are presented. Using standard molecular biological techniques, this promoter, or parts thereof, can be transferred to a vector such as pCGN1761 where it can replace the 35S promoter and be used to drive the expression of a foreign gene in a pith-preferred manner. In fact, fragments containing the pith-preferred promoter or parts thereof can be transferred to any vector and modified for utility in transgenic plants.

c. Leaf-Specific Expression:

A maize gene encoding phosphoenol carboxylase (PEPC) has been described by Hudspeth & Grula (Plant Molec Biol 12: 579–589 (1989)). Using standard molecular biological techniques the promoter for this gene can be used to drive the expression of any gene in a leaf-specific manner in transgenic plants.

d. Pollen-Specific Expression:

WO 93/07278 (published Apr. 15, 1993; Ciba Geigy) describes the isolation of the maize calcium-dependent protein kinase (CDPK) gene which is expressed in pollen cells. The gene sequence and promoter extend up to 1400 bp from the start of transcription. Using standard molecular biological techniques, this promoter or parts thereof, can be transferred to a vector such as pCGN1761 where it can replace the 35S promoter and be used to drive the expression of a nucleic acid sequence of the invention in a pollen-specific manner.

B. Transcriptional Terminators

A variety of transcriptional terminators are available for use in the expression cassettes of the present invention. These are responsible for the termination of transcription beyond the transgene and correct mRNA polyadenylation. Suitable transcriptional terminators are those that are known to function in plants and include, but are not limited to, the CaMV 35S terminator, the tml terminator, the nopaline synthase terminator and the pea rbcS E9 terminator. These can be used in both monocotyledons and dicotyledons. In addition, a gene's native transcription terminator may be used.

C. Sequences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize AdhI gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., *Genes Develop.* 1: 1183–1200 (1987)). In the same experimental system, the intron from the maize bronze1 gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. *Nucl. Acids Res.* 15: 8693–8711 (1987); Skuzeski et al. *Plant Molec. Biol.* 15: 65–79 (1990)). Other leader sequences known in the art include but are not limited to: picornavirus leaders, for example, EMCV leader (Encephalomyocarditis 5' noncoding region) (Elroy-Stein, O., Fuerst, T. R., and Moss, B. *PNAS USA* 86:6126–6130 (1989)); potyvirus leaders, for example, TEV leader (Tobacco Etch Vinis) (Allison et al., 1986); MDMV leader (Maize Dwarf Mosaic Virus); *Virology* 154:9–20); human immunoglobulin heavy-chain binding protein (BiP) leader, (Macejak, D. G., and Sarnow, P., *Nature* 353: 90–94 (1991); untranslated leader from the coat protein mRNA of alfalfa mosaic virus (AMV RNA 4), (Jobling, S. A., and Gelirke, L., *Nature* 325:622–625 (1987); tobacco mosaic virus leader (TMV), (Gallie, D. R. et al., *Molecular Biology, of RNA*, pages 237–256 (1989); and Maize Chlorotic Mottle Virus leader (MCMV) (Lommel, S. A. et al., *Virology* 81:382–385 (1991). See also, Della-Cioppa et al., *Plant Physiology* 84:965–968 (1987).

D. GC/AT Content

It is known in the art that the optimization of protein expression in plants may be enhanced by optimizing the coding regions of genes to the codon preference of the host. Accordingly, the preferred codon usage in plants differs from the preferred codon usage in certain microorganisms. Comparison of the usage of codons within a cloned microbial ORF to usage in plant genes (and in particular genes from the target plant) will enable an identification of the codons within the ORF which should preferably be changed.

Typically plant evolution has tended towards a strong preference of the nucleotides C and G in the third base position of monocotyledons, whereas dicotyledons often use the nucleotides A or T at this position. By modifying a gene to incorporate preferred codon usage for a particular target transgenic species, many of the problems described below for GC/AT content and illegitimate splicing will be overcome.

Plant genes typically have a GC content of more than 35%. ORF sequences which are rich in A and T nucleotides can cause several problems in plants. Firstly, motifs of ATTTA are believed to cause destabilization of messages and are found at the 3' end of many short-lived mRNAs. Secondly, the occurrence of polyadenylation signals such as AATAAA at inappropriate positions within the message is believed to cause premature truncation of transcription. In addition, monocotyledons may recognize AT-rich sequences as introns and may identify flanking splice sites (see below).

E. Sequences Adjacent to the Initiating Methionine

Plants differ from microorganisms in that their messages do not possess a defined ribosome binding site. Rather, it is believed that ribosomes attach to the 5' end of the message and scan for the first available ATG at which to start translation. Nevertheless, it is believed that there is a preference for certain nucleotides adjacent to the ATG and that expression of microbial genes can be achieved by the inclusion of a eukaryotic consensus translation initiator at the ATG. Clontech (1993/1994 catalog, page 210, incorporated herein by reference) have suggested one sequence as a consensus translation initiator for the expression of the *E. coli* uidA gene in plants. Further, Joshi (NAR 15: 6643–6653 (1987), incorporated herein by reference) has compared many plant sequences adjacent to the ATG and suggests another consensus sequence. In situations where difficulties are encountered in the expression of microbial ORFs in plants, inclusion of one of these sequences at the initiating ATG may improve translation. In such cases the last three nucleotides of the consensus may not be appropriate for inclusion in the modified sequence due to their modification of the second AA residue. Preferred sequences adjacent to the initiating methionine may differ between different plant species. A survey of 14 maize genes located in the GenBank database provided the following results:

Position Before the Initiating ATG in 14 Maize Genes:

| | $-10$ | $-9$ | $-8$ | $-7$ | $-6$ | $-5$ | $-4$ | $-3$ | $-2$ | $-1$ |
|---|---|---|---|---|---|---|---|---|---|---|
| C | 3 | 8 | 4 | 6 | 2 | 5 | 6 | 0 | 10 | 7 |
| T | 3 | 0 | 3 | 4 | 3 | 2 | 1 | 1 | 1 | 0 |
| A | 2 | 3 | 1 | 4 | 3 | 2 | 3 | 7 | 2 | 3 |
| G | 6 | 3 | 6 | 0 | 6 | 5 | 4 | 6 | 1 | 5 |

This analysis can be done for the desired plant species into which the nucleotide sequence is being incorporated, and the sequence adjacent to the ATG modified to incorporate the preferred nucleotides.

Genes cloned from non-plant sources and not optimized for expression in plants may also contain motifs which may be recognized in plants as 5' or 3' splice sites, and be cleaved, thus generating truncated or deleted messages. These sites can be removed using techniques well known in the art.

Techniques for modifying of coding sequences and adjacent sequences are well known in the art. In cases where the initial expression of a microbial ORF is low and it is deemed appropriate to make alterations to the sequence as described above, then the construction of synthetic genes can be accomplished according to methods well known in the art. These are, for example, described in the published patent disclosures EP 0 385 962 (published in Sep. 5, 1990 to Monsanto), EP 0 359 472 (issued Dec. 27, 1995 to Lubrizol) and WO 93/07278 (published Apr. 15, 1993 to Ciba-Geigy), all of which are incorporated herein by reference. In most cases it is preferable to assay the expression of gene constructions using transient assay protocols (which are well known in the art) prior to transferring to transgenic plants.

II. Plant Transformation Vectors and Selectable Markers

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred. Selection markers used routinely in transformation include the nptII gene, which confers resistance to kanamycin and related antibiotics (Messing & Vierra. Gene 19: 259–268 (1982); Bevan et al., Nature 304:184–187 (1983)), the bar gene, which confers resistance to the herbicide phosphinothricin (White et al., Nucl. Acids Res 18: 1062 (1990), Spencer et al. Theor. Appl. Genet 79: 625–631 (1990)), the hph gene, which confers resistance to the antibiotic hygromycin (Blochinger & Diggelmann, Mol Cell Biol 4: 2929–2931), and the dhfr gene, which confers resistance to methatrexate (Bourouis et al., EMBO J. 2(7): 1099–1104 (1983)), the EPSPS gene, which confers resistance to glyphosate (U.S. Pat. Nos. 4,940,835 and 5,188,642, issued Jul. 10, 1990 and Feb. 23, 1993, respectively both to Monsanto), and the mannose-6-phosphate isomerase gene (also referred to herein as the phosphomannose isomerase gene), which provides the ability to metabolize mannose (U.S. Pat. Nos. 5,767,378 and 5,994,629, issued Jun. 16, 1998 and Nov. 30, 1999, respectively both to Novartis).

Vectors Suitable for *Agrobacterium* Transformation

Many vectors are available for transformation using *Agrobacterium tumefaciens*. These typically carry at least one T-DNA border sequence and include vectors such as pBIN19 (Bevan, Nucl. Acids Res. (1984)). Below, the construction of two typical vectors suitable for *Agrobacterium* transformation is described.

pCIB200 and pCIB2001

The binary vectors pCIB200 and pCIB2001 are used for the construction of recombinant vectors for use with *Agrobacterium* and are constructed in the following manner. pTJS75kan is created by NarI digestion of pTJS75 (Schmidhauser & Helinski, J. Bacteriol. 164: 446–455 (1985)) allowing excision of the tetracycline-resistance gene, followed by insertion of an AccI fragment from pUC4K carrying an NPTII (Messing & Vierra, Gene 19: 259–268 (1982): Bevan et al., Nature 304: 184–187 (1983): McBride et al., Plant Molecular Biology 14: 266–276 (1990)). XhoI linkers are ligated to the EcoRV fragment of PCIB7 which contains the left and right T-DNA borders, a plant selectable nos/nptII chimeric gene and the pUC polylinker (Rothstein et al., Gene 53: 153–161 (1987)), and the XhoI-digested fragment are cloned into SalI-digested pTJS75kan to create pCIB200 (see also EP 0 332 104, example 19; published Mar. 20, 1991; Ciba Geigy).

pCIB200 contains the following unique polylinker restriction sites: EcoRI, SstI, KpnI, BglII, XbaI, and SalI. pCIB2001 is a derivative of pCIB200 created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for *Agrobacterium*-mediated transformation, the RK2-derived trpA function for mobilization between *E. coli* and other hosts, and the OriT and OriV functions also from RK2. The pCIB2001 polylinker is suitable for the cloning of plant expression cassettes containing their own regulatory signals.

pCIB 10 and Hygromycin Selection Derivatives Thereof:

The binary vector pCIB10 contains a gene encoding kanamycin resistance for selection in plants and T-DNA right and left border sequences and incorporates sequences from the wide host-range plasmid pRK252 allowing it to replicate in both *E. coli* and *Agrobacterium*. Its construction is described by Rothstein et al. (Gene 53: 153–161 (1987)). Various derivatives of pCIB10 are constructed which incorporate the gene for hygromycin B phosphotransferase described by Gritz et al. (Gene 25: 179–188 (1983)). These derivatives enable selection of transgenic plant cells on hygromycin only (pCIB743), or hygromycin and kanamycin (pCIB715, pCIB717).

Vectors Suitable for Non-*Agrobacterium* Transformation

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on *Agrobacterium* include transformation via particle bombardment, protoplast uptake (e.g. PEG and electroporation) and microinjection. The choice of vector depends largely on the preferred selection for the species being transformed. Below, the construction of typical vectors suitable for non-*Agrobacterium* transformation is described.

pCIB3064:

pCIB3064 is a pUC-derived vector suitable for direct gene transfer techniques in combination with selection by the herbicide basta (or phosphinothricin). The plasmid pCIB246 comprises the CaMV 35S promoter in operational fusion to the *E. coli* GUS gene and the CaMV 35S transcriptional terminator and is described in the PCT published application WO 93/07278 (published Apr. 15, 1993; Ciba Geigy). The 35S promoter of this vector contains two ATG sequences 5' of the start site. These sites are mutated using standard PCR techniques in such a way as to remove the ATGs and generate the restriction sites SspI and PvuII. The new restriction sites are 96 and 37 bp away from the unique SalI site and 101 and 42 bp away from the actual start site. The resultant derivative of pCIB246 is designated pCIB3025. The GUS gene is then excised from pCIB3025 by digestion with SalI and SacI, the termini rendered blunt and religated to generate plasmid pCIB3060. The plasmid pJIT82 may be obtained from the John Innes Centre, Norwich and the a 400 bp SmaI fragment containing the bar gene from *Streptomyces viridochromogenes* is excised and inserted into the HpaI site of pCIB3060 (Thompson et al. EMBO J 6: 2519–2523 (1987)). This generated pCIB3064, which comprises the bar gene under the control of the CaMV 35S promoter and terminator for herbicide selection, a gene for ampicillin resistance (for selection in *E. coli*) and a polylinker with the unique sites SphI, PstI, HindIII, and BamHI. This vector is suitable for the cloning of plant expression cassettes containing their own regulatory signals.

pSOG19 and pSOG35:

The plasmid pSOG35 is a transformation vector that utilizes the *E. coli* gene dihydrofolate reductase (DFR) as a selectable marker conferring resistance to methotrexate. PCR is used to amplify the 35S promoter (~800 bp), intron 6 from the maize Adh1 gene (~550 bp) and 18 bp of the GUS untranslated leader sequence from pSOG10. A 250-bp fragment encoding the *E. coli* dihydrofolate reductase type II gene is also amplified by PCR and these two PCR fragments are assembled with a SacI-PstI fragment from pB1221 (Clontech) which comprises the pUC19 vector backbone and the nopaline synthase terminator. Assembly of these fragments generates pSOG19 which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generates the vector pSOG35. pSOG19 and pSOG35 carry the pUC gene for ampicillin resistance and have HindIII, SphI, PstI and EcoRI sites available for the cloning of foreign substances.

Vector Suitable for Chloroplast Transformation

For expression of a nucleotide sequence of the present invention in plant plastids, plastid transformation vector pPH143 (WO 97/32011, example 36, published Sep. 4, 1997; Novartis) is used. The nucleotide sequence is inserted into pPH143 thereby replacing the PROTOX coding sequence. This vector is then used for plastid transformation and selection of transformants for *spectinomycin* resistance. Alternatively, the nucleotide sequence is inserted in pPH143 so that it replaces the aadH gene. In this case, transformants are selected for resistance to PROTOX inhibitors.

III. Transformation Methods

Plants transformed in accordance with the present invention may be monocots or dicots and include, but are not limited to, maize, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, canola, plum, cherry, peach, nectarine, apricot, strawberry, grape, raspberry, blackberry, pineapple, avocado, papaya, mango, banana, soybean, tomato, sorghum, sugarcane, sugarbeet, sunflower, rapeseed, clover, tobacco, carrot, cotton, alfalfa, rice, potato, eggplant, cucumber, *Arabidopsis thaliana*, and woody plants such as coniferous and deciduous trees, especially maize, wheat, or sugarbeet.

Once a desired DNA sequence has been transformed into a particular plant species, it may be propagated in that species or moved into other varieties of the same species, particularly including commercial varieties, using traditional breeding techniques.

Below are descriptions of representative techniques for transforming both dicotyledonous and monocotyledonous plants, as well as a representative plastid transformation technique.

Transformation of Dicotyledons

Transformation techniques for dicotyledons are well known in the art and include *Agrobacterium*-based techniques and techniques that do not require *Agrobacterium*. Non-*Agrobacterium* techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., EMBO J 3: 2717–2722 (1984), Potrykus et al., Mol. Gen. Genet. 199: 169–177 (1985), Reich et al., Biotechnology 4: 1001–1004 (1986), and Klein et al., Nature 327: 70–73 (1987). In each case the transformed cells are regenerated to whole plants using standard techniques known in the art.

Agrobacterium-mediated transformation is a preferred technique for transformation of dicotyledons because of its high efficiency of transformation and its broad utility with many different species. Agrobacterium transformation typically involves the transfer of the binary vector carrying the foreign DNA of interest (e.g. pCIB200 or pCIB2001) to an appropriate Agrobacterium strain which may depend of the complement of vir genes carried by the host Agrobacterium strain either on a co-resident Ti plasmid or chromosomally (e.g. strain CIB542 for pCIB200 and pCIB2001 (Uknes et al. Plant Cell 5: 159–169 (1993)). The transfer of the recombinant binary vector to Agrobacterium is accomplished by a triparental mating procedure using E. coli carrying the recombinant binary vector, a helper E. coli strain which carries a plasmid such as pRK2013 and which is able to mobilize the recombinant binary vector to the target Agrobacterium strain. Alternatively, the recombinant binary vector can be transferred to Agrobacterium by DNA transformation (Höfgen & Willmitzer, Nucl. Acids Res. 16: 9877 (1988)).

Transformation of the target plant species by recombinant Agrobacterium usually involves co-cultivation of the Agrobacterium with explants from the plant and follows protocols well known in the art. Transformed tissue is regenerated on selectable medium carrying the antibiotic or herbicide resistance marker present between the binary plasmid T-DNA borders.

Another approach to transforming a plant cell with a gene involves propelling inert or biologically active particles at plant tissues and cells. This technique is disclosed in U.S. Pat. Nos. 4,945,050, 5,036,006, and 5,100,792 all to Sanford et al (issued Jul. 31, 1990, Jul. 30, 1991, Mar. 31, 1992, respectively). Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

Transformation of Monocotyledons

Transformation of most monocotyledon species has now also become routine. Preferred techniques include direct gene transfer into protoplasts using PEG (polyethylene glycol) or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. Biotechnology 4: 1093–1096 (1986)).

Patent Applications EP 0 292 435 (issued Jul. 26, 1995 to Ciba Geigy), EP 0 392 225 (published Sep. 25, 1991; Ciba Geigy), and WO 93/07278 (published Apr. 15, 1993; Ciba Geigy) describe techniques for the preparation of callus and protoplasts from an elite inbred line of maize, transformation of protoplasts using PEG or electroporation, and the regeneration of maize plants from transformed protoplasts. Gordon-Kamm et al. (Plant Cell 2: 603–618 (1990)) and Fromm et al. (Biotechnology 8: 833–839 (1990)) have published techniques for transformation of A188-derived maize line using particle bombardment. Furthermore, WO 93/07278 (published Apr. 15, 1993; Ciba Geigy) and Koziel et al. (Biotechnology 11: 194–200 (1993)) describe techniques for the transformation of elite inbred lines of maize by particle bombardment. This technique utilizes immature maize embryos of 1.5–2.5 mm length excised from a maize ear 14–15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al. Plant Cell Rep 7: 379–384 (1988); Shimamoto et al. Nature 338: 274–277 (1989); Datta et al. Biotechnology 8: 736–740 (1990)). Both types are also routinely transformable using particle bombardment (Christou et al. Biotechnology 9: 957–962 (1991)). Furthermore, WO 93/21335 (published Nov. 28, 1993; Plant Genetic Systems) describes techniques for the transformation of rice via electroporation. Patent Application EP 0 332 581 (issued Dec. 11, 1996 to Ciba Geigy) describes techniques for the generation, transformation and regeneration of Pooideae protoplasts. These techniques allow the transformation of Dactylis and wheat. Furthermore, wheat transformation has been described by Vasil et al. (Biotechnology 10: 667–674 (1992)) using particle bombardment into cells of type C long-term regenerable callus, and also by Vasil et al. (Biotechnology 11: 1553–1558 (1993)) and Weeks et al. (Plant Physiol. 102: 1077–1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75–1 mm in length) are plated onto MS medium with 3% sucrose (Murashiga & Skoog, Physiologia Plantarum 15: 473–497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics® helium device using a burst pressure of ~1000 psi using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Tranformation of monocotyledons using *Agrobacterium* has also been described. See, WO 94/00977 (published Jan. 20, 1994; Japan Tobacco) and U.S. Pat. No. 5,591,616, (issued Jan. 7, 1997 to Japan Tobacco) both of which are incorporated herein by reference.

Transformation of Plastids

Seeds of *Nicotiana tabacum* c.v. 'Xanthi nc' are germinated seven per plate in a 1" circular array on T agar medium and bombarded 12–14 days after sowing with 1 µm tungsten particles (M10, Biorad, Hercules, Calif.) coated with DNA from plasmids pPH143 and pPH145 essentially as described (Svab, Z. and Maliga, P. (1993) *PNAS* 90, 913–917). Bombarded seedlings are incubated on T medium for two days after which leaves are excised and placed abaxial side up in bright light (350–500 µmol photons/m²/s) on plates of RMOP medium (Svab, Z., Hajdukiewicz, P. and Maliga, P. (1990) *PNAS* 87, 8526–8530) containing 500 µg/ml *spectinomycin* dihydrochloride (Sigma, St. Louis, Mo.). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (Sambrook et al., (1989) *Molecular Cloning: A Laboratory Manual*, Cold Spring Harbor Laboratory, Cold Spring Harbor). BamHI/EcoRI-digested total cellular DNA (Mettler, I. J. (1987) *Plant Mol Biol Reporter* 5, 346–349) is separated on 1% Tris-borate (TBE) agarose gels, transferred to nylon membranes (Amersham) and probed with $^{32}$P-labeled random primed DNA sequences corresponding to a 0.7 kb BamHI/HindIII DNA fragment from pC8 containing a portion of the rps7/12 plastid targeting sequence. Homoplasmic shoots are rooted aseptically on *spectinomycin*-containing MS/IBA medium (McBride, K. E. et al. (1994) *PNAS* 91, 7301–7305) and transferred to the greenhouse.

The invention will be further described by the following examples, which are not intended to limit the scope of the invention in any manner.

EXAMPLE 1

The deduced amino acid sequence of Nov9x (SEQ ID NO: 1) was converted into a maize optimized nucleic acid sequence using the Wisconsin GCG analysis program Back-translate and the codon table for highly expressed maize genes (see, e.g., U.S. Pat. No. 5,625,136). The synthetic gene was prepared by Integrated DNA technologies, Inc. (Coralville, Iowa).

Nov9X phytase amino acid sequence (the 8 mutations are bolded and underlined) (SEQ ID NO:1)

```
MAQSEPELKLESVVIVSRIIGVRAPTKATQLMQDVTPDAWPTWPVKLGEL
TPRGGELIAYLGHYWRQRLVADGLLPKCGCPQSGQVAIIADVDERTRKTG
EAFAAGLAPDCAITVHTQADTSSPDPLFNPLKTGVCQLDNANVTDAILER
AGGSIADFTGHYQTAFRELERVLNFPQSNLCLKREKQDESCSLTQALPSE
LKVSADCVSLTGAVSLASMLTEIFLLQQAQGMPEPGWGRITDSHQWNTLL
SLHNAQFDLLQRTPEVARSRATPLLDLIKTALTPHPPQKQAYGVTLPTSV
LFIAGHDTNLANLGGALELNWTLPGQPDNTPPGGELVFERWRRLSDNSQW
IQVSLVFQTLQQMRDKTPLSLNTPPGEVKLTLAGCEERNAQGMCSLAGFT
QWNEARIPACSL
```

Nov9X phytase maize-optimized nucleic acid sequence (SEQ ID NO:2) BamHI and SacI cloning sites (underlined) were included at the 5' and 3' ends, respectively. The start and stop codons are shown in bold.

```
GGATCCACCATGGCGCAGTCCGAGCCGGAGCTGAAGCTGGAGTCCGTGG
TGATCGTGTCCCGCCACGGCGTGGGCGCCCCGACCAAGGCCAGGCAGCT
CATGCAGGACGTGACCCCGGACGCCTGGCCGACCTGGCCGGTGAAGCTC
GGCGAGCTGACCCCGCGCGGCGGCGAGCTGATCGCCTACCTCGGCCACT
ACTGGCGCCAGCGCCTCGTGGCCGACGGCCTCCTCCCGAAGTGCGGCTG
CCCGCAGTCCGGCCAGGTGGCGATCATCGCCGACGTGGACGAGCGCACC
CGCAAGACGGGCGAGGCCTTCGCCGCCGGCCTCGCCCCGGACTGCGCCA
TCACCGTGCACACCCAGGCCGACACCTCCTCCCCGGACCCGCTCTTCAAC
CCGCTCAAGACCGGCGTGTGCCAGCTCGACAACGCCAACGTGACCGACG
CCATCCTGGAGCGCGCCGGCGGCTCCATCGCCGACTTCACCGGCCACTA
CCAGACCGCCTTCCGCGAGCTGGAGCGCGTGCTCAACTTCGGGCAGTCC
AACCTCTGCCTCAAGCGCGAGAAGCAGGACGAGTCGTGCTCCCTCACCC
AGGCCCTCCGGTCCGAGCTGAAGGTGTCCGCCGACTGCGTGTCCCTCACC
GGCGCCGTGTCCCTCGCCTCCATGCTCACCGAAATCTTCCTCCTCCAGCA
GGCCCAGGGCATGCCGGAGCCGGGCTGGGGCCGCATCACCGACTCCCAC
CAGTGGAACACCCTCCTCTCCCTCCACAACGCCCAGTTCGACCTCCTCCA
GCGCACCCCGGAGGTGGCCCGCTCCCGCGCCACCCCGCTCCTCGACCTC
ATCAAGACCGCCCTCACCCCGCACCCGCCGCAGAAGCAGGCCTACGGCG
TGACCCTCCCGACCTCGGTGCTCTTCATCGCCGGCCACGACACCAACCTC
GCCAACCTCGGCGGCGCCTGGAGCTGAACTGGACCCTCCCGGGCCAGC
CGGACAACACCCCGCCGGGCGGCGAGCTGGTGTTCGAGCGCTGGCGCCG
CCTCTCCGACAAGTCGCAGTGGATTGAGGTGTCCCTCGTGTTGCAGACCG
TCCAGCAGATGCGCGACAAGACCCCGCTCTCCCTCAACACCCGGCCGGG
CGAGGTGAAGCTCACCCTCGCCGGCTGCGAGGAGGGCAACGCCCAGGGG
ATGTGCTCCCTCGCCGGCTTCACCCAGATCGTGAACGAGGCCCGCATCCC
GGCCTGCTCCCTCTAATAGAGCTC
```

A. Preparation of Expression Cassettes having a Maize-Optimized Phytase Gene

The following Nov9x cassettes were constructed to express the Nov9X phytase in maize seed with various targeting signals. The Nov9x coding sequence has a BamHI cloning site at the 5' end and a SacI cloning site at the 3' end.

pNOV4054 comprises the γ-zein N-terminal signal sequence (MRVLLVALALLLALAASATS)(SEQ ID NO:3) fused to the synthetic Nov9X phytase for targeting to the endoplasmic reticulum and secretion into the apoplast (Torrent et al., 1997). The first residue after the signal sequence is Ala. This replaces Met1 in Nov9x.

pNOV4054 phytase fusion amino acid sequence (SEQ ID NO:4) (γ-zein sequence is in bold)

MRVLLVALALLLALAASATSAAQSEPELKLESVVIVSRHGVRAPTKATQLM

QDVTPDAWPTWPVKLGELTPRGGELIAYLGHYWRQRIVADGLLPKCGCPQ

SGQVAIIADVDERTRKTGEAFAAGLAPDCAITVHTQADTSSPDPLFNPLK

TGVCQLDNANVTDAILERAGGSIADFTGHYQTAFRELERVLNFPQSNLCL

KREKQDESCSLTQALPSELKVSADCVSLTGAVSLASMLTEIFLLQQAQGM

PEPGWGRITDSHQWNTLLSLHNAQFDLLQRTPEVARSRATPLLDLIKTAL

TPHPPQKQAYGVTLPTSVLFIAGHDTNLALNLGGALELNWTLPGQPDNTP

PGGELVFERWRRLSDNSQWIQVSLVFQTLQQMRDKTPLSLNTPPGEVKLT

LAGCEERNAQGMCSLAGFTQIVNEARIPACSL pNOV4054 phytase fusion nucleotide sequence (SEQ ID NO:5) showing flanking 5' BamHI and 3' SacI cloning sites (underlined). Start and stop codons are indicated in bold type.

<u>GGATCC</u>ACCATGAGGGTGTTGGTCGTTGCCCTCGCTCTCCTGGCTCTCGC

TGCGAGCGCCAGCAGCGCTGCGCAGTCCGAGGCGGAGCTGAAGCTGGAG

TCCGTGGTGATCGTGTCCCGCCACGGCGTGCGCGCCCCGACCAAGGCCA

CCCAGCTCATGCAGGACGTGACCCCGGACGCCTGGCCGACCTGGCCGGGT

GAAGCTCGGCGAGCTGACCCCGGGCGGCGGCGAGCTGATCGCCTACCTC

GGCCACTACTGGCGCCAGCGCCTCGTGGCCGACGCCTCCTCCCGAAGT

GCGGCTGCCCGCAGTCCGGCCAGGTGGCCATCATCGCCGACGTGGACGA

GCGCACCCGCAAGACCGGCGAGGCCTTCGCCGCCGGCCTCGCCCCGGAC

TGCGCCATCACCGTGCACACCCAGGCCGAGACCTCCTCCCCGGACCCGCT

CTTCAACCCGCTCAAGACCGGCGTGTGCCAGCTCGACAACGCCAACGTG

ACCGACGCCATCCTGGAGCGCGCCGGCGGCTCCATCGCCGACTTCACCG

GCCACTACCAGACCGCCTTCCGCGAGCTGGAGCGCGTGCTCAACTTCCC

GCAGTCCAACCTCTGCCTCAAGCGCGAGAAGCAGGACGAGTCCTGGTCC

CTCACCCAGGCCCTCCCGTCCGAGCTGAAGGTGTCCGCCGACTGCGTGTC

CCTCACCGGCGCCGTGTCCCTCGCCTCCATGCTCACCGAAATCTTCCTCC

TCCAGCAGGCCCAGGGCATGCCGGAGCCGGGGTGGGGCCGCATCAGCGA

CTCCCACCAGTGGAACACCCTCCTCTCCCTCCACAACGCCGAGTTCGACC

TCCTCCAGCGCACCCCGGAGGTGGCCGGCTCCCGCGCCACCCCGCTCCTC

GACCTCATCAAGACCGCCCTCACCCCGCAGGCGCGGCAGAAGCAGGCCT

AGGGCGTGACCCTGCCGACCTCCGTGCTCTTCATGGCCGGCGACGACACC

AAGCTCGCCAACCTCGGCGGCGCCCTGGAGCTGAACTGGACCCTCCCGG

GCCAGCCGGACAACACCCCGCCGGGCGGGGAGCTGGTGTTCGAGCGCTG

GCGCCGCCTCTCCGACAACTCCGAGTGGATTCAGGTGTCCCTCGTGTTCC

AGACCCTCCAGCAGATGCGCGACAAGACCCCGGTCTCCCTCAACACCCC

GCCGGGCGAGGTGAAGCTCAGCCTCGCCGGGTGCGAGGAGCGCAACGCC

CAGGGCATGTGCTCCCTCGCCGGGTTCACCCAGATCGTGAACGAGGCCC

GCATCCCGGCCTGCTCCCTCTAATAGAGCTC

NOV4058 comprises the γ-zein N-terminal signal sequence fused to the synthetic Nov9X phytase with a C-terminal addition of the sequence SEKDEL for targeting to and retention in the endoplasmic reticulum (Munro and Pelham, 1987). The first residue after the signal sequence is Ala. This replaces Met1 in Nov9x.

pNOV4058 phytase fusion amino acid sequence (SEQ ID NO:6) (γ-zein at N-terminus and SEKDEL sequence at C-terminus are shown in bold):

MRVLLVALALLLALAASATSAAQSEPELKLESVVIVSRHGVRAPTKATQLM

QDVTPDAWPTWPVKLGELTPRGGELIAYLGHYWRQRLVADGLLPKCGCPQ

SGQVAIIADVDERTRKTGEAFAAGLAPDCAITVHTQADTSSPDPLFNPLK

TGVCQLDNANVTDAILERAGGSIADFTGHYQTAFRELERVLNFPQSNLCL

KREKQDESCSLTQALPSELKVSADCVSLTGAVSLASMLTEIFLLQQAQGM

PEPGWGRITDSHQWNTLLSLHNAQFDLLQRTPEVARSRATPLLDLIKTAL

TPHPPQKQAYGVTLPTSVLFIAGHDTNLANLGGALELNWTLPGQPDNTPP

GGELVFERWRRLSDNSQWIQVSLVFQTLQQMRDKTPLSLNTPPGEVKLTL

AGCEERNAQGMCSLAGFTQIVNEARIPACSLSEKDEL pNOV4058 phytase fusion nucleotide sequence (SEQ ID NO:7) showing flanking 5' BamHI and 3' SacI cloning sites (underlined). Sequences encoding the gamma-zein signal sequence and SEKDEL signal are shown in bold type.

<u>GGATCC</u>ACCATGAGGGTGTTGCTCGTTGCCCTCGCTCTCCTGGCTCT

CGCTGCGAGCGCCACCAGCGCTGCGCAGTCCGAGCCGGAGCTGAAGCT

GGAGTCCGTGGTGATCGTGTCGCGCCACGGGGTGCGCGCCCCGACCAAG

GCCACGGAGCTGATGGAGGAGGTGACCCCGGACGGCTGGGGGACCTGGC

GGGTGAAGCTCGGCGAGCTGACCCCGCGCGGCGGCGAGCTGATCGCCTA

GCTCGGCCACTAGTGGCGCCAGCGCCTCGTGGCCGACGGGCTCCTCCCGA

AGTGCGGCTGCGCGGAGTCCGGGCAGGTGGCCATCATGGCCGACGTGGA

CGAGCGCAGCCGCAAGACGGGCGAGGCCTTCGGCGCCGGCCTCGCCCCG

GAGTGCGGGATCACCGTGGACACGCAGGCCGACAGGTCCTCCCGGGACC

CGCTCTTCAACCCGCTCAAGACCGGCGTGTGCCAGCTCGACAACGCCAA

CGTGACCGAGGCCATCCTGGAGCGGGGCGGCGGCTCCATCGCCGACTTC

```
ACCGGCCACTACCAGAGGGCCTTCCGCGAGCTGGAGGGGGTGCTGAAGT

TCCCGCAGTCGAACCTCTGCCTCAAGCGCGAGAAGCAGGACGAGTCCTG

CTCCCTCACCCAGGCCCTCCGGTCCGAGCTGAAGGTGTCCGCCGAGTGCG

TGTCGGTCACGGGGGCCGTGTCCCTCGCCTCCATGCTGACCGAAATCTTC

CTGCTCCAGCAGGGCCAGGGCATGCCGGAGGCGGGCTGGGGCGGATCA

CCGACTCCCACCAGTGGAACACCCTCGTGTCCCTCCACAACGCCGAGTTC

GACCTCCTCCAGCGCACCCCGGAGGTGGCCCGCTCCCGCGCCACCCCGC

TCCTCGACCTCATCAAGACCGCCCTCACGCCGCACCCGCCGCAGAAGGA

GGCCTACGGCGTGACCCTCCCGACCTCCGTGCTCTTCATCGCCGGCCACG

ACACCAACCTCGCCAACCTCGGCGGCGCCCTGGAGCTGAACTGGACCCT

CCCGGGCCAGCCGGACAACACCCCGCCGGGCGGCGAGCTGGTGTTCGAG

CGCTGGGGCCGCCTCTCCGACAACTCCCAGTGGATTCAGGTGTCCCTCGT

GTTCCAGACCGTCCAGCAGATGCGCGACAAGACCCCGCTCTCCCTCAAC

ACCCCGCCGGGCGAGGTGAAGCTCACCCTGGCCGGCTGCGAGGAGCGCA

ACGCGCAGGGCATGTGCTCCCTCGCCGGCTTCACCCAGATCGTGAACGA

GGCCCGCATCCCGGCCTGCTCCCTCTCCGAGAAGGACGAGCTGTAATA

GAGCTC
```

B. Isolation of Promoters for Endosperm-Specific Expression in Maize

The promoter from the *Zea mays* γ-zein gene (obtained from Dr. Brian Larkins) is amplified as a 673 bp fragment from plasmid pGZ27.3. The γ-zein promoter has been shown to be endosperm specific (Torrent et al., 1997). HindIII and BamHI cloning sites were introduced at the 5' and 3' ends, respectively. These sites are underlined.

*Zea mays* γ-zein promoter nucleic acid sequence (SEQ ID NO:8)

```
AAGCTTCGATCATCCAGGTGCAACCGTATAAGTCCTAAAGTGGTGAGGA

ACACGAAACAACCATGCATTGGCATGTAAAGCTCCAAGAATTTGTTGTA

TCCTTAACAACTCACAGAACATCAACCAAAATTGCACGTCAAGGGTATT

GGGTAAGAAACAATCAAACAAATCCTCTGTGTGTGCAAAGAAACACGGT

GAGTCATGCCGAGATCATACTCATCTGATATACATGCTTACAGCTCACAA

GACATTACAAACAACTCATATTGCAITACAAAGATCGTTTCATGAAAAA

TAAAATAGGCCGGACAGGACAAAAATCCTTGACGTGTAAAGTAAATTTA

CAACAAAAAAAAGCCATATGTCAAGCTAAATCTAATTCGTTTTACGTA

GATCAACAAGGTGTAGAAGGCAACAAAACTGAGGCACGCAGAAGTACA

GAATGATTGCAGATGAACCATCGACGTGCTACGTAAAGAGAGTGACGAG

TCATATAGATTTGGCAAGAAACCATGAAGCTGCCTACAGCCGTCTCGGT

GGCATAAGAACACAAGAAATTGTGTTAATTAATCAAAGCTATAAATAAC

GCTCGCATGCCTGTGCACTTCTCGATCACCACCACTGGGTCTTCAGACCA

TTAGCTTTATCTACTGCAGAGCGCAGAAGAACCCGATCGACAGGATGC
```

C. Isolation of Promoters for Embryo-Specific Expression in Maize

The promoter and 5' noncoding region of the major maize embryo globulin, glob I, was amplified as a 1427 base pair fragment from maize genomic DNA using primers designed from Genbank accession L22344. The globulin promoter has been shown to be primarily embryo-specific (Belanger and Kriz, 1989). HindIII and BamHI cloning sites were introduced at the 5' and 3' ends, respectively. These sites are underlined.

*Zea mays* globulin1 promoter nucleic acid sequence (SEQ ID NO:9)

```
AAGCTTAGTGCCATCCTTGGACACTCGATAAAGTATATTTTATTTTTTTT

ATTTTGCCAACCAAACTTTTTGTGGTATGTTCCTACACTATGTAGATCTA

CATGTACCATTTTGGCACAATTACATATTTACAAAAATGTTTTCTATAAA

TATTAGATTTAGTTCGTTTATTTGATTTCTTCGGAAAATTCACATTTAAA

CTGCAAGTCACTCGAAACATGGAAAACCGTGCATGCAAAATAAATGATAT

GCATGTTATCTAGCACAAGTTACGACCGATTTCAGAAGCAGACCAGAATC

TTCAAGCACCATGCTCACTAAACATGACCGTGAACTTGTTATCTAGTTGT

TTAAAAATTGTATAAAACACAAATAAAGTCAGAATTAATGAAACTTGT

CCACATGTCATGATATCATATATAGAGGTTGTGATAAAAATTTGATAATG

TTTCGGTAAAGTTGTGACGTACTATGTGTAGAAACCTAAGTGACCTACAC

ATAAAATCATAGAGTTTCAATGTAGTTCACTCGACAAAGACTTTGTCAAG

TGTCCGATAAAAGTACTCGACAAAGAAGCCGTTGTCGATGTACTGTTC

GTCGAGATCTCTTTGTCGAGTGTCACACTAGGCAAAGTCTTTACGGAGTG

TTTTTCAGGCTTTGACACTCGGCAAAGCGCTCGATTCCAGTAGTGACAGT

AATTTGCATCAAAAATAGCTGAGAGATTTAGGCCCCGTTTCAATCTCACG

GGATAAAGTTTAGCTTCCTGCTAAACTTTAGCTATATGAATTGAAGTGCT

AAAGTTTAGTTTCAATTACCACCATTAGCTCTCCTGTTTAGATTACAAAT

GGCTAAAAGTAGCTAAAAAATAGCTGCTAAAGTTTATCTCGCGAGATTG

AAACAGGGCCTTAAAATGAGTCAACTAATAGACCAACTAATTATTAGCT

ATTAGTCGTTAGCTTCTTTAATCTAAGCTAAAACCAACTAATAGCTTATT

TGTTGAATTACAATTAGCTCAACGGAATTCTCTGTTTTTTCTATAAAAAA

AGGGAAACTGCCCCTCATTTACAGCAAATTGTCCGCTGCCTGTCGTCCAG

ATACAATGAACGTACCTAGTAGGAACTCTTTTACACGCTCGGTCGCTCGC

CGCGGATCGGAGTCCCAGGAACACGACACCACTGTGTAACACGACAAAG

TCTGCTCAGAGGCGGCCACACCCTGGCGTGCACCGAGCCGGAGCCCGGA

TAAGCACGGTAAGGAGAGTACGGCGGGACGTGGCGACCCGTGTGTCTGC

TGCCACGCAGCCTTCCTCCACGTAGCCGCGCGGCCGCGCCACGTACCAG

GGCCCGGCGCTGGTATAAATGCGCGCTACCTCCGCTTTAGTTCTGCATAC

AGTCAACCTAACACACCCGAGCATATCACAGTGGGATCC
```

D. Construction of Plant Transformation Vectors for the Maize-Optimized Phytase Gene Binary vectors for maize transformation were constructed in two steps. In the first step, three fragments were fused to generate an expression cassette. The expression cassette consisted of a HindIII-BamHI promoter cassette (sections B & C above) fused to a BamHI-SacI Nov9x cassette (section A above) fused to a SacI-KpnI terminator cassette. The terminator cassette included an inverted PEPC intron. The expression cassette was then transferred as a HindIII-KpnI fragment into the binary vector pNOV2117, which contains the phosphomannose isomerase (PMI) gene allowing for selection of transgenic cells with mannose.

A summary of the binary vectors prepared for plant transformation is shown in Table 1. The six vectors were introduced into maize.

The Nov9X binary vectors listed in Table 1 all contain the same terminator cassette with a PEPC intron. Vectors pNOV4051, 4055, and 4059 contain the globulin promoter cassette, and vectors pNOV4053, 4057, and 4061 contain the gamma-zein promoter cassette. Vectors pNOV4051 and 4053 contain the Nov9X sequence shown in SEQ ID NO:2 with cytoplasmic targeting. Vectors pNOV4055 and 4057 contain the Nov9X cassette from pNOV4054 with apoplast targeting. Vectors pNOV4059 and 4061 contain the Nov9X cassette from pNOV4058 with ER retention.

TABLE 1

| Vector | promoter (source) | signal seq. | gene | Crop | Predicted localization |
|---|---|---|---|---|---|
| pNOV4051 | globulin | none | NOV9X | maize | embryo cytoplasm |
| pNOV4053 | gamma-zein | none | NOV9X | maize | endosperm cytoplasm |
| pNOV4055 | globulin | gamma-zein | NOV9X | maize | embryo apoplast |
| pNOV4057 | gamma-zein | gamma-zein | NOV9X | maize | endosperm apoplast |
| pNOV4059 | globulin | gamma-zein | NOV9X-SEKDEL | maize | embryo ER |
| pNOV4061 | gamma-zein | gamma-zein | NOV9X-SEKDEL | maize | endosperm ER |

The vectors pNOV4057 and pNOV4059 have been deposited in the Agricultural Research Culture Collection (NRRL), 1815 N, University Street, Peoria, Ill. 61604, USA, as International Depositary Authority as established under the Budapest Treaty on the International Recognition of the Deposit of Microorganisms for the Purposes of Patent Procedure, Accession numbers NRRL B-30537, and NRL B-30538, respectively, on Dec. 28, 2001.

EXAMPLE 2

Genetic Modification of Maize and Wheat

The synthetic Nov9X gene inserted into an appropriate vector as described above was introduced into maize by *Agrobacterium*-mediated transformation and into wheat by biolistic transformation. Stable transformants were regenerated from tissue cultured on selective media using the Positech system in accordance with U.S. Pat. Nos. 5,767,378 and 5,994,629.

*Agrobacterium*-Mediated Transformation of Maize

Transformation of immature maize embryos is performed essentially as described in Negrotto et al., (2000) Plant Cell Reports 19: 798–803. Various media constituents described therein can be substituted.

Transformation Plasmids and Selectable Marker

The genes used for transformation are cloned into a vector suitable for maize transformation as described above. Vectors used contain the phosphomannose isomerase (PMI) gene (Negrotto et al. (2000) Plant Cell Reports 19: 798–803) as a selectable marker.

Preparation of *Agrobacterium tumefaciens*

*Agrobacterium* strain LBA4404 (pSB1) containing the plant transformation plasmid is grown on YEP (yeast extract (5 g/L), peptone (10 g/L), NaCl (5 g/L), 15 g/l agar, pH 6.8) solid medium for 2 to 4 days at 28° C. Approximately $0.8 \times 10^9$ *Agrobacteria* are suspended in LS-inf media supplemented with 100 µM acetosyringone (As) (LSAs medium) (Negrotto et al., (2000) Plant Cell Rep 19: 798–803). Bacteria are pre-induced in this medium for 30–60 minutes.

Inoculation

Immature embryos from A188 or other suitable maize genotypes are excised from 8–12 day old ears into liquid LS-inf+100 µM As (LSAs). Embryos are vortexed for 5 seconds and rinsed once with fresh infection medium. Infection media is removed and *Agrobacterium* solution is then added and embryos are vortexed for 30 seconds and allowed to settle with the bacteria for 5 minutes. The embryos are then transferred scutellum side up to LSAs medium and cultured in the dark for two to three days. Subsequently, between 20 and 25 embryos per petri plate are transferred to LSDc medium supplemented with cefotaxime (250 mg/l) and silver nitrate (1.6 mg/l) (Negrotto et al. 2000) and cultured in the dark for 28° C. for 10 days.

Selection of Transformed Cells and Regeneration of Transformed Plants

Immature embryos producing embryogenic callus are transferred to LSD1M0.5S medium (LSDc with 0.5 mg/l 2,4-D instead of Dicamba, 10 g/l mannose, 5 g/l sucrose and no silver nitrate). The cultures are selected on this medium for 6 weeks with a subculture step at 3 weeks. Surviving calli are transferred either to LSD1M0.5S medium to be bulked-up or to Reg1 medium (as described in Negrotto et al., 2000). Following culturing in the light (16 hour light/8 hour dark regiment), green tissues are then transferred to Reg2 medium without growth regulators (as described in Negrotto et al. 2000) and incubated for 1–2 weeks. Plantlets are transferred to Magenta GA-7 boxes (Magenta Corp, Chicago Ill.) containing Reg3 medium (as described in Negrotto et al. 2000) and grown in the light. Plants that are PCR positive for the Nov9X expression cassette are transferred to soil and grown in the greenhouse.

DNA Analysis

The presence of the Nov9X gene was determined by ±PCR assay or by a Taqman copy number assay. The presence of the PMI selective marker was determined by a Taqman copy number assay. The presence of the *spectinomycin* resistance gene selective marker was determined by ±PCR assay.

EXAMPLE 3

Protein Extraction from Corn Seeds

Ears from first and second generation transgenic maize plants were harvested at 24–40 days or about 30 days after pollination (DAP). Fresh kernels and isolated endosperm were pulverized in water at room temperature. Proteins were extracted in water using a mortar and pestle.

Alternatively, kernels were dried on the cob at 105° F. for 5 days. Dried kernels were pulverized to yield a flour using a Kleco tissue pulverizer at room temperature for 20–30 seconds. Proteins were extracted from 100 mg flour by addition of 1 ml buffer and incubation for 20 min at room temperature.

Insoluble material was removed by centrifugation for 10 min at 4° C. Extracts were kept on ice. Protein concentration was determined using the ADV01 protein assay reagent (Cytoskeleton, Denver, Colo.) with BSA as the standard. Protein assays were performed in 96-well plates and 310 µl reactions. Absorbance was measured at 595 nm using a SpectraMaxPlus plate reader (Molecular Devices). Typically 10 µl of a 10-fold dilution of the extract was diluted further with 300 µl of ADV01 reagent.

Enzyme Assay

Estimation of Phytase Activity

Determination of phytase activity, based upon the estimation of inorganic phosphate released on hydrolysis of phytic acid, can be performed at 37° C. following the method described by Engelen et al. (2001). One unit of enzyme activity is defined as the amount of enzyme that liberates 1 µmol of inorganic phosphate per minute under assay conditions. For example, phytase activity may be measured by incubating 2.0 ml of the enzyme preparation with 4.0 ml of 9.1 mM sodium phytate in 250 mM sodium acetate buffer pH 5.5, supplemented with 1 mM $CaCl_2$ for 60 minutes at 37° C. After incubation, the reaction is stopped by adding 4.0 ml of a color-stop reagent consisting of equal parts of a 10% (w/v) ammonium molybdate and a 0.235% (w/v) ammonium vanadate stock solution. Phosphate released is measured against a set of phosphate standards spectrophotometrically at 415 nm. Phytase activity is calculated by interpolating the $A_{415}$ nm absorbance values obtained for phytase containing samples using the generated phosphate standard curve. Alternatively, a phytase activity curve generated by using a standardized phytase reference whose activity is certified by the manufacturer may be used in place of a phosphate standard curve to determine enzymatic activity. Specific activity can be expressed in units of enzyme activity per mg of protein.

Alternatively, phytase activity may be measured according to the procedure of Wyss et al., 1999 with modifications. Assays were performed in 1.5 ml tubes and 96-well microplates. The tube assays were started by mixing 5 µl 1 M sodium acetate (pH 4.5), 10 µl 10 mM phytic acid (Sigma Cat. # P8810), 5 µl distilled water, and 5 µl diluted extract. The reaction was incubated at 37° C. for 10 min, after which the tubes were placed on ice and the reaction quenched immediately by addition of 25 µl 15% trichloroacetic acid (TCA). The quenched reaction was diluted with 450 µl distilled water.

Colorimetric determination of phosphate concentration was initiated by addition of 500 µl of the calorimetric reagent (0.6 M sulfuric acid, 2% ascorbate, 0.5% ammonium molybdate) and incubation at 50° C. for 15 min. Phosphate concentration was determined by measuring absorbance at 800 nm and comparison to a standard curve of potassium phosphate.

Assays in microplates (flat bottom, 300 µl well volume) were started by mixing 20 µl 1 M sodium acetate, 40 µl 10 mM phytic acid, and 40 µl of diluted extract. The plate was kept on ice during mixing. The plate was sealed with foil and placed on a plate heater (Boekel-Grant PH-100) at 37° C. for 10 min. The plate was transferred to ice and the reactions were quenched by addition of 100 µl 15% TCA. 15 µl of the quenched reaction was diluted with 135 µl distilled water in a second plate, and the calorimetric reaction was initiated by addition of 150 µl of the colorimetric reagent. The second plate included phosphate standards. The plate was sealed with foil and incubated on the plate heater at 50° C. for 15 min. Absorbance at 820 nm was measured for duplicate standards and samples.

SDS-PAGE and Western Blot Analyses

Electrophoresis sample buffer and running buffer were according to Laemmli, 1970. Samples were boiled for 2 minutes prior to electrophoresis using precast NOVEX Tris-Glycine gels (Invitrogen). Electrophoretic transfers were performed using the NOVEX Mini-Cell system (Invitrogen) using the manufacturer's protocol and buffer recipes. The transfer buffer contained 12 mM Tris, 96 mM glycine, and 20% methanol. Polypeptides were transferred to nitrocellulose (NOVEX LC2000) for 1–2 hours at 25 V and room temperature. Membranes were blocked for 15 min at room temperature by incubation in 30 mM Tris-HCl (pH 10.2), 150 mM NaCl, and 0.05% Tween-20 (TBST) supplemented with 3% BSA.

The primary immune serum from goat was obtained from Duncroft, Inc. (Lovettsville, Va.). The goat was inoculated with recombinant Nov9X phytase extracted from *E. coli* (obtained from Diversa). Blots were incubated with primary antibody (1:2000 dilution in TBST) for 1 hour at room temperature followed by 35-minute washes with TBST. The procedure was repeated using secondary antibody (mouse anti-goat IgG) diluted 1:50,000 in TBST. Blots were developed using enhanced chemiluminescence (Pierce SuperSignal Ultra).

EXAMPLE 3

Accumulation of Nov9X Phytase in Maize Seed from First Generation Transgenic Plants Transformed with Vectors pNOV4057 and pNOV4061.

An exemplary formulation of phytase enzyme produced in corn seed is in the form of a liquid extract. Here, the enrichment of Nov9X phytase by degermination, water extraction, heating, and centrifugation is described.

Fresh kernels from two of the first generation transgenic plants to produce mature ears were analyzed for phytase activity. The plants were derived from embryos that had been transformed with plasmids pNOV4057 (event 305A13) and pNOV4061 (event 305B11). Fresh kernels of the same age were obtained from a third ear that did not contain the Nov9X phytase gene. This control plant (event 264A8C#14) contained the vector pNOV4314, which encodes a heterologous enzyme. Six kernels and six endosperm from each of the three ears were pooled and crushed using a mortar and pestle. A total of 10 ml $ddH_2O$ was added to the kernels. The soluble fractions of the suspensions were analyzed for total protein and phytase activity.

Results of phytase assays of kernel and endosperm extracts are shown in FIG. 1. The assay measures phosphate concentration in the reaction after a 10 minute incubation at 37° C. Extracts from the negative control tissue are included in order to determine the level of endogenous phosphate (FIG. 1, top). This level of background phosphate is reproducible based on analysis of several extractions of flour from control samples (data not shown). After correcting for background phosphate, phytase activity was calculated for the two plants containing the Nov9X phytase gene. The phytase activity is reported as total units extracted from 6 kernels and is shown in FIG. 1, bottom. The differences in total phytase activity between kernels and endosperm from the same ear is due to segregation of the transgene(s).

A portion of each of the endosperm extracts analyzed in FIG. 1 was heated at 60° C. for 30 min. As shown in FIG.

Figure 2A:
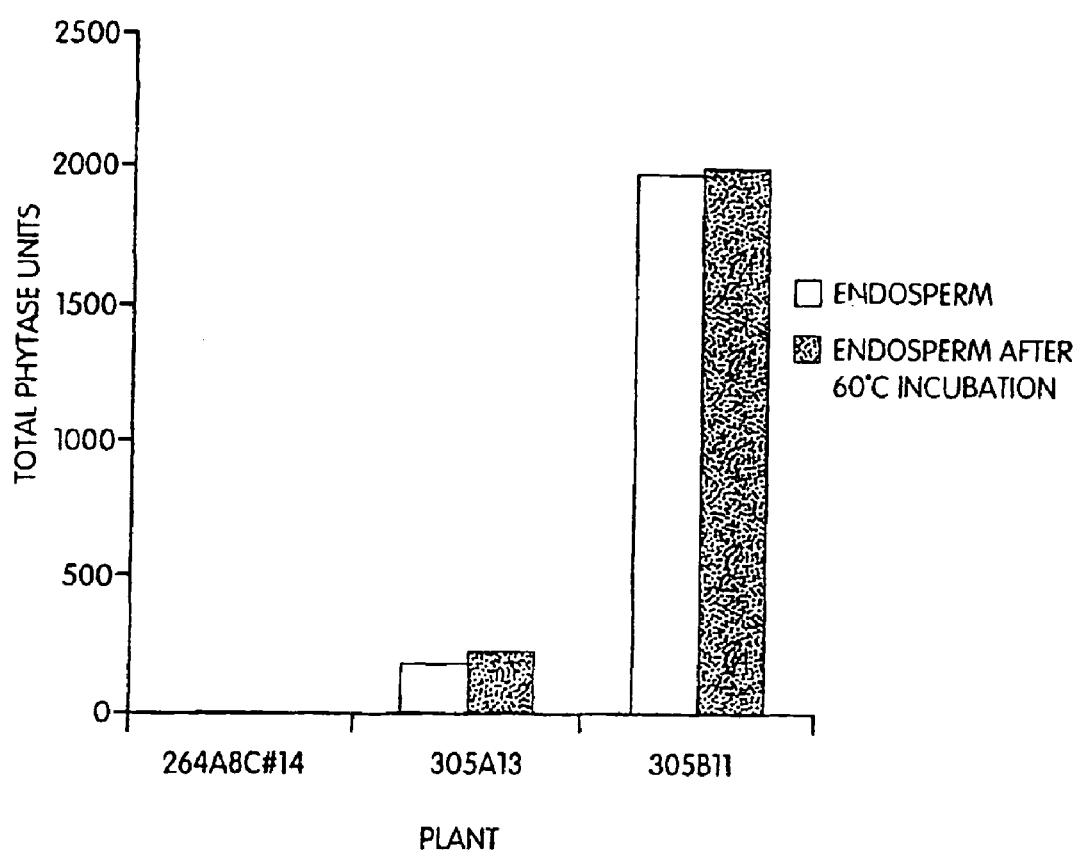
FIG. 2 demonstrates that recombinant Nov9X phytase activity produced in maize is heat stable. Units are defined as in described in FIG. 1. A. Total phytase activity extracted. B. SDS-PAGE gel of extracts stained with Coomassie blue.
Figure 2B:
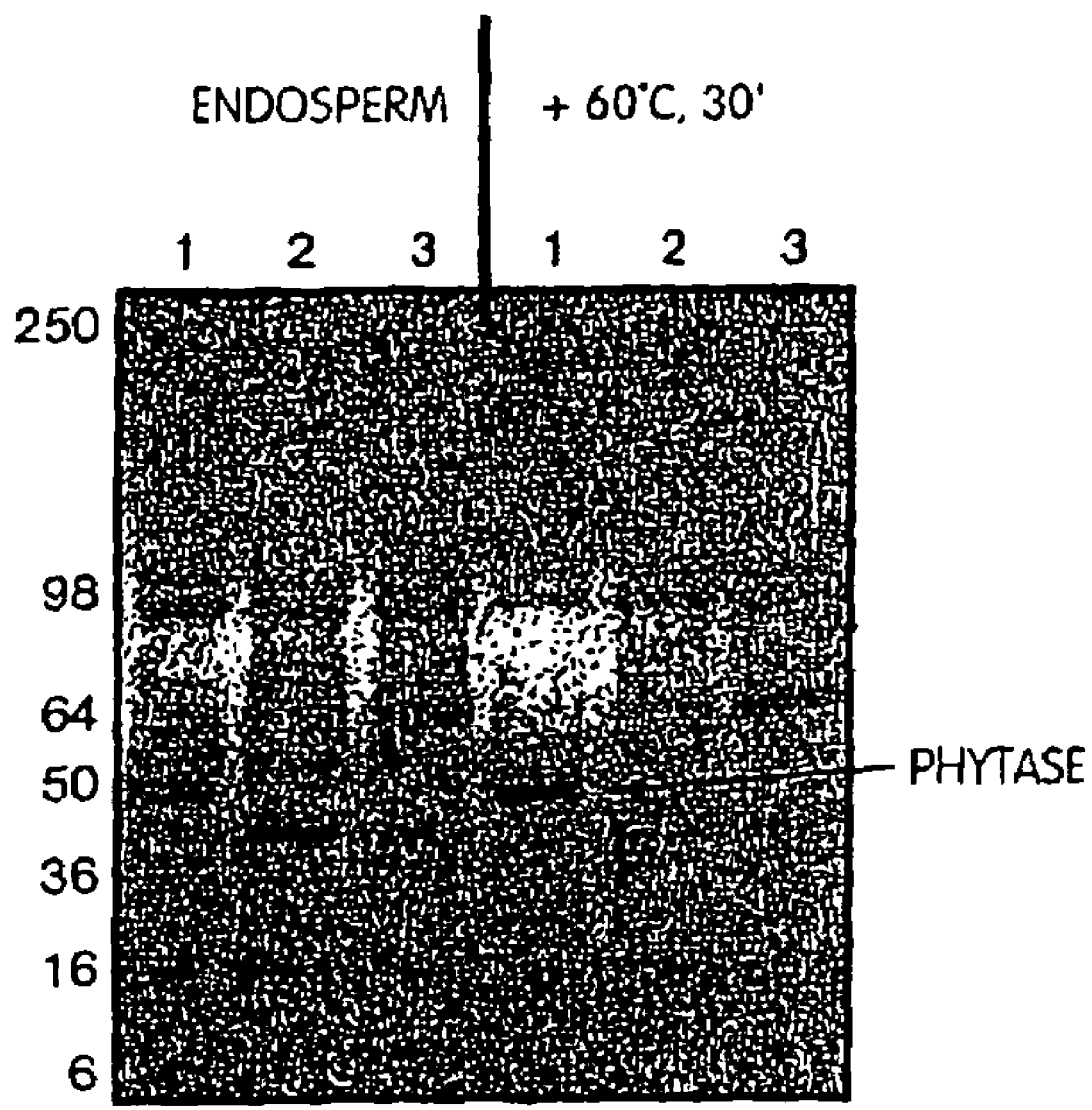

2A, the phytase activity in these extracts was unaffected by heating. Samples of unheated and heated endosperm extracts were analyzed by SDS-PAGE (FIG. 2B). The calculated size of the Nov9X gene product is 43 kDa. A protein in the range of 40–50 kD was abundant in the extract of 305B11. This protein remained soluble during heating and was the most abundant protein in the soluble fraction of the heated endosperm extract. A band in this region of the gel was identified by Western blot analysis using antiserum from a goat inoculated with Nov9X produced in E. coli. This band is a good candidate for the recombinant phytase enzyme.

Figure 3A:
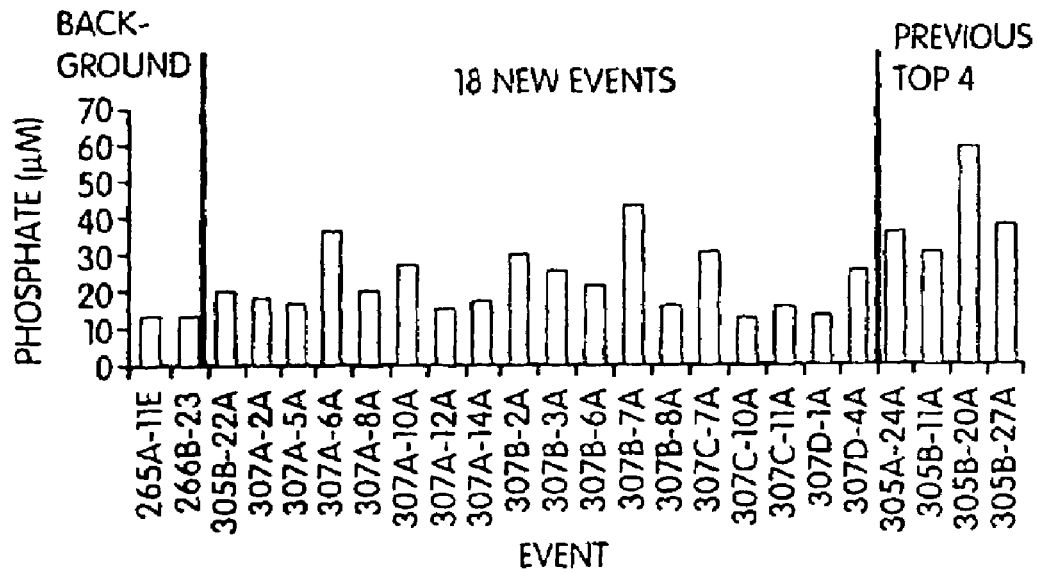
FIG. 3 provides a comparison of phytase levels in extracts of flour from dried kernels. All plants contain either pNOV4057 or pNOV4061. Top: phosphate concentration of reactions. Bottom: Phytase units are reported as μmoles phosphate liberated/mg protein/min. Nov9X copy # top 4: 305A24A, 2 copies; 305B11A, 20A, 27A all >3 copies.
Figure 3B:
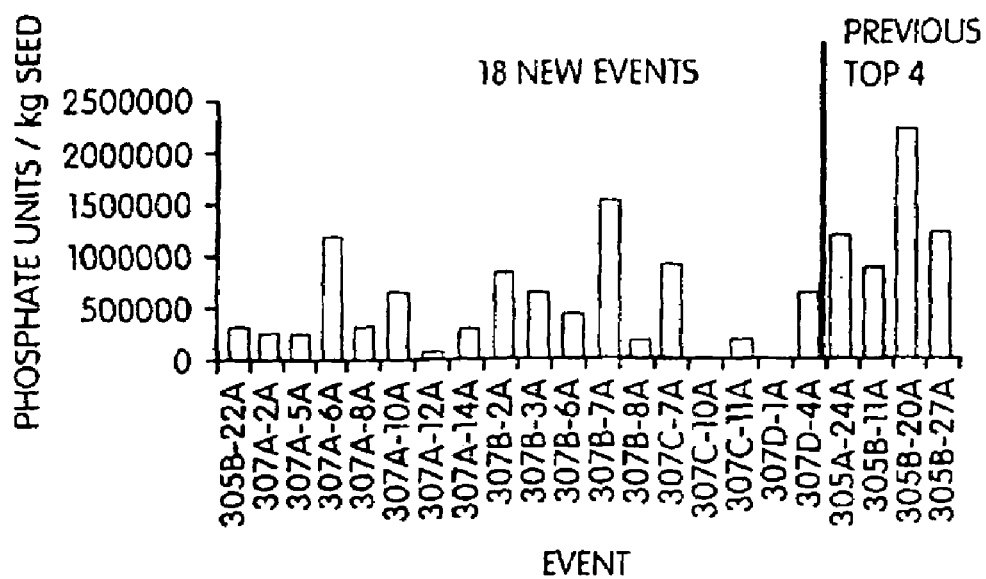

An additional source of enzyme for a liquid formulaton is to use dried seed or flour obtained from dried seed. The seed may be milled to produce flour. Seed harvested 30 DAP (days after pollination) from several plants were dried for five days at 105° F. Dried seed were pulverized and proteins were extracted in buffer as described above. A comparison of phytase activity in kernel extracts of 22 plants is shown in FIG. 3. Four plants with the highest levels of phytase activity from an initial screening of 24 plants were included in the analysis.

Another exemplary formulation of phytase enzyme produced in corn seed is as cracked or milled grain, or flour. Phytase-containing flour can be added directly to animal feed as a supplement, or it can be processed further, for example to a pelleted form. The following experiment compares the phytase activity of a liquid extract with flour.

Twenty milligrams (mg) flour was incubated in 200 µl buffer for 20 minutes at room temperature. One set of tubes was then chilled on ice while the insoluble material in the second set was removed by centrifugation at 4° C. The total suspension from the first set and the total supernatant fraction from the second set of tubes were then diluted to a final volume of 5 ml with extraction buffer. Phytic acid (10 ml 0.1 M) and sodium acetate (10 ml 0.5 M, pH 5) were added and the tubes were incubated for 10 min at 37° C. The final concentration of 40 mM phytic acid represents a 10-fold increase over that used in the standard assay described above. The reactions were chilled on ice and immediately quenched by addition of an equal volume (25 ml) of 15% TCA. Insoluble material was removed by centrifugation (15 min, 4° C., 3,700 rpm) and a portion of the supernatant fraction was used to measure phosphate concentration as described above.

Figure 4A:
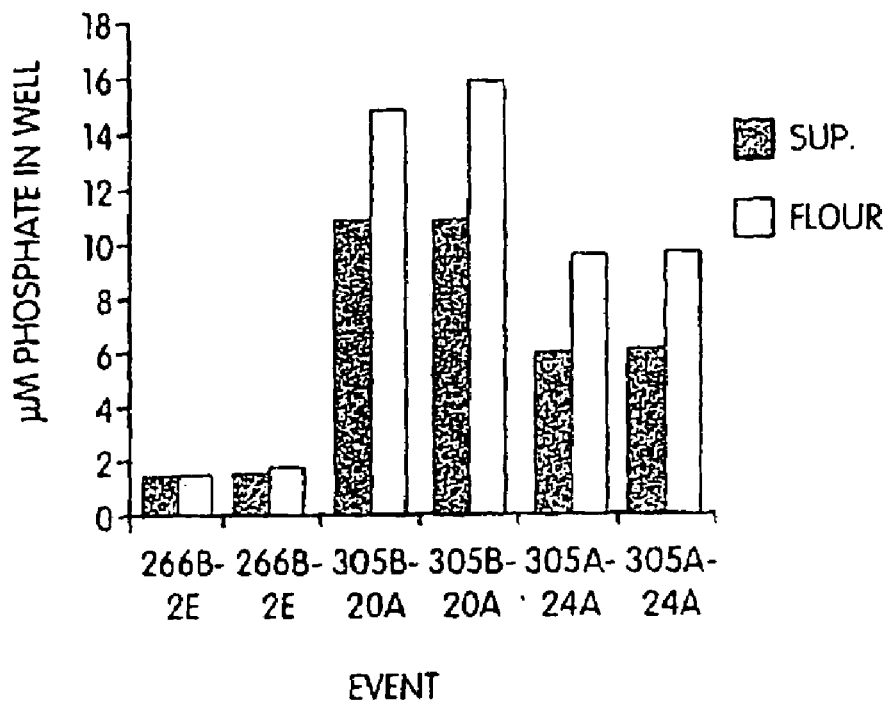
FIG. 4 shows the accumulation of phytase (Nov9X) produced in maize. The figures provide a comparison of phytase activity in corn flour suspensions and flour extracts. 266B-2E is a negative control. The phosphate concentration of all samples are shown in the top graph. Phytase units were calculated after correcting for the endogenous phosphate present in the negative control 266B-2E. Duplicates of each control and treatment are shown. The phosphate concentration of the negative control was subtracted from that of the treatments in order to determine phosphate released due to phytase activity (bottom graphs).
Figure 4B:
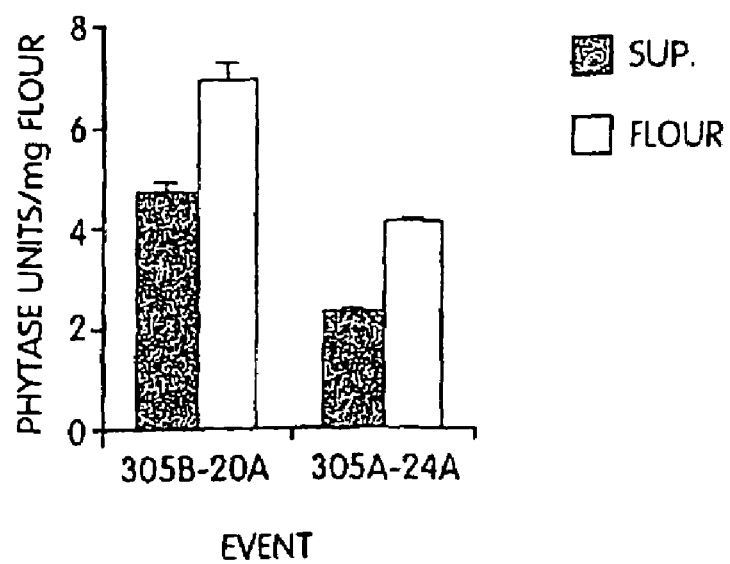

The phytase activity in flour extracts and flour suspensions was compared in order to determine the efficiency of the buffer extraction procedure. Whole kernel flour (20 mg) was incubated with 200 µl of extraction buffer and the total phytase activity of the supernatant fraction and flour suspension was determined. The results are shown in FIG. 4. Total phosphate concentrations in equivalent portions of the reactions are shown in the top graph. Event 266B-2E is a negative control that does not contain recombinant phytase. These samples were assayed to determine levels of endogenous phosphate. Events 305B-20A and 305A-24A are transgenic phytase events transformed with vectors pNOV4061 and pNOV4057, respectively. The yellow bars indicate phosphate concentrations in reactions containing the soluble extract and the blue bars indicate phosphate levels in reactions containing the flour suspension. For both transgenic events additional phosphate was liberated in the presence of transgenic flour.

The graphs in the bottom of FIG. 4 compare phytase activity in the soluble extracts (yellow) and flour suspensions (blue) of the two events. For events 305B-20A (pNOV4061) and 305A-24A (pNOV4057) additional activity of 50% and 80%, respectively, remained associated with the flour.

EXAMPLE 4

Endosperm-Specific Expression of Nov9x Phytase in T2 Seed

Figure 5:
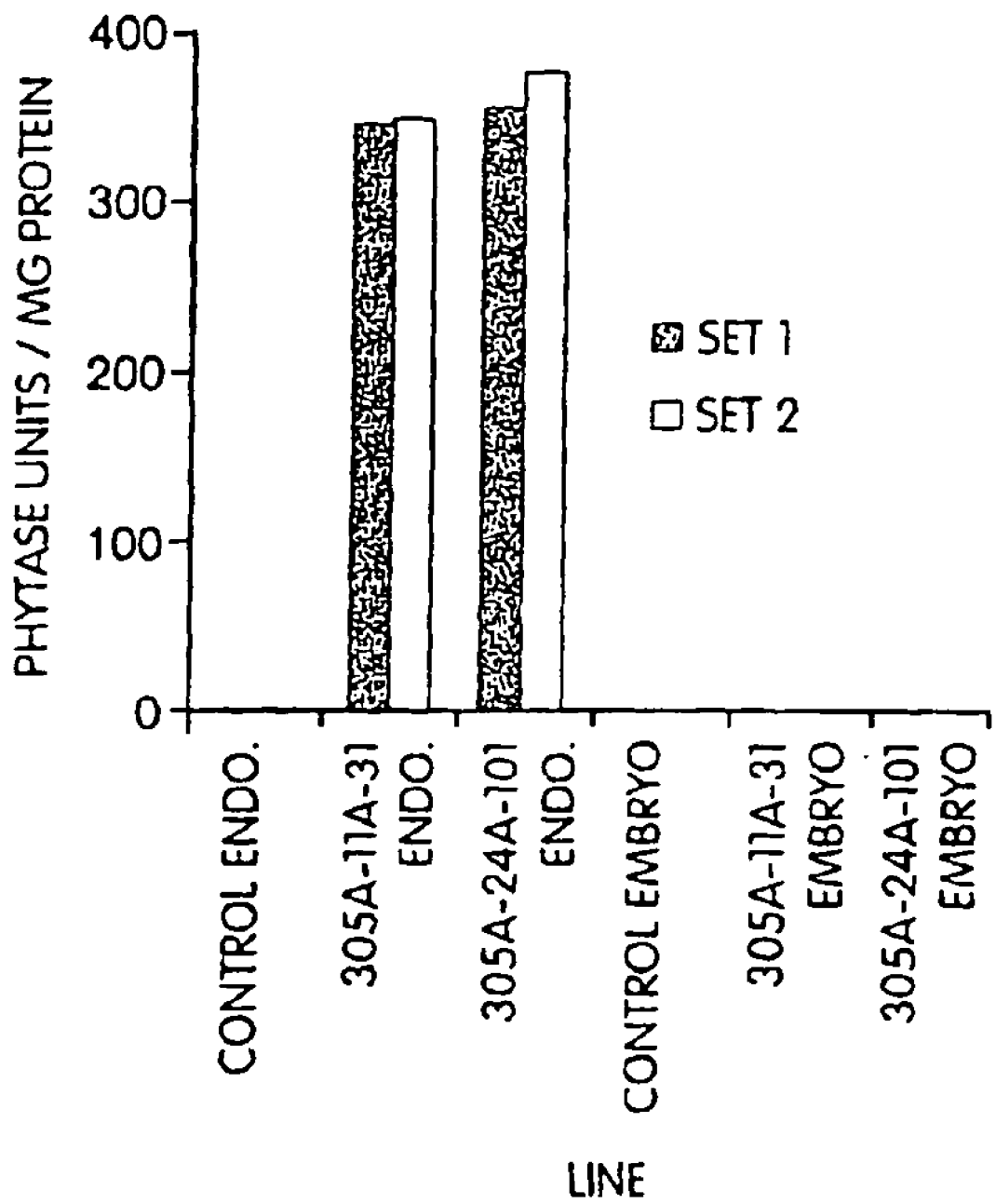
FIG. 5 demonstrates endosperm-specific expression of Nov9X. The figures shows phytase (Nov9X) activity in extracts of T2 endosperm and embryo. Duplicate samples were extracted (sets 1 & 2).

Ears from two T2 plants containing construct pNOV4057 were harvested at 24 and 26 days after pollination. Ten kernels from each plant were dissected into embryos, endosperm, and hulls. Ten endosperm and ten embryos were combined and pulverized with a mortar and pestle in 8 ml distilled water at room temperature. Insoluble material was removed by centrifugation. The specific activity of supernatant fractions of endosperm and embryo samples were determined. As shown in FIG. 5, the specific activity of phytase in extracts of transgenic endosperm exceeded 300. By contrast the specific activity of extracts of transgenic embryos was less than 10. This barely detectable activity was probably due to contamination of embryos with small pieces of endosperm.

Nov9X Phytase is Highly Enriched by Heating Water Extracts of Fresh T2 Endosperm As disclosed above, an exemplary formulation of phytase enzyme produced in corn seed is in the form of a liquid extract. Here, the enrichment of Nov9X phytase by degermination, water extraction, heating, and centrifugation is described.

Figure 6A:
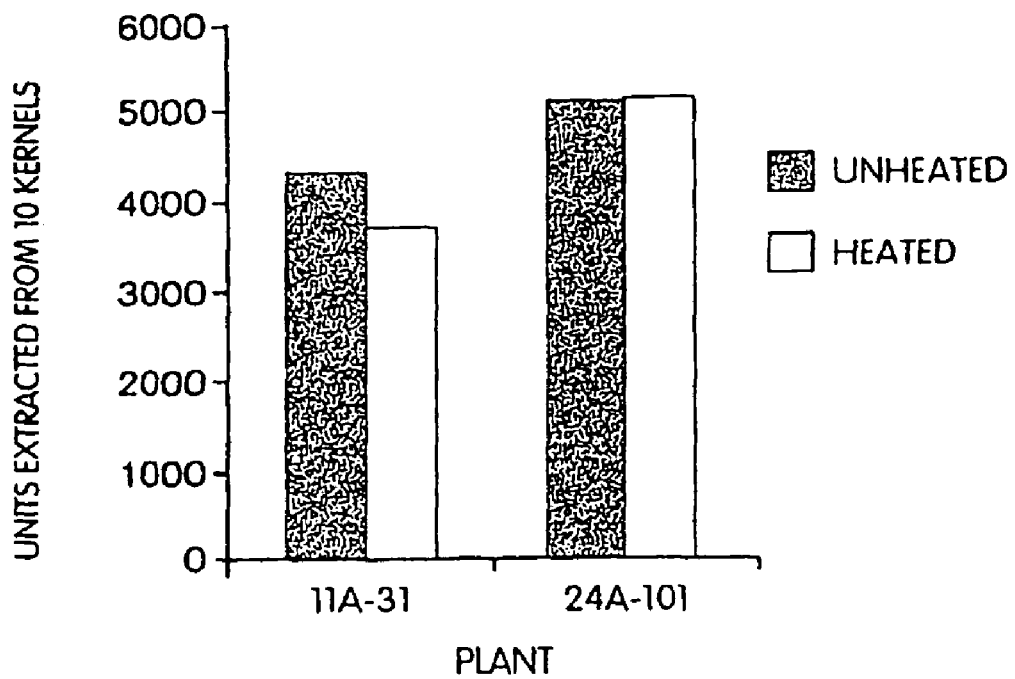
FIG. 6 shows that maize-expressed Nov9X phytase is stable during heating of endosperm extracts and is highly enriched in the soluble fraction of the heated supernatant. A. Phytase activity of unheated and heated samples. B. Phytase specific activity of unheated and heated samples.
Figure 6B:
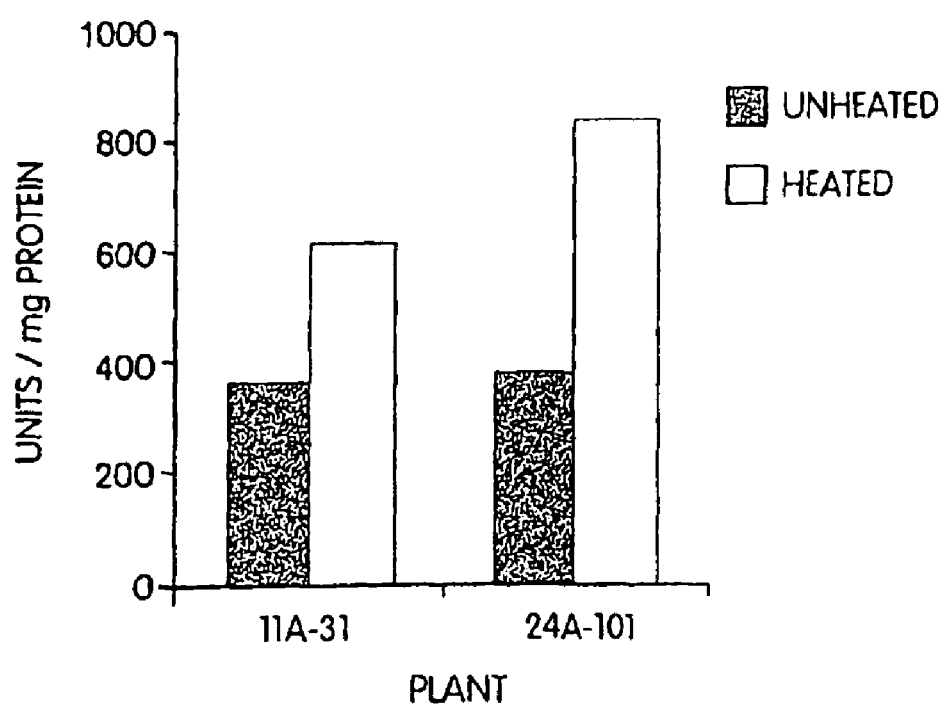

As described above, kernels were degerminated manually and endosperm were pulverized in water using a mortar and pestle. The water extracts of fresh endosperm were heated at 60° C. for 30 min, and insoluble material was removed by centrifugation. Heated and unheated samples were analyzed by SDS-PAGE (gel not shown). A protein of approximately 45 kD (arrow), the predicted size of Nov9X phytase, was enriched in the heated samples. This protein was not present in the control extracts and was the most abundant protein in the transgenic extracts. We conclude that this protein is Nov9X phytase. The total phytase activity was the same in unheated and heated samples (FIG. 6A), demonstrating that Nov9X phytase produced in corn is thermostable. The specific activity of the heated samples increased up to two-fold (FIG. 6B). These results demonstrate a possible strategy for preparing a liquid formulation of Nov9X phytase from corn seed. The same approach using dried endosperm or whole kernel flour should also produce an extract highly enriched for the recombinant enzyme.

Production and Processing of T2 Greenhouse Seed for Poultry Feeding Trials

As disclosed above, an exemplary formulation of phytase enzyme produced in corn seed is as cracked or milled grain, or flour. Phytase-containing flour can be added directly to animal feed as a supplement, or it can be processed further, for example to a pelleted form.

Corn plants were grown in the greenhouse from T1 seed from seven different T0 transgenic events. All plants contained one or more copies of the Nov9X gene as determined by Taqman analysis. These T1 plants were either selfed or fertilized with pollen from a sib or from JHAF031. Ears were harvested at about 30 days after pollination and dried for 5 days at 105° F. The T2 seed from different ears were pooled for each of the six transgenic events. Seeds were milled at room temperature in a fume hood using The Kitchen Mill (K-TEC) set to the finest grind. Batches of seed ranged from 66 g to 398 g. Flour was transferred immediately from the mill chamber to sealed plastic bags in a fume hood. The temperature of the flour was measured immediately after transfer to the plastic bags and did not exceed 41° C. Flour was stored at 4° C.

T2 maize seed derived from six different T0 transgenic events were pooled and milled as described above. A sample of seed from maize inbred A188 was also processed for use as a negative control. The level of phytase activity in maize flour was determined using the procedure described above for protein extraction from dried seed and phytase assays using a microplate format. Protein extractions were performed using duplicate flour samples of about 100 mg.

The six transgenic events selected for seed increase are listed in Table 2. They were derived from plasmids pNOV4057 and pNOV4061, which encode apoplast-targeted and ER-retained forms of Nov9X phytase, respectively. The fraction of seed derived from selfed and crossed plants varied considerably between event pools. Also most T1 plants were not homozygous for Nov9X. These factors make it impossible to correlate enzyme yields with gene copy number in the final T2 seed. The level of extractable phytase activity measured in units per kg flour ranged from 325,000 to 1,300,000 (Table 2).

Table 2 shows the yield of buffer-extractable phytase activity in flour from milled T2 greenhouse seed. A188 is a non-transgenic inbred.

800,000 total units from less than 1 kg flour. The flour described here is an example of a possible formulation of Nov9X phytase for use as a feed additive. Table 3 provides the phytase yields from milled T2 greenhouse seed pooled for apoplast-targeted and ER-retained forms.

TABLE 3

| Binary vector | Subcellular targeting | Units | Flour (g) | Units/kg |
| --- | --- | --- | --- | --- |
| pNOV4061 | ER | 865,063 | 949 | 911,552 |
| pNOV4057 | apoplast | 806,362 | 806 | 1,000,450 |

EXAMPLE 5

Phytase Activity in Seed from Maize Inbreds

Figure 7:
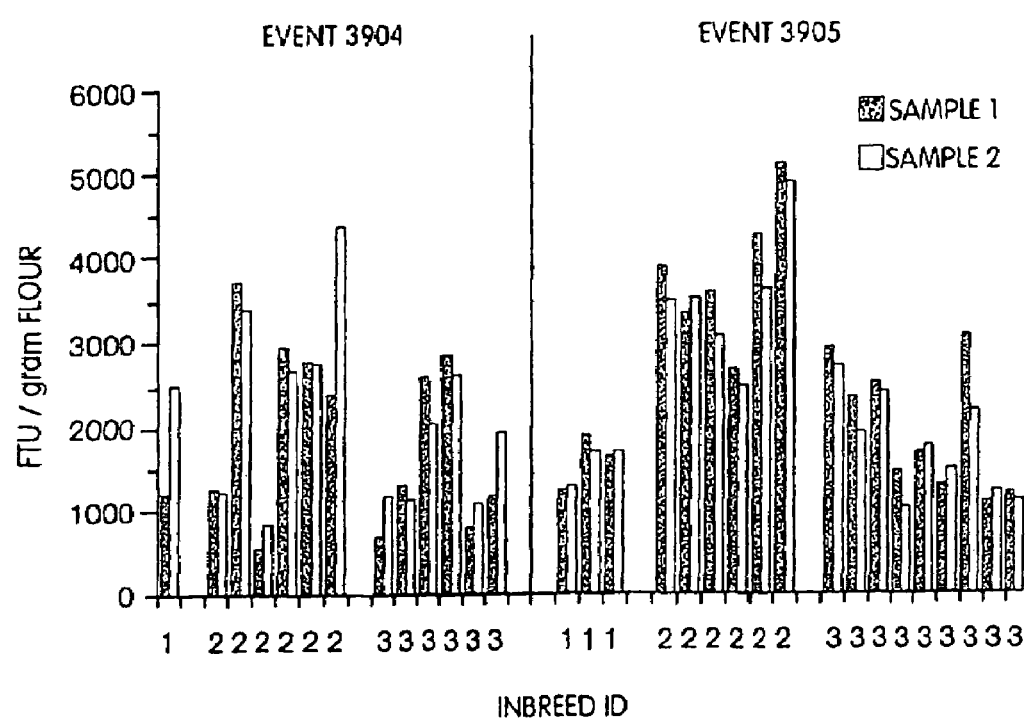
FIG. 7 shows phytase activities (FTU/g) of several lines containing 2 events. Each data point represents phytase activity extracted from 1 g flour obtained by pulverizing 10 kernels. Duplicates samples of 10 kernels were pulverized for each line (samples 1 & 2). Inbred ID substitutes for pollinator, maintainer, and sterile as used in previous version.

Flour samples (1 gram) from several lines containing lead events were extracted in 50 mM Tris-HCl (pH 8.0), 100 mM NaCl, 2 mM for 1 hour at ambient temperature with stirring. Extraction volume was 100 ml. Extracts were clarified by centrifugation and diluted with sodium acetate buffer (pH 5.5) Phytase activity was measured at pH 5.5 and 37 C using the method of Engelen et al. (2001) with modifications. Assays were performed in microplates at a final reaction volume of 1 ml. The results are set forth in FIG. 7.

TABLE 2

| Binary vector | Subcellular targeting | Event | Flour (g) | Average | StDev | Units/kg |
| --- | --- | --- | --- | --- | --- | --- |
|  |  | A188 control | 368 | 0 | 0 |  |
| pNOV4061 | ER | 305B-20A | 398 | 425,666 | 63,228 | 1,069,511 |
| pNOV4061 | ER | 305B-11A | 347 | 298,197 | 2,793 | 859,359 |
| pNOV4061 | ER | 305B-5A | 204 | 141,200 | 15,966 | 692,157 |
| pNOV4057 | apoplast | 305A-20A | 66 | 21,467 | 1,796 | 325,255 |
| pNOV4057 | apoplast | 305A-11A | 313 | 231,439 | 39,498 | 739,423 |
| pNOV4057 | apoplast | 305A-24A RT | 200 | 256,782 | 24,510 | 1,283,910 |
| pNOV4057 | apoplast | 305A-24A cold | 227 | 296,674 | 12,285 | 1,306,934 |

Milling corn at room temperature does not result in decreased phytase activity. The pooled seed derived from event 305A-24A was divided in half before milling. One batch was milled at room temperature. The temperature of the flour from this batch immediately after transfer was 38° C. The other batch was chilled, along with the mill, in a 4° C. cold room for 45 minutes. This batch was then milled in the cold room. The sealed mill was then moved to the fume hood at ambient temperature and the flour was transferred to a plastic bag. The temperature of this cold-milled flour measured immediately after transfer was 24° C. As shown in the bottom two rows of Table 2, milling chilled seeds in the cold did not improve yields of extractable phytase activity. The phytase yield of seeds derived from event 305A-24A that were milled at room temperature (RT) was 1,283,910 units/kg compared to 1,306,934 units/kg for chilled seeds from the same pool milled in the cold.

Table 3 shows the total flour and phytase yields when the separate events are pooled by vector. These data are the sums of the event-specific data in Table 2. The total yields of extractable phytase activity for both the apopast-targeted and ER-retained forms of the enzyme were greater than

EXAMPLE 6

Feeding Trials

Figure 8A:
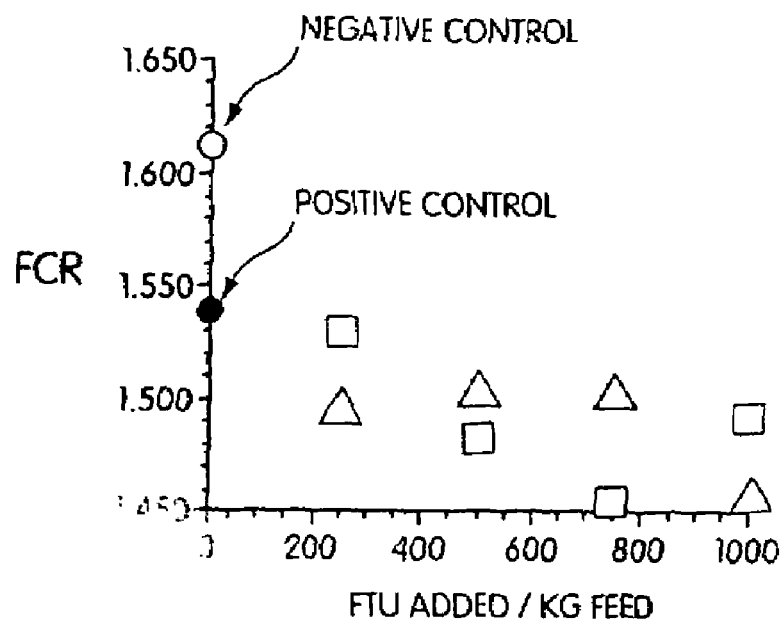
FIGS. 8A, 8B, and 8C show feed conversion ratios (FCRs) from three 21-day chicken feeding trials demonstrate benefit of corn phytase supplementation. FCRs are reported as LSmeans. Available phosphorus: positive controls, 0.400%; negative controls, 0.225%. Phytase supplemented diets were prepared by adding milled transgenic corn to samples of low-phosphate diets (0.225% available phosphorus=negative control). The difference between the negative control diet and the enzyme-supplemented diets is the addition of milled transgenic corn containing Nov9X phytase.
Figure 8B:
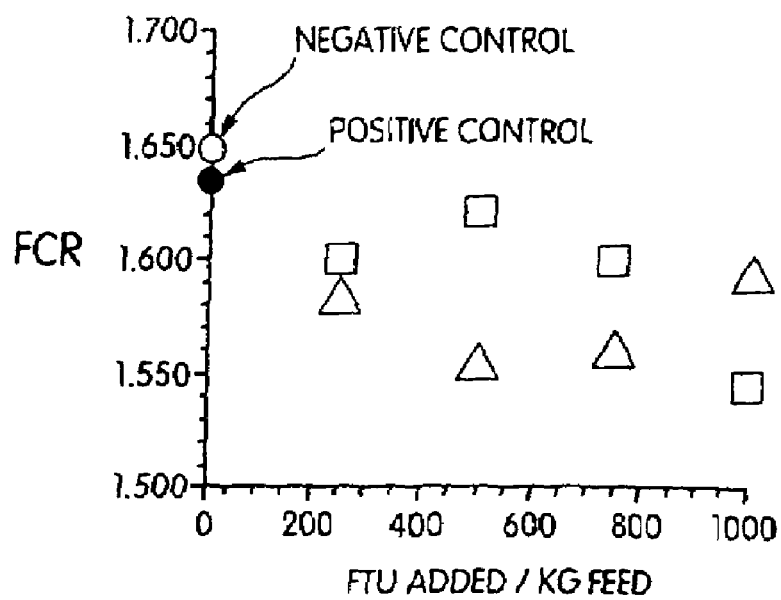
Figure 8C:
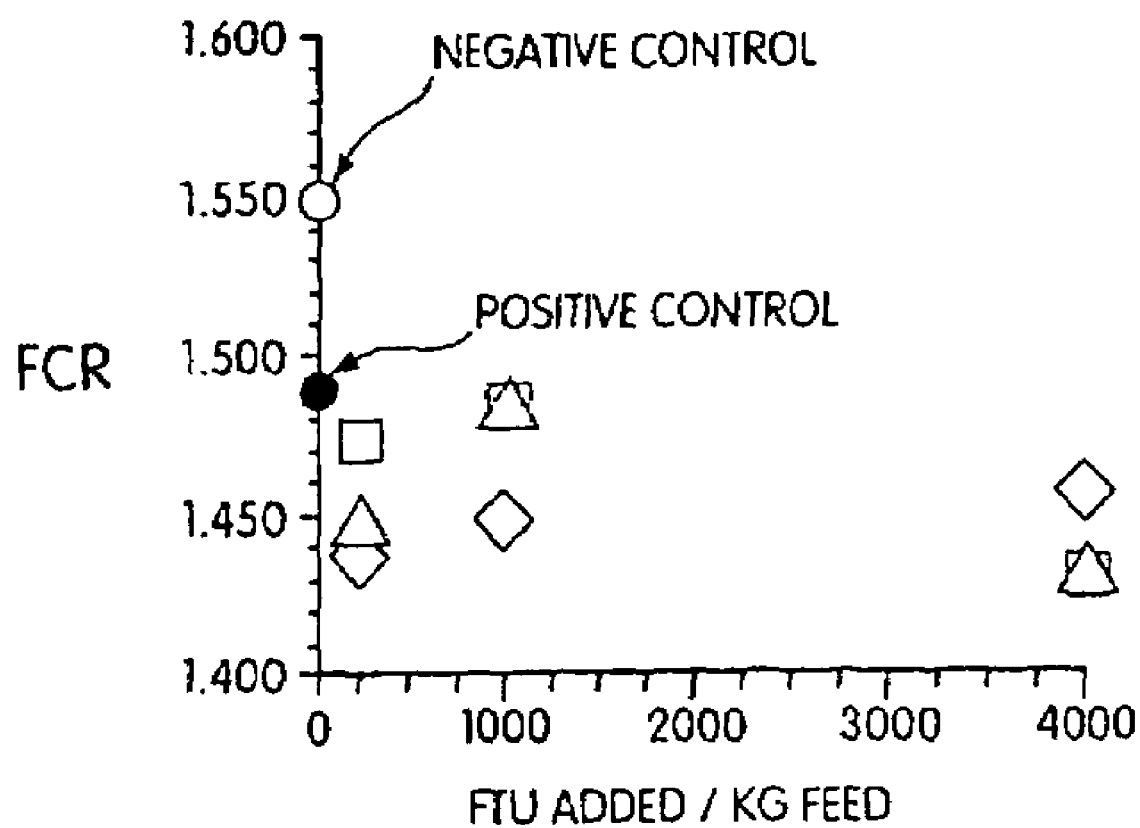

A formulation of phytase from corn seed is as corn flour or grist. FIGS. 8A, 8B, and 8C summarize results from three feeding trials in which chicken feed was supplemented with Nov9X phytase formulated as corn flour. Samples of transgenic corn seed containing extractable phytase activity were milled using a hammer or disc mill and were then added directly to feed samples and mixed thoroughly. Treated feed was either used directly as mash feed (trial I) or was steam conditioned and pelleted (trials II and III). In all cases phytase corn flour was added to feed rations that contained reduced levels of phosphate (negative control). This allowed comparison of low phosphate diet (negative control), high phosphate diet (positive control), and low phosphate diets supplemented with phytase formulated as milled corn.

The results in FIGS. 8(A, B, and C) are plotted as feed conversion ratios (FCRs). FCR refers to the amount of feed consumed divided by the net weight gain of the chicken. A lower ratio indicates that a chicken gained more weight per unit of feed consumed. A lower ratio indicates that a chicken more efficiently utilized the feed that was consumed. Standard poultry diets are used and two inorganic phosphate levels are incorporated into the diets, 0.450% (positive control) and 0.225% (negative control and enzyme-supplemented diets). The 0.45% level is commonly used in commercial poultry diets. Replicate pens of 8 chickens for each diet are grown until 21 days of age, and final weights determined by subtracting the weight of the one day old chicks. Records are kept of the amount of feed consumed by each pen of chickens, and an average feed consumption is determined.

FIG. 8A shows results from a trial in which chickens were fed mash diets. For this trial, Nov9X phytase was formulated by grinding whole transgenic corn kernels to flour. Transgenic kernels were harvested from plants containing vectors pNOV4057 (apoplast-targeted phytase) or pNOV4061 (ER-retained phytase)(see Table 2). Supplementation of low phosphate diets with Nov9X phytase as corn flour improved FCR and restored performance to levels equal to or better than that of the positive control. These results demonstrate that Nov9X phytase formulated as corn flour improves FCR in chickens fed a low phosphate diet.

FIG. 8B shows results from a trial in which chickens were fed pelleted feed. For this trial Nov9x phytase formulated as corn flour was added to low phosphate chicken feed before steam conditioning and pelleting. As in FIG. 8A, the apoplast-targeted and ER-retained form of Nov9x phytase were tested. Phytase supplementation restored performance to levels equal to or better than that observed for the positive control. These results demonstrate that Nov9x phytase synthesized directly in corn seed and formulated as corn flour improves FCR in chickens fed a low phosphate diet.

FIG. 8C shows results from a trial in which the apoplast-targeted form of Nov9x phytase (encoded by vector pNOV4057) was formulated as a fine grind corn flour, a medium grind, or a coarse grind corn flour. Coarse grind material consisted predominantly of particles >2000 microns; medium grind material was predominantly in the size range of 500–2000 microns; and fine grind flour was <500 microns. The three formulations were added to low phosphate rations prior to steam conditioning and pelleting as in FIG. 8B. Feed conversion ratios were improved at all doses tested for all three formulations. And all three formulations outperformed the positive control at all doses tested. These results demonstrate efficacy in chickens of the preferred formulation of Nov9X phytase as cracked corn seed.

REFERENCES

Abelson, P. H., *Science*, 283: 2015 (1999).
An. et al., *EMBO J.*, 4:277 (1985).
Aoyama T. et al., *N—H Plant Journal*, 11:605 (1997).
Arnold et al., *Chem. Eng. Sci.*, 51:5091 (1996).
Ballas et al., *Nucleic Acids Res.*, 17:7891 (1989).
Bansal et al., *Proc. Natl. Acad. Sci. USA*, 89:3654 (1992).
Batzer et al., *Nucleic Acid Res.*, 19:5081 (1991).
Beals et al., *Plant Cell*, 9:1527 (1997).
Belanger et al., *Genetics*, 129, 863 (1991).
Berlan, J.-P. et al., *Eur. R. Agric. Eco.*, 4, 395 (1977).
Bevan et al., *Nucl. Acids Res.*, 11:369 (1983).
Bevan et al., *Nature*, 304: 184 (1983).
Bevan, *Nucl. Acids Res.* (1984).
Bird et al., *Plant Molecular Biology*, 11:651 (1988).
Blochinger & Diggelmann, *Mol Cell Biol*, 4; 2929.
Bouchez et al., *EMBO Journal*, 8:4197 (1989).
Bourouis et al., *EMBO J.*, 2;1099 (1983).
Byrne et al. *Plant Cell Tissue and Organ Culture*, 8:3 (1987).
Callis et al., *Genes and Develop.*, 1:1183 (1987).
Campbell and Gowri, *Plant Physiol.*, 92:1 (1990).
Chandler et al., *Plant Cell*, 1:1175 (1989).
Chee et al., *Plant Physiol.*, 91:1212 (1989).
Christou et al., *Biotechnology*, 9, 957 (1991).
Christou et al., *Plant Physiol.*, 87, 671 (1988).
Christou et al., *Proc. Natl. Acad. Sci USA*, 86:7500 (1989).
Cooper, R. J. and Gowing, H. S., *Brit. J. Nutr.*, 50, 429 (1983).
Cordero et al., *Plant J.*, 6:141 (1994).
Crameri et al., *Nature Biotech.*, 15:436 (1997).
Crameri et al., *Nature*, 391:288 (1998).
Crossway et al., *BioTechniques*, 4:320 (1986).
Czako et al., *Mol. Gen. Genet.*, 235:33 (1992).
Datta et al., *Bio/Technology*, 8, 736 (1990).
Dayhoff et al., *Atlas of Protein Sequence and Structure*, Natl. Biomed. Res. Found., Washington, C.D. (1978)
De Blaere et al., *Meth. Enzymol.*, 143, 277 (1987).
De Block et al., *EMBO Journal*, 6:2513 (1987).
De Block et al., *Plant Physiol.*, 91:694 (1989).
Dellaporta et al., in *Chromosome Structure and Function*, pp. 263–282 (1988).
Dennis et al., *Nucleic Acids Res.*, 12:3983 (1984).
Diekman & Fischer, *EMBO*, 7:3315 (1988).
Ellis et al., *EMBO Journal*, 6:3203 (1987).
Engelen, A. J. et al., *J. AOAC. Inter.*, 77, 760 (1994).
Engelen, A. J. et al., *J. AOAC. Inter.*, 84, 629 (2001).
Everett et al., *Bio/Technology*, 5:1201(1987).
Franken et al., *EMBO J.*, 10:2605 (1991).
Fromm et al. *Nature (London)*, 319:791 (1986).
Fromm et al., *Bio/Technology*, 8, 833 (1990).
Gallie, et al., *The Plant Cell*, 1:301(1989).
Gan et al., *Science*, 270:1986 (1995).
Gatz, *Current Opinion in Biotechnology*, 7:168 (1996).
Gatz, C., *Annu. Rev. Plant Physiol. Plant Mol. Biol.*, 48:89 (1997).
Gelfand, eds., *PCR Strategies* (Academic Press, New York (1995).
Gelvin et al., *Plant Molecular Biology Manual* (1990).
Gonni et al. (*Agric. Biol. Chem.*, 51, 2549 (1987).
Gordon Kamm et al., *Plant Cell* 2:603 (1990).
Graham et al., *Biochem. Biophys. Res. Comm.*, 101:1164 (1981).
Graham et al., *J. Biol. Chem.*, 260:6561 (1985).
Gritz et al., *Gene*, 25, 179 (1983).
Gruber, et al., *Methods in Plant Molecular Biology & Biotechnology*, Glich et al., Eds. pp. 89–119, CRC Press (1993).
Guerineau et al., *Mol. Gen. Genet.*, 262:141 (1991).
Hiei et al., *Plant J.*, 6:271(1994).
Hinchee et al., *Bio/Technology*, 6:915 (1988).
Hinchee et al., *Biotechnology*, 6: 915 (1988).
Hoekema, In: *The Binary Plant Vector System*. Offset-drukkerij Kanters B. V.; Alblasserdam (1985).
Horsch et al., *Science* 227:1229 (1985).
Hudspeth & Grula, *Plant Mo. Bio.*, 12:579 (1989).
Ikuta et al., *Biotech.*, 8:241 (1990).
Ingelbrecht et al., *Plant Cell*, 1:671 (1989).
Innis and Gelfand, eds., *PCR Methods Manual* (Academic Press, New York) (1999).
Innis et al., eds., *PCR Protocols: A Guide to Methods and Applications* (Academic Press, New York (1995).
John et al., *Proc. Natl. Acad. Sci. USA*, 89:5769 (1992).
Jongbloed et al., *Enzymes in Animal Nutrition. Proc. of the 1st Symp. Kartause Ittingen*, Wenk, C. and Boessinger, M. (Eds.), Switzerland, pp. 173–180 (1993).
Joshi et al., *Nucleic Acid Res.*, 15:9627 (1987).

Katz et al., *J. Gen. Microbiol.,* 129:2703 (1983).
Keller et al., *EMBO Journal,* 8:1309 (1989).
Keller et al., *Genes Dev.,* 3:1639 (1989).
Klein et al., *Bio/Technology,* 6, 559 (1988).
Klein et al., *Nature (London),* 327:70 (1987).
Klein et al., *Plant Physiol.,* 91:440 (1988).
Klein et al., *Proc. Natl. Acad. Sci. USA,* 85, 4305 (1988).
Klosgren et al., *Mol. Gen. Genet.,* 203, 237 (1986).
Knauf et al., *Molecular Genetics of the Bacteria-Plant Interaction,* Puhler, A. ed., Springer-Verlag, New York, p. 245 (1983).
Kohler et al., *Plant Mol. Biol.,* 29;1293 (1995).
Kornegay, E. T. et al., *Brit. J. Nutr.,* 75, 839 (1996).
Koziel et al., *Biotechnology,* 11: 194 (1993).
Kridl et al., *Seed Science Research,* 1:209 (1991).
Kriz et al., *Mol. Gen. Genet.,* 207:90 (1987).
Kunkel et al., *Methods in Enzymol.,* 154:367 (1987).
Kunkel, *Proc. Natl. Acad. Sci. USA,* 82:488 (1985).
Laemmli, U.K. (1970), Cleavage of structural proteins during the assembly of the head of bacteriophage T4. *Nature* 227: 680–685.
Langridge et al., *Proc. Natl. Acad. Sci. USA,* 86:3219 (1989).
Langridge et al., *Cell,* 34:1015 (1983).
Lanyon, *Agriculture and Phosphorus Management* (A. N. Sharpley, ed.), pp. 145–158. Lewis Publishers, Boca Raton, Fla. (1999).
Lawton et al., *Mol. Cell Biol.,* 7:335 (1987).
Lee et al., *Plant Mol. Biol.,* 26, 1981 (1994).
Lindstrom et al., *Der. Genet.,* 11:160 (1990).
Lorz et al. *Mol. Gen. Genet.,* 199:178 (1985).
Maki et al., *Methods in Plant Molecular Biology & Biotechnology,* Glich et al., Eds., pp. 67–88 CRC Press (1993).
Mansson et al., *Gen. Genet.,* 200:356 (1985).
Martinez et al., *J. Mol. Biol.,* 208:551 (1989).
Martinez-Zapater and Salinas, *Methods in Molecular Biology,* 82, Humana Press (1998).
McCabe et al., *Bio/Technology,* 6:923 (1988).
McElroy et al., *Mol. Gen. Genet.,* 231:150 (1991).
Messing & Vierra, *Gene,* 19: 259 (1982).
Mogen et al., *Plant Cell,* 2:1261 (1990).
Moore et al., *J. Mol. Biol.,* 272:336 (1997).
Mroz, Z. et al., *J. Anim. Sci.,* 72, 126 (1994).
Munro et al., *Cell* 48, 899 (1987).
Munroe et al., *Gene,* 91:151 (1990).
Murakami et al., *Mol. Gen. Genet.,* 205:42 (1986).
Murray et al., *Nucleic Acids Res.,* 17:477 (1989).
Negrotto et al., *Plant Cells Reports* 19:798–803 (2000).
Niedz et al., *Plant Cell Reports,* 14: 403 (1995).
Odell et al. *Mol. Gen. Genet.,* 113:369 (1990).
Odell et al., *Nature* 313:810 (1985).
Ohtsuka et al., *J. Biol. Chem.,* 260:2605 (1985).
Okamuro et al., *Biochemistry of Plants,* 15:1 (1989).
Ow et al., *Science,* 234:856 (1986).
Pacciotti et al. *Bio/Technology,* 3:241 (1985).
Pallauf, J. and Rimbach, G., *Arch. Anim. Nutr.,* 50, 301 (1997).
Park et al., *J. Plant Biol.,* 38:365 (1985).
Paszkowski et al., *EMBO J.,* 3, 2717 (1984) Pear et al., *Plant Molecular Biology,* 13:639 (1989).
Perlak et al., *Proc. Natl. Acad. Sci. USA,* 88:3324 (1991).
Phillips et al. *Corn & Corn Improvement,* 3rd Edition., Sprague et al., Eds., pp. 345–387) American Society of Agronomy Inc. et al. (1988).
Potrykus et al., *Mol. Gen. Genet.,* 199:183 (1985).
Potrykus, *Trends Biotech.,* 7:269 (1989).
Poulsen et al., *Mol. Gen. Genet.,* 205:193 (1986).
Prasher et al., *Biochem. Biophys. Res. Comm.,* 126:1259 (1985).
Quigley et al., *J. Mol. Evol.,* 29:412 (1989).
Ralston et al., *Genetics,* 119:185 (1988).
Rao, R. S. V. et al., *Anim. Feed Sci. Technol.,* 79, 211 (1999).
Ravindran, V. et al., *Poult. Sci.,* 78, 699 (1999).
Reina et al., *Nucleic Acids Res.,* 18:7449 (1990).
Riggs et al., *Proc. Natl. Acad. Sci. USA,* 83, 5602 (1986).
Rimbach, G. et al., *Ern=hrungsforschunz,* 39, 1 (1994).
Rodriguez et al., *Arch. Biochem., Biophy.,* 365:262 (1999).
Rodriguez et al., *Arch. Biochem., Biophy.,* 382:105 (2000).
Rossolini et al., *Mol. Cell. Probes,* 8:91 (1994).
Rothstein et al., *Gene,* 53, 153 (1987).
Rumsey, G. L., *Fisheries,* 18, 14 (1993).
Sambrook et al., *Molecular Cloning: A Laboratory Manual* (2d ed., Cold Spring Harbor Laboratory Press, Plainview, N.Y.) (1989).
Sanfacon et al., *Genes Dev.,* 5:141 (1991).
Sanford et al., *Particulate Science and Technology,* 5, 27 (1987).
Schwob et al., *Plant J.,* 4:423 (1993).
Shaw and Hannah, *Plant Physiol,* 98, 1214 (1992).
Shimamoto et al., *Nature,* 338, 274 (1989).
Simpson, *Plant Mo. Bio.,* 19:699 (1986).
Slater et al., *Plant Mol. Biol.,* 5:137 (1985).
Smith et al., *Planta,* 168:94 (1986).
Spencer et al., *Theor. Appl. Genet,* 79: 625 (1990).
Stalker et al., *Science* 242:419 (1988).
Steifel et al., *The Plant Cell,* 2:785 (1990).
Stemmer, *Nature,* 370:389 (1994).
Stemmer, *Proc. Natl. Acad. Sci. USA,* 91:10747 (1994).
Sukhapinda et al. *Plant Mol. Biol.,* 8:209 (1987).
Sullivan et al., *Mol. Gen. Genet.,* 215:431 (1989).
Sutcliffe, *PNAS USA,* 75:3737 (1978).
Svab et al., *Proc. Natl. Acad. Sci. USA,* 87, 8526 (1990).
Thillet et al., *J. Biol. Chem.,* 263:12500 (1988).
Thompson et al., *EMBO Journal,* 6:2519 (1987).
Tomes et al., *Plant Cell, Tissue and Organ Culture: Fundamental Methods,* Gamborg and Phillips (Eds.), Springer Verlag, Berlin (1995)
Torrent et al., *Plant Mol. biol.,* 34, 139 (1997).
Turner et al., *Molecular Biotechnology,* 3:225 (1995).
Twell et al., *Plant Physiol.,* 91:1270 (1989).
Ugaki et al., *Nucl. Acids Res.,* 19:371 (1991).
Ulmasov et al. *Plant Mol. Biol.,* 35:417 (1997).
Van Der Klis and Versteegh, Recent Advances in Animal Nutrition, pp. 71–83 (1996).
vanTunen et al., *EMBO J.,* 7;1257(1988).
Vasil et al., *Biotechnology,* 11, 1553 (1993).
Vasil et al., *Mol. Microbiol.,* 3:371 (1989).
Vasil et al., *Plant Physiol.,* 91:1575 (1989).
Vodkin, *Prog. Clin. Biol. Res.,* 138;87 (1983).
Vogel et al., *EMBO J.,* 11:157 (1989).
Wada et al., *Nucl. Acids Res.,* 18:2367 (1990).
Walker and Gaastra, eds., *Techniques in Molecular biology*, MacMillan Publishing Company, New York (1983).
Wandelt et al., *Nucleic Acids Res.,* 17:2354 (1989).
Wang et al., *Mol. Cell. Biol.,* 12:3399 (1992).
Weeks et al., *Plant Physiol.,* 102, 1077 (1993).
Weissinger et al., *Annual Rev. Genet.,* 22, 421 (1988).

Wenzler et al., *Plant Mol. Biol.,* 13:347 (1989).
White et al., *Nucl Acids Res,* 18; 1062 (1990).
Williams, P. J. and Taylor, T. G., *Brit. J. Nutr.,* 45, 429 (1985).
Wyss et al., *App. Environ. Micro.,* 65:359 (1999).
Yamamoto et al., *Nucleic Acids Res.,* 18:7449 (1990).
Zhang et al., *Proc. Natl. Acad. Sci. USA,* 94:4504 (1997).
Zukowsky et al., *PNAS USA,* 80:1101 (1983).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The invention claimed is:

1. A method to prepare a thermotolerant phytase comprising:
    expressing in a plant cell an expression cassette comprising a promoter operably linked to a nucleic acid molecule encoding a thermotolerant phytase which retains at least 40% activity after 30 minutes at 60° C. and has a specific activity of greater than 200 U/mg at pH 4.5 and 37° C. and wherein the thermotolerant phytase comprises the polypeptide sequence depicted in amino acids 20–431 of SEQ ID NO:4 or a conservative variant thereof.

2. The method of claim 1 further comprising isolating the thermotolerant phytase.

3. The method of claim 1 wherein the thermotolerant phytase comprises SEQ ID NO:4.

4. The method of claim 1 wherein the thermotolerant phytase has a specific activity of greater than 400 U/mg at pH 4.5 and 37° C.

5. The method of claim 1 wherein the thermotolerant phytase has a specific activity of greater than 600 U/mg at pH 4.5 and 37° C.

6. The method of claim 1 wherein the thermotolerant phytase has a specific activity of greater than 800 U/mg at pH 4.5 and 37° C.

7. The method of claim 1 wherein the promoter is a ubiquitin promoter.

8. The method of claim 1 wherein the promoter is a plant tissue-specific promoter.

9. The method of claim 8 wherein the promoter is an endosperm-specific promoter.

10. The method of claim 9 wherein the endosperm-specific promoter is a maize γ-zein promoter or a maize ADP-glucose pyrophosphorylase promoter.

11. The method of claim 10 wherein the promoter comprises SEQ ID NO:8 or SEQ ID NO:9.

12. The method of claim 1 wherein the promoter is a plant embryo-specific promoter.

13. The method of claim 12 wherein the promoter comprises a maize globulin 1 promoter.

14. The method of claim 12 wherein the promoter comprises a maize oleosin KD18 promoter.

15. The method of claim 4 wherein the plant cell is a maize, wheat or soybean cell.

16. The method of claim 1 wherein the nucleic acid molecule encodes a fusion polypeptide comprising the thermotolerant phytase.

17. The method of claim 16 wherein the fusion polypeptide comprises a signal sequence which is operably linked to the phytase.

18. The method of claim 17 wherein the signal sequence targets the phytase to an amyloplast, endoplasmic reticulum, apoplast, or starch granule in the cells of a plant.

19. The method of claim 17 wherein the signal sequence is an N-terminal signal sequence from waxy or an N-terminal signal sequence from γ-zein.

20. The method of claim 17 wherein the signal sequence is a starch binding domain.

21. The method of claim 20 wherein the starch binding domain is a waxy starch encapsulating domain which is operably linked to the C-terminus of the thermotolerant phytase.

22. The method of claim 17 wherein the fusion polypeptide comprises SEKDEL operably linked to the C-terminus of the thermotolerant phytase.

23. The method of claim 1 wherein the thermotolerant phytase has a half life of greater than 25 minutes at a pH greater than 2.0 and less than 4.0.

24. The method of claim 1 wherein the thermotolerant phytase is glycosylated.

25. A method of preparing animal feed comprising:
    a) providing a mixture of a feed component and a phytase preparation comprising the thermotolerant phytase of claim 1 or 2;
    b) treating the mixture under conditions of temperature and moisture which hydrolyze phytic acid that is present in said mixture so as to yield animal feed.

26. Animal feed prepared by the method of claim 25, wherein said animal feed has reduced phytic acid content relative to the phytic acid content that would have been present in feed made with the untreated component.

27. A method of preparing animal feed, comprising:
    a) providing a mixture comprising animal feed components and a phytase preparation comprising the thermotolerant phytase of claim 1 or 2; and b) heating the mixture at a temperature greater than 50° C. so as to yield a heat-treated animal feed mixture.

28. The method of claim 27 wherein the phytase preparation is a liquid mixture.

29. The method of claim 27 wherein the phytase preparation is a solid mixture.

30. The method of claim 27 wherein the preparation is transgenic plant material.

31. The method of claim 30 wherein the transgenic material is transgenic corn grain, cracked corn, corn flour, or an enzyme extract prepared from corn.

32. The method of claim 27 wherein the phytase preparation further comprises at least one vitamin, mineral, an enzyme other than a thermotolerant phytase, an organic acid, probiotic (bacterial) or essential oil or a co-product.

33. The method of claim 27 wherein the phytase preparation is less than about 1% inorganic phosphate.

34. The method of claim 27 wherein the mixture in a) has less than 0.45% inorganic phosphate.

35. A heat-treated animal feed mixture produced by the method of claim 27.

36. The method of claim 27 further comprising extruding the heat-treated mixture through a pellet mill to yield pelletized animal feed.

37. Pelletized animal feed produced by the method of claim 36.

38. The animal feed composition comprising a phytase of claim 1 or 2.

39. The animal feed composition of claim 38 wherein the phytase has a specific activity of greater than 400 U/mg at pH 4.5 and 37° C.

40. The animal feed composition of claim 38 wherein the phytase has a specific activity of greater than 600 U/mg at pH 4.5 and 37° C.

41. The animal feed composition of claim 38 wherein the phytase has a specific activity of greater than 800 U/mg at pH 4.5 and 37° C.

42. The animal feed composition of claim 38 wherein the thermotolerant phytase has a half life of greater than 25 minutes at a pH greater than 2.0 and less than 4.0.

43. An enzyme feed additive comprising the thermotolerant phytase of claim 1 or 2.

44. The enzyme feed additive of claim 43 wherein the thermotolerant phytase has a specific activity of greater than 400 U/mg at pH 4.5 and 37° C.

45. The enzyme feed additive of claim 43 wherein the thermotolerant phytase has a specific activity of greater than 600 U/mg at pH 4.5 and 37° C.

46. The enzyme feed additive of claim 43 wherein the thermotolerant phytase has a specific activity of greater than 800 U/mg at pH 4.5 and 37° C.

47. The enzyme feed additive of claim 43 wherein the thermotolerant phytase has a half life of greater than 25 minutes at a pH greater than 2.0 and less than 4.0.

48. A feed pellet comprising the thermotolerant phytase of claim 1.

49. A feed pellet comprising the thermotolerant phytase of claim 2.

* * * * *